(12) United States Patent
Hyde et al.

(10) Patent No.: US 8,215,311 B2
(45) Date of Patent: *Jul. 10, 2012

(54) MEDICAL DISPLACEABLE CONTOURING MECHANISM

(75) Inventors: Roderick A. Hyde, Livermore, CA (US); Muriel Y. Ishikawa, Livermore, CA (US); Edward K. Y. Jung, Bellevue, WA (US); Eric C. Leuthardt, St Louis, MO (US); Royce A. Levien, Lexington, MA (US); Robert W. Lord, Seattle, WA (US); Mark A. Malamud, Seattle, WA (US); Nathan P. Myhrvold, Medina, WA (US); Dennis J. Rivet, St Louis, MO (US); John D. Rinaldo, Jr., Bellevue, WA (US); Michael A. Smith, San Gabriel, CA (US); Clarence T. Tegreene, Bellevue, WA (US); Lowell L. Wood, Jr., Livermore, CA (US); Victoria Y. H. Wood, Livermore, CA (US)

(73) Assignee: The Invention Science Fund I, LLC

( * ) Notice: Subject to any disclaimer, the term of this patent is extended or adjusted under 35 U.S.C. 154(b) by 234 days.

This patent is subject to a terminal disclaimer.

(21) Appl. No.: 12/800,188

(22) Filed: May 11, 2010

(65) Prior Publication Data

US 2010/0218315 A1 Sep. 2, 2010

Related U.S. Application Data

(63) Continuation-in-part of application No. 11/503,489, filed on Aug. 10, 2006, now Pat. No. 7,789,086, and a continuation-in-part of application No. 11/589,317, filed on Oct. 27, 2006, now Pat. No. 7,740,015.

(51) Int. Cl.
*A61G 15/00* (2006.01)
*A47B 71/00* (2006.01)
*A47B 7/00* (2006.01)

(52) U.S. Cl. ................. 128/845; 5/613; 5/600
(58) Field of Classification Search .............. 5/731, 241, 5/244, 239, 710, 933, 934, 613, 600, 713, 5/715, 722, 935; 128/845, 869
See application file for complete search history.

(56) References Cited

U.S. PATENT DOCUMENTS 3,656,190 A 4/1972 Regan et al.
(Continued)

OTHER PUBLICATIONS

"ADATTO hospital bed"; Merivaara.com; pp. 1-6; located at http://www.sw.dk/files/Merivaara_Adatto_uk_3352.pdf.

(Continued)

*Primary Examiner* — Patricia Bianco
*Assistant Examiner* — Tarla Patel

(57) ABSTRACT

One aspect relates to reducing a pressure differential across one or more supporting surfaces of a body surface of an individual at least partially by displacing at least one displaceable contouring unit to at least partially conform to one or more contours of the body surface of the individual. Certain aspects can relate to stabilizing at least the one or more supporting surfaces of the body surface of the individual at least partially with at least one of the at least one displaceable contouring unit Other aspects can relate to relatively displacing at least one displaceable contouring unit with respect to a medical device portion based at least in part on a contour of an individual to support at least a portion of the individual while limiting pressure applied to the individual.

19 Claims, 29 Drawing Sheets

U.S. PATENT DOCUMENTS

| | | | |
|---|---|---|---|
| 4,757,983 | A | 7/1988 | Ray et al. |
| 4,808,063 | A | 2/1989 | Haley |
| 4,852,195 | A | 8/1989 | Schulman |
| 5,197,975 | A * | 3/1993 | Mombrinie .................. 606/238 |
| 5,496,263 | A | 3/1996 | Fuller, II et al. |
| 5,873,137 | A | 2/1999 | Yavets-Chen |
| 6,192,538 | B1 | 2/2001 | Fogel |
| 6,523,198 | B1 | 2/2003 | Temple |
| 7,789,086 | B2 * | 9/2010 | Hyde et al. .................. 128/845 |
| 2004/0064896 | A1 | 4/2004 | Partian |
| 2006/0085919 | A1 | 4/2006 | Kramer et al. |
| 2006/0174895 | A1 | 8/2006 | Ferguson et al. |

OTHER PUBLICATIONS

"An Image Processing Approach to Surface Matching"; Eurographics Symposium on Geometry Processing; bearing a date of 2005; pp. 1-11; located at http://csdrm.caltech.edu/publications/cit-asci-tr/cit-asci-tr292.pdf.

"Conventional Table: manual—hydraulic OPT/20, Operating Table OPT/20, Multifunctional Operating Table"; OPT Officina DI Protesi Trento SpA; printed on Jul. 24, 2006; pp. 1-3; located at http://gbf.micronet.it/Opt/inglese/20_chir_ing.shtml.

Graham, P.A.; Moore, C.J.; Mackay, R.I.; Sharrock, P.J.; "Dynamic surface matching for patient positioning in radiotherapy"; IEEE; bearing dates of Jul. 29-31, 1998, Aug. 6, 2002, and 2006; printed on Aug. 7, 2006; pp. 1; located at http://ieeexplore.ieee.org/xpl/absprintf.jsp?arnumber=694194.

"Hospital beds"; Craftmatic.com; bearing a date of 2005; printed on Jul. 24, 2006; pp. 1; located at http://www.craftmatic.com/pages/hospital-beds.html.

"Introducing Oasis Reusable Gel Positioning Products"; Kendall-ltp.com; bearing a date of 2000-2005; printed on Aug. 7, 2006; pp. 1; located at http://www.kendall-ltp.com/devoasis.htm.

Lacasse, Richard J.; "National Radio Astronomy Observatory, GBT Active Surface Hardware"; Gb.nrao.edu; bearing a date of Jul. 15, 2002; printed on Aug. 7, 2006; pp. 1-7; located at http://www.gb.nrao.edu/GBT/ActiveSurface/hardware.html.

Moore, C.J.; Graham P.A.; "3D dynamic body surface sensing and CT-body matching: a tool for patient set-up and monitoring in radiotherapy"; Pubmed.gov; bearing a date of 2000 and Aug. 7, 2006; printed Aug. 7, 2006; pp. 1; located http://www.ncbi.nlm.nih.gov/entrez/query.fcgi?cmd=Retrieve&db=PubMed&list_uids=11029157&dopt=Abstract.

"Oasis Positioning Products from Kendall-LTP"; Kendall-ltp.com; bearing a date of Feb. 2003; pp. 1-4; located at http://www.kendall-ltp.com/pdf/oasis.pdf (not provided, unable to pring document due to website error).

"Operating Room Products"; Disabilityuk.com; printed on Jul. 24, 2006; pp. 1-10; located at http://disabilityuk.com/products-disability/dan_medica_south_files/operating_room_products.htm.

"Rest Mate supports your upper body while resting"; Seniorshops.com; bearing a date of 1999-2006; printed on Jul. 24, 2006; pp. 1-2; located at http://seniorshops.com/restmate.html.

Webster, C.I.; "A pressure care survey in the operating theatres." Pubmed.gov; bearing dates of 1993 and Jul. 17, 2006; printed on Jul. 24, 2006; pp. 1-2; located at http://www.ncbi.nlm.nih.gov/entrez/query.fcgi?CMD=Display&DB=pubmed.

* cited by examiner

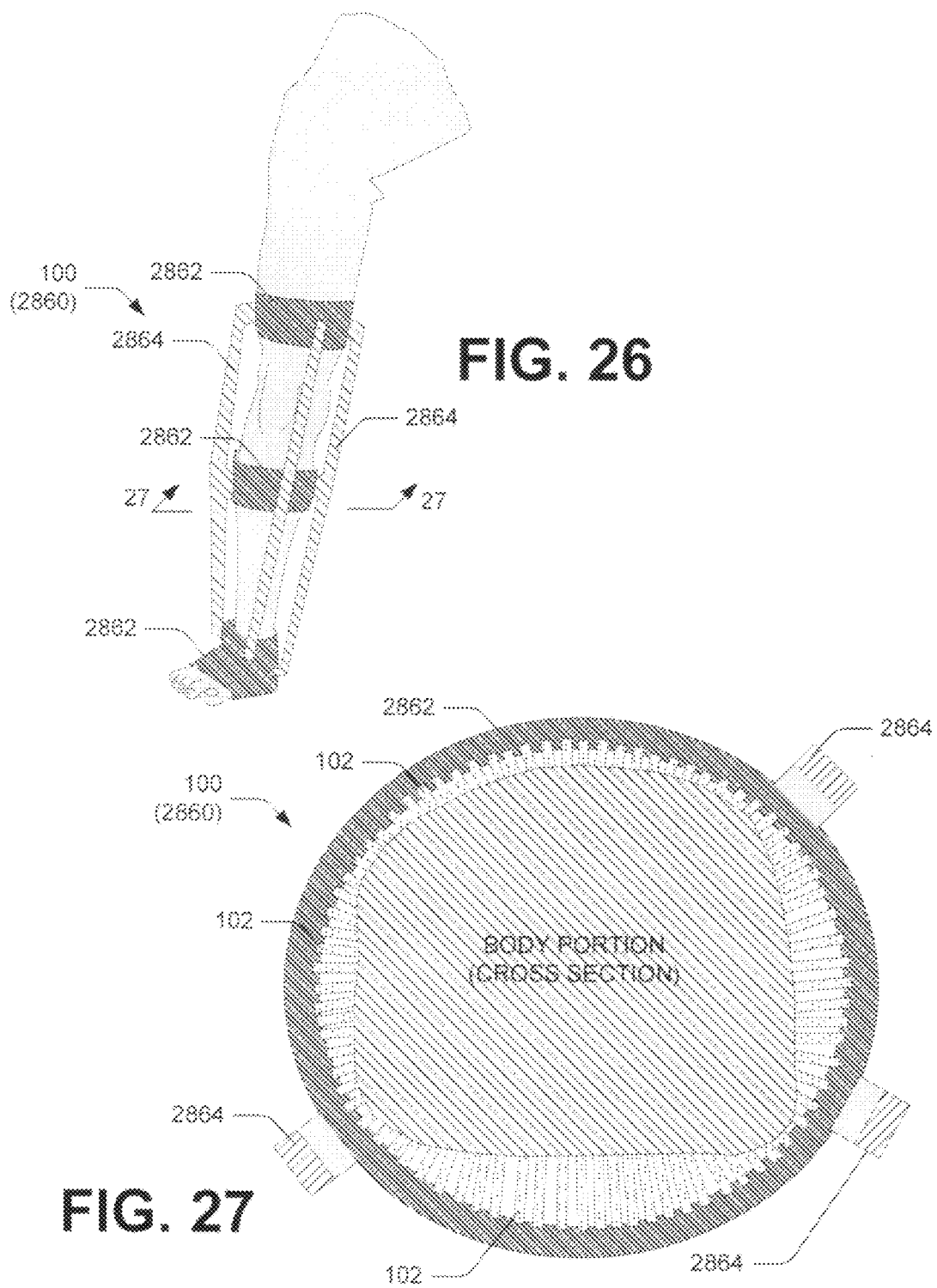

displaceable contouring unit 102

FIG. 43

2000 reducing a pressure differential across one or more supporting surfaces of a body surface of an individual at least partially by displacing at least one displaceable contouring unit to at least partially conform to one or more contours of the body surface of the individual  2002 stabilizing at least the one or more supporting surfaces of the body surface of the individual at least partially with at least one of the at least one displaceable contouring unit  2004

FIG. 44

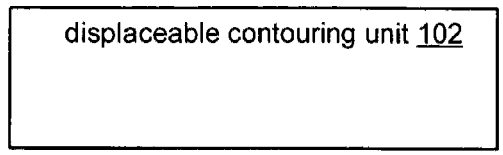

```
relatively displacing at least one displaceable contouring unit with respect to a
medical device portion based at least in part on a contour of an individual to support
at least a portion of the individual while limiting pressure applied to the individual
2102
```

```
stabilizing the at least the portion of the individual by displacing at least one of the at
least one displaceable contouring unit    2104
```

```
limiting pressure differences as applied from multiple ones of the at least one
displaceable contouring unit across the at least the portion of the individual    2106
```

```
providing an access to the individual characterized by an absence of the at least one
displaceable contouring unit    2108
```

FIG. 46

```
┌──────────────────────────────────────┐
│  displaceable contouring unit 102    │
└──────────────────────────────────────┘
```

2200 ⟶    FIG. 47

```
┌──────────────────────────────────────────────────────────────────────────┐
│ displacing at least one displaceable contouring unit to limit pressure   │
│ differences as applied to at least a portion of an individual, wherein   │
│ blood circulation in the individual can be improved at least partially   │
│ in response to the displacing the at least one displaceable contouring   │
│ unit    2202                                                             │
└──────────────────────────────────────────────────────────────────────────┘
```

```
┌──────────────────────────────────────────────────────────────────────────┐
│ positioning an at least a first one of the at least one displaceable     │
│ contouring unit which can limit a pressure being applied to the at least │
│ the portion of the individual by the at least the first one of the at   │
│ least one displaceable contouring unit relative to at least one other   │
│ unit    2204                                                             │
└──────────────────────────────────────────────────────────────────────────┘
```

```
┌──────────────────────────────────────────────────────────────────────────┐
│ positioning the at least one displaceable contouring unit to stabilize  │
│ the at least the portion of the individual    2206                       │
└──────────────────────────────────────────────────────────────────────────┘
```

```
┌──────────────────────────────────────────────────────────────────────────┐
│ positioning the at least one displaceable contouring unit to maintain a │
│ patient in a statically immobile position, thereby limiting pressure    │
│ applied to pressure points or sensitive areas    2208                    │
└──────────────────────────────────────────────────────────────────────────┘
```

```
┌──────────────────────────────────────────────────────────────────────────┐
│ physically separating the at least one of the at least one displaceable │
│ contouring unit from the individual to allow access to at least a       │
│ surface region of the individual    2210                                 │
└──────────────────────────────────────────────────────────────────────────┘
```

```
┌──────────────────────────────────────────────────────────────────────────┐
│ applying a first pressure to the individual in a first direction at     │
│ least partially with a first one of the at least one displaceable       │
│ contouring unit, and applying a second pressure to the individual in a  │
│ second direction at least partially using a second one of the at least  │
│ one displaceable contouring unit, wherein the first direction is        │
│ substantially parallel to the second direction    2212                  │
└──────────────────────────────────────────────────────────────────────────┘
```

| 48a |
|-----|
| 48b | key to FIG. 48

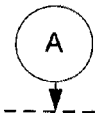

| 48a |
| 48b |
key to FIG. 48 applying a first pressure to the individual in a first direction at least partially with a first one of the at least one displaceable contouring unit, and applying a second pressure to the individual in a second direction at least partially using a second one of the at least one displaceable contouring unit, wherein the first direction is at an angle to the second direction   2214 positioning the at least one displaceable contouring unit relative to a medical displaceable contouring mechanism, wherein the at least one displaceable contouring unit can limit uneven pressure applied between the at least one displaceable contouring unit relative to the at least the portion of the individual   2216 inflating or deflating at least one of the at least one displaceable contouring unit to extend or retract the at least one of the at least one displaceable contouring unit   2218 wherein at least one of the at least one displaceable contouring unit can be deformed to apply a pressure against the individual   2220

FIG. 48b displaceable contouring unit 102

> stabilizing at least part of an individual in a statically immobile position at least partially using displacement of at least one displaceable contouring unit  2302

FIG. 50

> displaceable contouring unit 102

> determining a contour of at least a portion of an individual  2402
>
> relatively displacing at least one displaceable contouring unit to conform at least in part to the contour of the individual, wherein, when the at least one displaceable contouring unit supports the at least the portion of the individual, pressure being applied against the at least the portion of the individual can be limited  2404

FIG. 52

MEDICAL DISPLACEABLE CONTOURING MECHANISM

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 11/503,489, entitled MEDICAL DISPLACEABLE CONTOURING MECHANISM, naming Roderick A. Hyde, Muriel Y. Ishikawa, Edward K. Y. Jung, Eric C. Leuthardt, Royce A. Levien, Robert W. Lord, Mark A. Malamud, Nathan P. Myhrvold, Dennis J. Rivet, John D. Rinaldo, Jr., Michael A. Smith, Clarence T. Tegreene, Lowell L. Wood, Jr., and Victoria Y. H. Wood as inventors, filed 10, Aug. 2006 now U.S. Pat. No. 7,789,086, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/589,317, entitled MEDICAL DISPLACEABLE CONTOURING MECHANISM, naming Roderick A. Hyde, Muriel Y. Ishikawa, Edward K. Y. Jung, Eric C. Leuthardt, Royce A. Levien, Robert W. Lord, Mark A. Malamud, Nathan P. Myhrvold, Dennis J. Rivet, John D. Rinaldo, Jr., Michael A. Smith, Clarence T. Tegreene, Lowell L. Wood, Jr., and Victoria Y. H. Wood as inventors, filed 27, Oct. 2006 now U.S. Pat. No. 7,740,015, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

TECHNICAL FIELD

This disclosure can relate to, but is not limited to, certain embodiments of medical displaceable contouring mechanisms, and/or associated techniques.

BRIEF DESCRIPTION OF THE FIGURES

FIG. 26 shows a diagram of an embodiment of the medical displaceable contouring mechanism that can be configured to at least partially stabilize at least a portion of the individual;

FIG. 27 shows a cross section of the medical displaceable contouring mechanism of FIG. 26;

FIG. 43 is a diagram of one embodiment of the at least one displaceable contouring unit;

FIG. 44 is a block diagram of a high-level flow chart of one embodiment of one embodiment of a medical differential pressure reduction technique such as can be performed by the at least one displaceable contouring unit of FIG. 43;

FIG. 45 is a diagram of another embodiment of the at least one displaceable contouring unit;

FIG. 46 is a block diagram of a high-level flow chart of another embodiment of one embodiment of a medical differential pressure reduction technique such as can be performed by the at least one displaceable contouring unit of FIG. 45;

FIG. 47 is a diagram of another embodiment of the at least one displaceable contouring unit;

FIG. 48 (including FIGS. 48a and 48b) is a block diagram of a high-level flow chart of another embodiment of one embodiment of a medical differential pressure reduction technique such as can be performed by the at least one displaceable contouring unit of FIG. 47;

FIG. 49 is a diagram of another embodiment of the at least one displaceable contouring unit;

FIG. 50 is a block diagram of a high-level flow chart of another embodiment of one embodiment of a medical differential pressure reduction technique such as can be performed by the at least one displaceable contouring unit of FIG. 49;

FIG. 51 is a diagram of another embodiment of the at least one displaceable contouring unit; and FIG. 52 is a block diagram of a high-level flow chart of another embodiment of one embodiment of a medical differential pressure reduction technique such as can be performed by the at least one displaceable contouring unit of FIG. 51.

DETAILED DESCRIPTION

At least certain portions of the text of this disclosure (e.g., claims and/or detailed description and/or drawings as set forth herein) describe a medical displaceable contouring mechanism that can be configured to reduce a pressure differential between a number of support mechanisms as included therein, as set forth by various different claim groupings and/or various different applications. Although, for sake of convenience and understanding, the detailed description can include section headings that may generally track various different concepts associated with claims or general concepts contained therein, and is not intended to limit the scope of the invention as set forth by each particular claim. It is to be understood that equalizing the pressure differential across the support mechanisms for the various applications or portions thereof thereby can appear throughout the text and/or drawings at one or more locations, irrespective of the section headings.

1. CERTAIN EMBODIMENTS OF THE MEDICAL DISPLACEABLE CONTOURING MECHANISM

Figure 1:
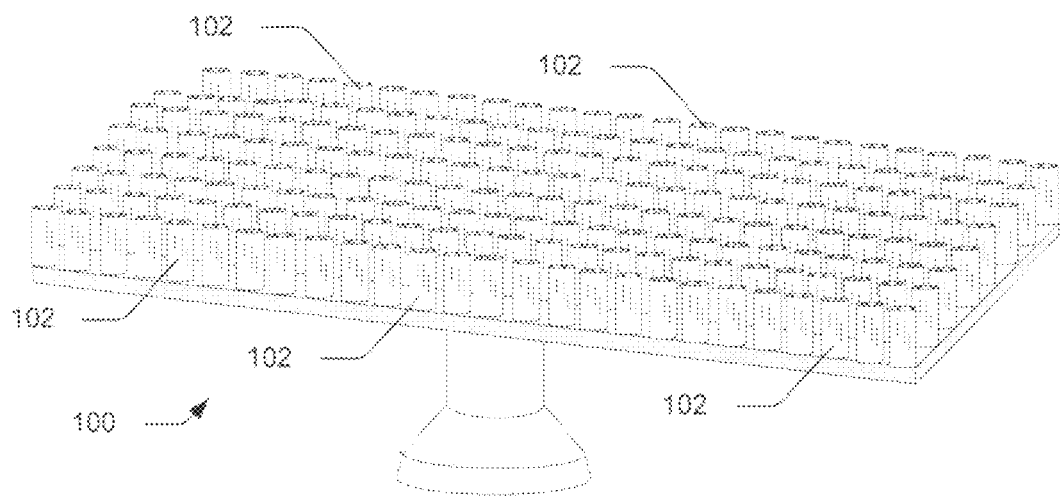
FIG. 1 is a diagram of one embodiment of a medical displaceable contouring mechanism that can include at least one displaceable contouring unit(s)
Figure 2:
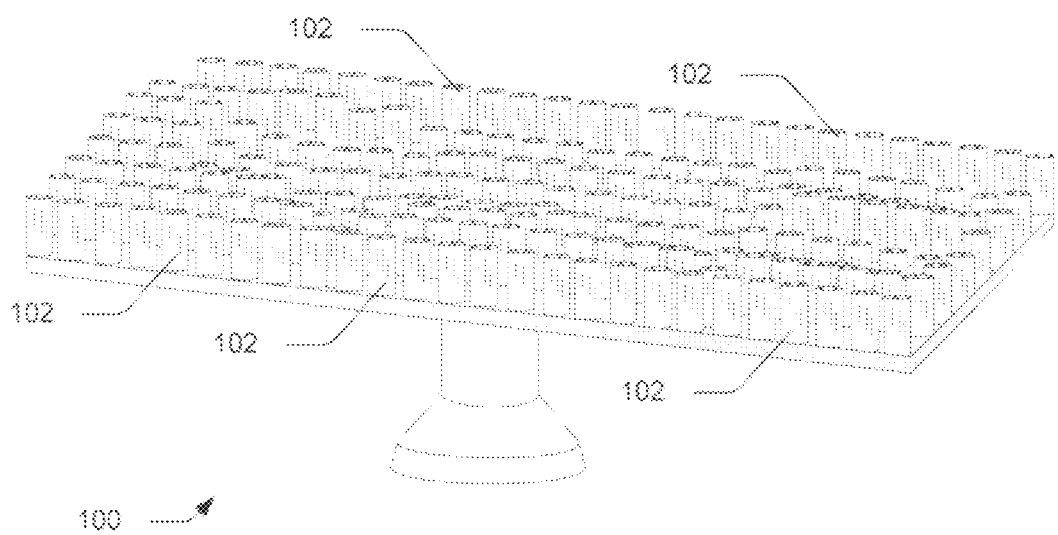
FIG. 2 is a diagram of the medical displaceable contouring mechanism of FIG. 1 with certain ones of the displaceable contouring unit(s) being displaced.
Figure 3:
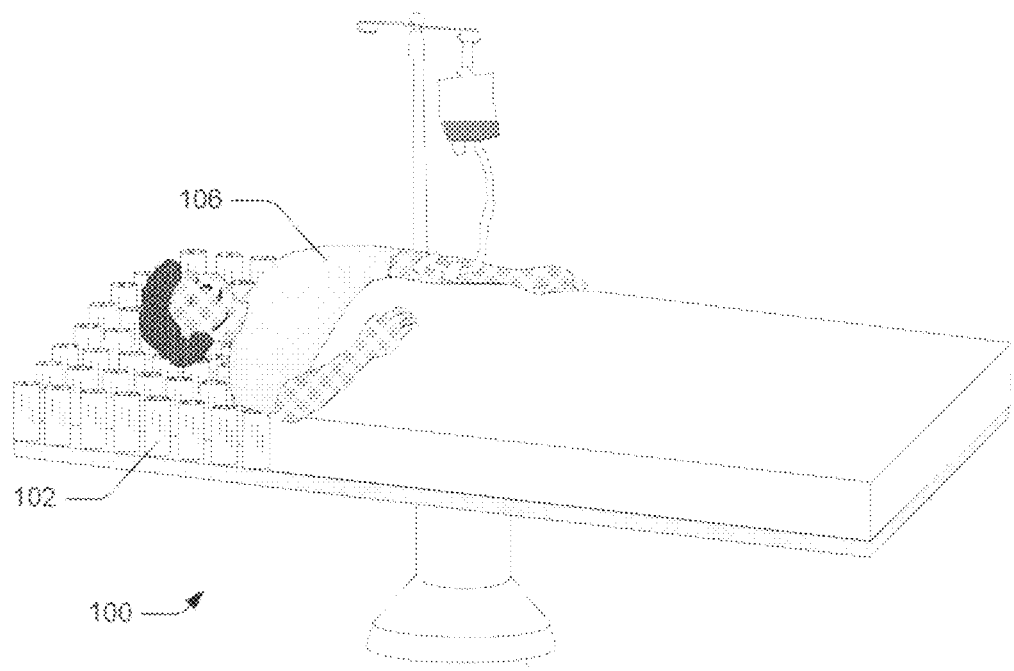
FIG. 3 is a diagram of the medical displaceable contouring mechanism of FIG. 1 or 2 with an individual (e.g., a person or animal) resting thereupon.

This disclosure describes a number of embodiments of, and a number of aspects of, certain embodiments of a medical displaceable contouring mechanism 100 (such as illustrated in FIGS. 1 to 3) that can be configured to provide support for an individual 106, which may be a human or alternatively an animal or living organism. Certain applications of the different embodiments of the medical displaceable contouring mechanism 100 may be directed to clinical applications, such as for patients in hospitals, clinics, nursing homes, doctor's offices, etc., while other applications may be more non-clinical or even home-care environments. Certain embodiments of the medical displaceable contouring mechanism 100, as described with respect to FIGS. 1 to 3 and at other locations throughout the disclosure, can be configured to include and/or be associated with a least one (and typically a number of) displaceable contouring unit(s) 102 situated thereupon.

Certain embodiments of the at least one displaceable contouring units 102 can be configured to be displaceable relative to an individual 106, and thereby can be operationally configured to reduce differences in pressure applied between different ones of the displaceable contouring units 102. By reducing differences in pressure as being applied to at least portions of the individual 106, certain embodiments of the medical displaceable contouring mechanism 100 can be configured to limit the maximum pressure as applied to any one location, limit the formation of bed sores, blisters, limit reduced blood circulation, etc. Bedsores, ulcers, and the like may result when individuals are maintained in conventional operating tables, conventional hospital beds, wheelchairs, stretchers, conventional nursing home beds, as well as other conventional beds particularly for long durations.

Certain embodiments of the medical displaceable contouring mechanism 100 as described in this disclosure can be applied to a variety of applications. For example, certain embodiments of the medical displaceable contouring mechanism 100 can be applied to support mechanisms such as operating tables, hospital beds, etc. Certain embodiments of the medical displaceable contouring mechanism can be applied to stabilizing mechanisms such as to maintain a position of at least a portion of the individual, such as with a traction mechanism, body stabilizing mechanism, a cast-type stabilizing mechanism, etc.

Certain embodiments of the medical displaceable contouring mechanism 100 and/or the at least one displaceable contouring units 102 may be configured, designed, operated, and/or configured to perform a variety of operations as described in this disclosure such as, but not limited to, supportive, pressure differential reduction, and/or stabilization functions. Within this disclosure, the term "displaceable contouring," such as included in the medical displaceable contouring mechanism 100, can, depending on context, pertain to the ability to displace at least a portion thereof (e.g., the at least one displaceable contouring units 102) to approximate or follow the contour of the individual. The term "displaceable contouring", such as included in the medical displaceable contouring mechanism 100, can also, depending on context, indicate reducing pressure differential across only certain displaceable contouring unit(s) 102 that are being used to support at least a portion of the individual 106 (such as to limit pressure points, and other pressure-related situations as described in this disclosure). The term "displaceable contouring," such as allowed by certain displaceable contour unit(s) included in the medical displaceable contouring mechanism 100, can, depending on context, be used, for example, to stabilize at least a portion of the individual 106 (e.g., a broken leg, etc.). In certain cases when the medical displaceable contouring mechanism stabilizes the individual, it may or may not additionally support the individual. In those stabilization instances where the displaceable contouring unit(s) 102 do not support a portion of the individual, the displaceable contouring unit(s) 102 thereby may not apply pressure such as to be supportive to the individual, and may not apply a reduced pressure differential against the individual 106, for example.

Certain embodiments of the medical displaceable contouring mechanism 100 can include a number of the at least one displaceable contouring units 102 that can provide support for the individual 106 substantially in a single direction, as described with respect to FIGS. 1 to 3. For example, at least some of the displaceable contouring units 102 can relatively move substantially up-and-down, through a variety of angles, into a variety of positions, etc., as described with respect to certain ones of the figures, to support and/or stabilize the individual 106. By comparison, certain embodiments of the at least one displaceable contouring units 102 can be configured to support at least a portion of the individual 106 along one, two, or three substantially orthogonal axes, as appropriate. At least certain ones of the at least one medical displaceable contouring mechanism 100 can be either configured as an integral portion of the medical displaceable contouring mechanism 100, or alternatively as an add-on or accessory such as can be secured to the medical displaceable contouring mechanism 100 later (such as an add-on such as a cast, a traction mechanism, another body part stabilizer, an add-on oxygen mask or gas mask, a ventilator, an add-on medicator, etc.) to existing operating tables, hospital beds, cots, stretchers, tables, or the like. Since certain embodiments of the at least one displaceable contouring unit(s) 102 can be configured for flexibility, certain ones can even be set on top of an existing rigid platform, table, surface, etc.

Figure 4:
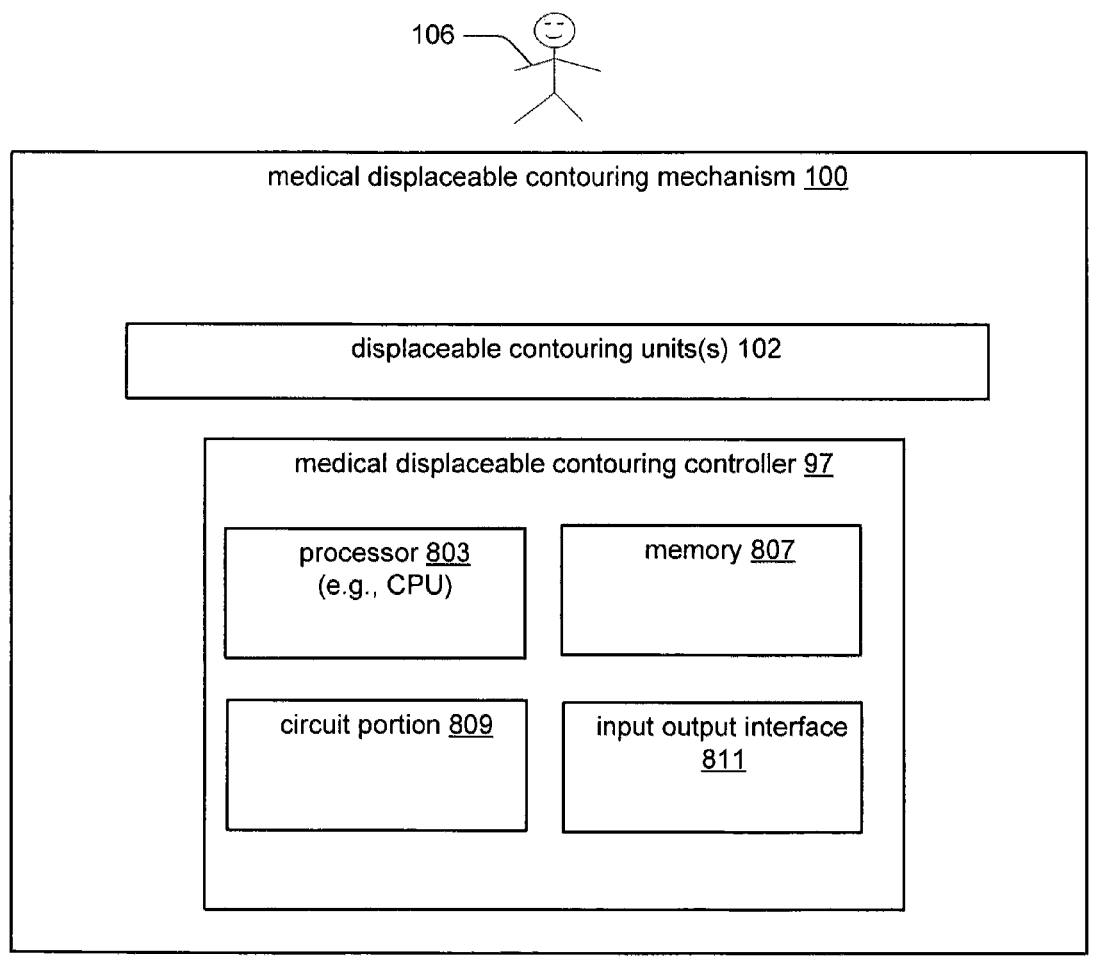
FIG. 4 is a block diagram of another embodiment of the medical displaceable contouring mechanism.
Figure 6:
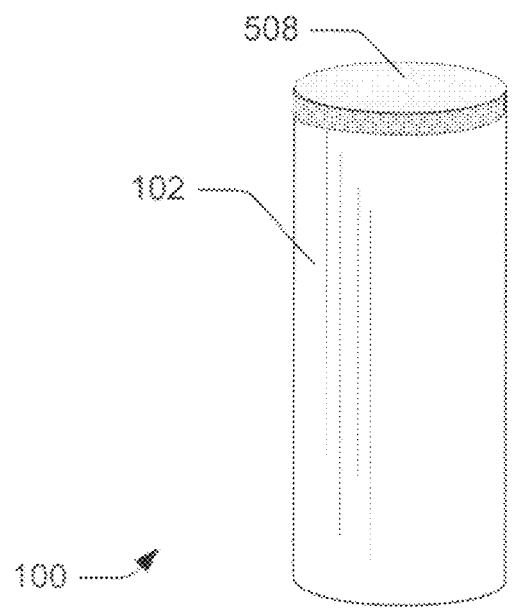
FIG. 6 is a diagram of another embodiment of the displaceable contouring unit(s)

Certain embodiments of the medical displaceable contouring mechanism 100 can involve the at least one medical displaceable contouring controller 97, as described in this disclosure with respect to FIG. 4. Certain embodiments of the at least one medical displaceable contouring controller 97, for example, can involve displacing, positioning, actuating, moving, and/or otherwise utilizing the at least one displaceable contouring unit(s), as described in this disclosure. In addition, certain embodiments of the medical displaceable contouring mechanism 100, or other frames or components associated therewith, can be bent, rotated, displaced, or otherwise utilized to support certain embodiments of the at least one displaceable contouring unit(s) 102, as described in this disclosure. The functionality of certain embodiments of the medical displaceable contouring mechanism 100 can thereby be largely determined or effected by the medical displaceable contouring controller 97.

Consider, for example, that certain conventional operating tables, hospital beds, stretchers, etc. can be bent, contoured, rotated, repositioned, etc. based at least in part on the contour of at least a part of the individual, as well as how the individual is to be supported and/or maintained. For example, during certain back operations, certain patients (and/or their physicians) may preferably have the individual lie face-down on an operating table such that the individual may be positioned to curve or be bent downwardly (e.g., at the waist), as well as being able to be positioned in a variety of configurations. Additionally, it may be desired to reposition or roll the patient, depending on the treatment or operation. Certain embodiments of the medical displaceable contouring mechanism 100 can also thereby be configured in a suitable shape or contour (or whose shape or contour may be altered) as to suit the particular individual patient, physician, medical personnel, or other. Certain embodiments of the medical displaceable contouring mechanism 100 can thereby provide a desirable positioning of the individual, while also providing for a suitable distribution of pressure, stabilization, and/or other movements, positioning, and/or treatments to the individual as described in this disclosure.

Certain embodiments of the medical displaceable contouring mechanism 100 can thereby be configured to be movable, bendable, and/or rotatable, etc. such as by providing a framework and/or allowing the displaceable contouring unit(s) 102 that can be displaced. Alternately, certain embodiments of the displaceable contouring unit(s) 102 can be displaced relative to each other (e.g., without a frame member) to establish a desired configuration or contour. In the instance of those embodiments of the medical displaceable contouring mechanism 100 that are being utilized as described in this disclosure, it may be desirable to translate, move, rotate, or otherwise reposition the mechanism such that it may become necessary to position, support, and/or stabilize the individual 106, such as during an operation or procedure. Certain embodiments of the medical displaceable contouring mechanism 100 can thereby be configured to operate and/or be displaced in combination with another medical displaceable contouring mechanism. For example, during certain operations, procedures, scans, x-rays, etc., it may be desirable to limit motion by the individual 106. As such, one medical displaceable contouring mechanism 100 can be situated along the back (posterior) of the individual 106; and another one can be situated substantially across the front (anterior) of the individual 106 as described with respect to FIGS. 18 & 19. This sandwiching of the individual between two or more medical displaceable contouring mechanisms 100 can thereby limit undesirable motion by the individual 106 (whether the individual is conscious or unconscious). Additional medical displacement contouring mechanisms 100 can be provided to position, support, and/or stabilize at least a portion of the body of the individual, as well as to provide the desired medication and/or input/output from the individual as described in this disclosure. Similarly, certain embodiments of the medical displaceable contouring mechanism 100 can be configured to position or move the individual in a wide variety of accessible locations to facilitate certain operations, scans, and/or procedures.

Certain embodiments of the medical displaceable contouring mechanism 100 can include one or more displaceable contouring unit(s) 102 that can be devoted entirely or in part to medication (e.g., securing a drug injection mechanism, such as a syringe), anesthesiology (e.g., holding a gas mask in place), and/or other accessories. For example, certain embodiments of the one or more displaceable contouring unit(s) 102 could maintain glasses in a position relative to the individual, or alternately provide a video display device, a computer, or other mechanism in a position that could be actuated, used, or viewed by the individual. As such, certain embodiments of the displaceable contouring unit(s) 102 could be configured such that an individual with only slight motion may be able to access a considerable amount by pressing or displacing certain actuators or mechanisms using varied mechanisms and/or techniques.

Certain embodiments of the medical displaceable contouring mechanism 100 can be configurable as an operating table, a hospital bed, a stretcher, etc. Other embodiments of the medical displaceable contouring mechanism 100 can be configured as an accessory device such as a support or stabilizing unit, a traction mechanism, a bedpan, etc. Still other embodiments of the medical displaceable contouring mechanism 100 can be configured as a separate unit such as a body part stabilizer (which can be configured to operate as a cast for example).

The embodiment of the medical displaceable contouring mechanism 100 of FIG. 1 can include, but is not limited to, one or more displaceable contouring unit(s) 102, at least certain ones which can be displaced with respect to the medical displaceable contouring mechanism 100 as described in this disclosure. The at least one displaceable contouring unit(s) can be configured, as described in this disclosure, to be displaced as described with respect to FIG. 2 to substantially conform to the contour of the individual 106. Certain aspects of the positioning of at least some of the one or more displaceable contouring unit(s) 102 can be selected based at least in part on at least one contour or shape of the individual, based on where or how the individual is to be supported. Thereby, when the individual 106 sits or rests in contact with respect to the medical displaceable contouring mechanism 100, as described with respect to FIG. 3. The pressure being applied to the pressure points situated at certain portions of the outside of the individual 106 (e.g., the skin) can thereby be reduced and/or distributed over a number of the contouring unit(s) 102, effectively limiting the severity and/or the effects of the pressure points. Such pressure-point reduction can also act to enhance blood circulation at certain portions of the individual 106.

Certain embodiments of the medical displaceable contouring mechanism 100, as described this disclosure, can include only the at least one displaceable contouring unit(s) 102 to support the individual 106. By comparison, certain embodiments of the medical displaceable contouring mechanism 100 can include a number of structures, portions, pillows, cast portions, traction mechanisms, individual stabilizing devices, support mechanisms, etc. in addition to the at least one displaceable contouring unit(s) 102. For example, certain embodiments of the medical displaceable contouring mechanism 100 that can be configured as a hospital bed, for example, may involve a portion thereof being configured or shaped to appear similar as a hospital bed to support the individual. Another portion of the medical displaceable contouring mechanism 100 therefore can be configured to include the at least one displaceable contouring unit(s) 102 as described in this disclosure. As such, certain embodiments of the medical displaceable contouring mechanism 100 can be viewed as and may operate as a modular unit, in which appropriate portions, access portions, openings, support regions, add-ons, functional mechanisms, etc. are formed therein depending upon the particulars of the individual 106, the operation, the physician, etc.

There may be a variety of additional techniques or applications for certain embodiments of the displaceable contouring unit 102, as described in this disclosure. For example, certain embodiments of the displaceable contouring unit 102 could slowly rise or fall, thereby relatively altering pressure and/or oscillating, vibrating, and/or providing a desired contour, support, or stabilizer, near or at a given location. Certain embodiments of the displaceable contouring unit 102 could thereby act as a localized thumper such as may generally be understood by pulmonary or other surgical practitioners. For instance, certain individuals such as patients having a considerable amount of pulmonary secretions need what is referred to among those skilled in surgery as a "chest pulmonary toilet," as generally understood by surgeons and physicians. Certain embodiments of the displaceable contouring unit 102 can thereby operate to reposition the individual such as by rolling the individual or patient on their side or front either by the physician or other medical personnel, or perhaps with assistance with certain embodiments of the displaceable contouring unit 102.

As the individual or patient is situated on their front or side, either the physician or other medical personnel can thereupon "whack" their cupped hand(s) at a fast rate on the back of the individual or patient for an extended duration (e.g., 10-20 minutes) so that it will break up and clear accumulated secretions in the airway of the patient to be suctioned out via their in endotracheal tube, or certain embodiments of the displaceable contouring unit 102 can be configured to apply a similar whacking action on the back of the individual or patient. Certain embodiments of the displaceable contouring unit 102 could be configured to apply a similar, and highly controlled, application of force to the individual 106 without the physician or other medical personnel having to concentrate on applying force to the individual. For instance, certain embodiments of the displaceable contouring unit 102 can be configured based on the physician or medical personnel determining a region to percuss, and to perform it without excessive patient mobilization and/or need for dedicated medical or physician support.

Certain embodiments of the medical displaceable contouring mechanism 100 can be configured to limit pressure induced nerve injuries. Some type of pressure induced nerve injuries may occur in the setting of an operation where a patient is kept very rigidly immobile and sometimes is laying on some nerve which gets a pressure induced neuropraxia. As such, certain embodiments of the medical displaceable contouring mechanism 100 can be configured to limit motion of the individual by "contouring" to the shape of at least a part of the individual while limiting the pressure applied to the pressure points and other surface areas of the individual. In certain instances, such nerve damage resulting from pressure induced nerve injuries is often temporary, but can occasionally be permanent.

Certain embodiments of the medical displaceable contouring mechanism 100 can be configured to allow the individual 106 (such as a human and/or an animal), to be positioned into a desired position such as may be appropriate. For example, certain types of operations or procedures can be performed using certain embodiments of the medical displaceable contouring mechanism 100 in which the individual 106 can be situated in a supine position, a prone position, a lateral position, and/or another suitable or desirable position. During certain operations, procedures, etc., it may be desired to move the individual 106 on the operating table. Certain embodiments of the at least one displaceable contouring unit(s) 102 in the medical displaceable contouring mechanism 100 can thereby be displaced, moved, or adjusted to allow for such positioning of the individual 106, either by itself or in combination with equalizing pressure applied across at least portions of the individual 106. Alternatively, certain frame members that can secure at least one of the displaceable contouring unit(s) can be displaced, moved, or adjusted.

Figure 18:
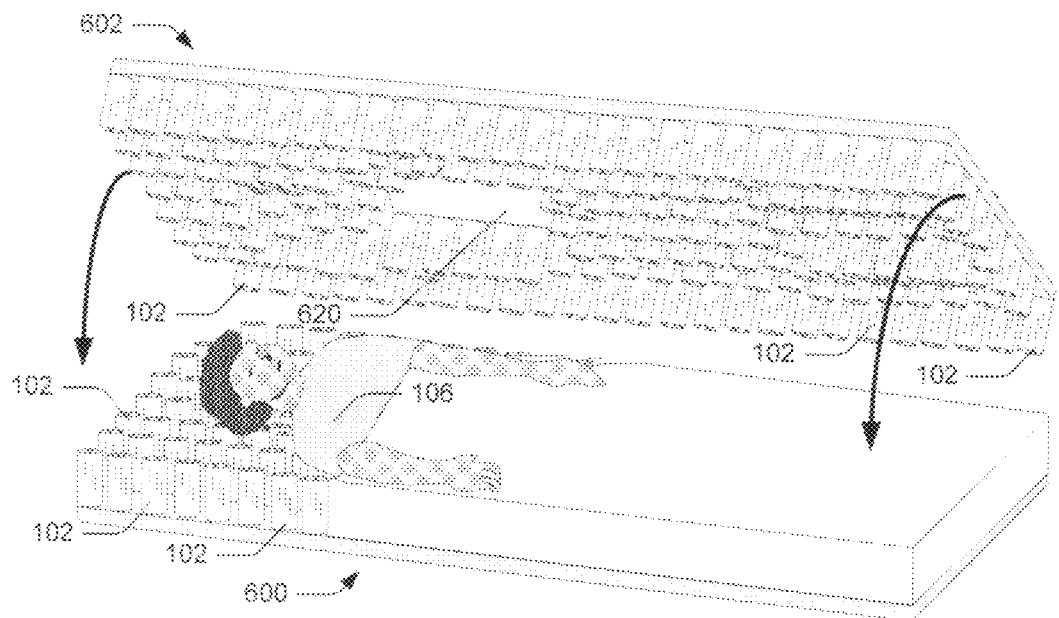
FIG. 18 is a diagram of another embodiment of the displaceable contouring unit as applied to an individual in its open position.
Figure 19:
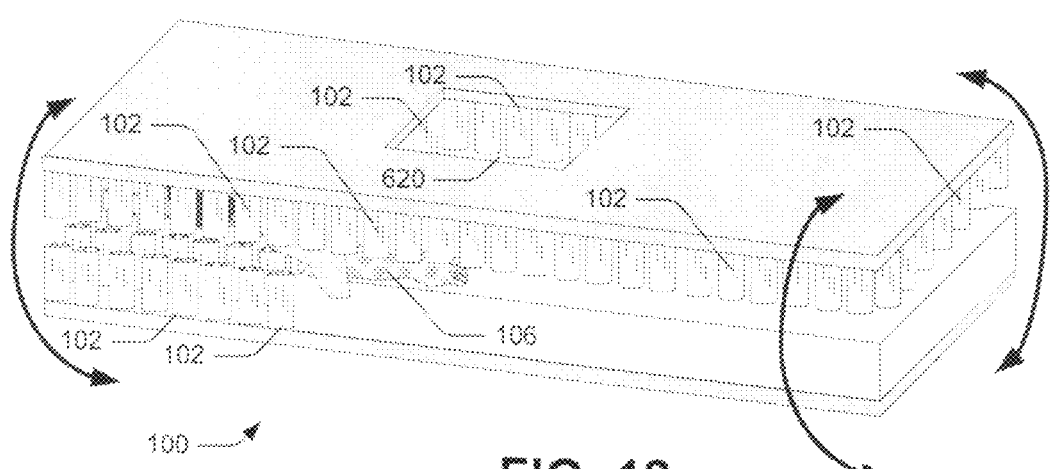
FIG. 19 is a diagram of the embodiment of the displaceable contouring unit of FIG. 18 in its closed position.

Certain embodiments of the medical displaceable contouring mechanism 100 can be removed, or moved, to create an access region 620 as described with respect to FIGS. 18 and 19, to thereby provide access to at least certain portions of the individual 106. The configuration and/or structure of the access region 620 can vary depending, for example, on the individual 106, the operation or procedure, and techniques of the physician or medical personnel, structure of the medical displaceable contouring mechanism 100, etc. For example, certain embodiments of the medical displaceable contouring mechanism 100 can be configured as to provide physicians or other medical personnel access to those areas that they are operating on and/or treating as desired. As such, certain embodiments of the at least one displaceable contouring unit(s) 102 (as well as particular framework, supporting mechanisms, etc.) of the medical displaceable contouring mechanism 100 can be moved, shifted, rotated, displaced, or otherwise removed from the area which the surgeon or medical personnel is attempting to access.

Certain embodiments of the medical displaceable contouring mechanism 100 can include portions that allow for maintaining or adjusting relative positioning between particular ones of the at least one displaceable contouring unit(s) (even if certain ones thereof have been removed, added, or adjusted). This disclosure describes a number of embodiments of the medical displaceable contouring mechanism 100 that involves certain ones of the at least one displaceable contouring unit(s) being removed therefrom such as to provide access to at least certain portions of the individual.

The particular use of a number of embodiments of the medical displaceable contouring mechanism 100 is intended to be illustrative in nature but not limiting in scope. Certain ones of the concepts as described in the embodiments as described in this disclosure can also be applied to a number of other applications. Certain embodiments of the medical displaceable contouring mechanism 100 can include for example, but are not limited to: an operating table, a medical bed, a hospital bed, an ambulance bed, a stretcher, or even a regular bed, a chair, a sofa, or other piece of furniture, etc. Certain embodiments of the medical displaceable contouring mechanism 100, however, are particularly suited to hospital, operating room, nursing home, in-home care, and other clinical environments in which the formation of bed sores, potential injury to a portion of the individual 106, and/or desire to limit application of excessive pressures to injured portions of the individual 106 may be desired.

Examples of body parts that can be supported by certain embodiments of the medical displaceable contouring mechanism 100 in such a manner as to limit excessive pressures can include, but are not limited to: an entire body as well as the components thereof, an arm, leg, torso, head, spine, etc. Limiting pressure differential as applied to certain body parts of the individual 106, may alternatively tend to equalize support for different body parts can be provided in combination or separately using certain embodiments of the medical displaceable contouring mechanism 100. Certain embodiments of the medical displaceable contouring mechanism 100 can also be configured to stabilize a body part or the entire body of the individual 106, and as such can act in a similar manner, though perhaps to be less rigid and/or more comfortable than, for example, a cast or other type of pressure equalizing support.

By reducing the pressure applied by certain embodiments of the medical displaceable contouring mechanism 100 as applied to certain individuals 106 such as humans or animals, certain ones of the individuals 106 can experience improved blood circulation throughout their body, limited pressure points, improved rest, improved sleep, etc. at least partially in response to displacement of the at least one displaceable contouring unit(s) 102 that can upon displacement become more closely contoured to at least parts of the individual 106 to more evenly support at least parts of the individual.

Certain embodiments of the medical displaceable contouring mechanism 100 can be configured, and/or intended, for a variety of applications. For example, certain embodiments of the medical displaceable contouring mechanism 100 can be utilized within a hospital, either for in-patient, out-patient, operating room, or other applications. Certain embodiments of the medical displaceable contouring mechanism can be applied to ambulance, emergency medical treatment, translatory, air-transfer, medical evacuation, ski patrol, disaster, or other such applications. Certain embodiments of the medical displaceable contouring mechanism can be applied to home or office (e.g., doctor's office) applications, either for individuals 106 that are being home-cared, or even those with injuries or healthy individuals 106 who can use some treatment.

Certain embodiments of the medical displaceable contouring mechanism 100 can be customized based upon such factors that can include, but are not limited to: the individual's 106 injury; the individual's size, weight, height, shape, etc.; the physician's or other medical personnel's treatment technique; the individual's treatment regimen; and those particular treatments or activities that may occur in the medical displaceable contouring mechanism 100. Certain embodiments of the medical displaceable contouring mechanism 100, for example, can be configured for a particular patient and injury and/or treatment; and the patient can thereupon also be transferred, treated, maintained, etc. in certain embodiments of the medical displaceable contouring mechanism. Consider, for example, the case of a remote accident or injury, certain embodiments of the medical displaceable contouring mechanism 100 can be formed are positioned relative to the individual 106 at the site of the accident or injury. The individual 106 can thereupon be transferred within the ambulance or other vehicle while being stabilized by the medical displaceable contouring mechanism. The individual 106 can thereupon be transferred to a hospital, doctor's office, etc. while being stabilized by certain embodiments of the adaptive medial displaceable contouring mechanism 100. If the physician or other medical personnel determines that the medical displaceable contouring mechanism 100 should be removed, changed, modified, replaced, and/or altered, they can do so at their desire, leisure, or as they consider appropriate. Removal and/or displacement of at least certain ones of the displaceable contour unit(s) 102 relative to certain embodiments of the medical displaceable contouring mechanism 100 can allow for relatively easy cleaning of either the displaceable contour unit(s) and/or the medial displaceable contouring mechanism, which may be particularly desirable for bedridden, intensive care, or other individuals.

As described in this disclosure, certain embodiments of the at least one displaceable contouring unit(s) 102 can support or stabilize an instantaneous under-side of a portion of the individual, while other displaceable contouring unit(s) 102 can support or stabilize an instantaneous upper surface of at least a portion of the individual. Those displaceable contouring unit(s) 102 that support the instantaneous under-side of at least a portion of the individual will have to apply greater force or pressure to counteract gravity as applied to the individual. Those displaceable contouring unit(s) 102 that support the instantaneous upper surface of the individual 106 will have to apply a lesser force or pressure since gravity reduces the force applied thereto. As such, within this disclosure, the references to a particular portion can also be segmented considering whether each particular portion is instantaneously above, instantaneously below, or instantaneously on the side of the individual. Certain embodiments of the medical displaceable contouring controller 97, as described in this disclosure can control the relative positioning of the displaceable contour unit(s) 102 such as to compensate for gravity, acceleration, and/or force as applied to the individual. As such, when the individual is repositioned, such as being turned over in an operating room, certain ones of the at least one displaceable contouring unit(s) 102 may have to be re-adjusted as appropriate to support or stabilize at least a portion of the individual.

There may be a number of reasons why it may not be desirable to apply equal pressure from the at least one displaceable contouring unit(s) 102 of the medical displaceable contouring mechanism 100. For example, certain ones of the at least one displaceable contouring unit(s) 102 may be situated under and/or supporting a comparatively lighter portion of the individual 106, such as an arm, while other ones of the at least one displaceable contouring unit(s) 102 may be situated under and/or supporting a comparatively heavier or denser portion of the individual 106, such as a torso. As such, it may be desired to limit pressure as applied from each of the at least one displaceable contouring units that may support a similar weight of the individual 106 considering the different portions of the individual.

Additionally, certain embodiments of the at least one displaceable contouring unit(s) that are not situated under certain portion(s) of the individual 106 can be operated to retract, extend, and/or be displaceable, and thereby be situated to apply a desirable force or pressure to the individual, or some other pressure characteristic based on the desire of the physician, the individual 106, the designer, etc. For example, certain embodiments of the at least one displaceable contouring unit(s) 102 can extend, such as to be situated laterally relative to the individual, and also perhaps extending higher than or above at least a portion of the individual 106. For example, the displaceable contouring unit(s) 102, when extended, can extend to a height, position, or level sufficient to limit travel (e.g., in a lateral or other direction) of the individual 106 past the extended ones of the at least one displaceable contouring unit(s) 102 of the medical displaceable contouring mechanism 100.

As described in this disclosure, the medical displaceable contouring mechanism 100 could be configured to reduce pressure differential between multiple displaceable contouring unit(s) depending on the operation thereof, but perhaps not others. Certain embodiments of the at least one displaceable contouring unit(s) could be configured to increase, decrease, vary, modulate, or otherwise change the pressure to various sites as compared to other ones of the displaceable contouring unit(s). Certain embodiments of the displaceable contour unit(s) 102 can thereby be used as a supporting element and/or a stabilizing element by repositioning it, or other, adjacent units.

By configuring certain embodiments of the at least one displaceable contouring unit(s) 102 to apply substantially similar pressure to certain regions across the individual 106, the contour of certain embodiments of the at least one displaceable contouring unit(s) 102 (e.g., at its upper surface) should approximate the corresponding contour of the individual 106. As such, certain embodiments of the medical displaceable contouring mechanism 100 can be configured to position its at least one displaceable contouring unit(s) 102 into a position utilizing the at least one of a number of the described mechanisms such that its outer contour closely approximates a mating contour of the individual 106. As such, certain embodiments of the medical displaceable contouring mechanism 100 can include a contour having a shape that proximally mirrors the surface of the individual 106 at that location.

As described in this disclosure, certain embodiments of the medical displaceable contouring mechanism 100 can be removed, altered, reconfigured, etc. to, for example, allow the physician or other medical personnel to perform the desired operation. For example, consider that the individual 106 is undergoing heart surgery or other thoracic surgery, it may be likely that those portions of the at least one displaceable contouring unit 102 of the medical displaceable contouring mechanism 100 that are situated over the individual's chest would be removed or moved to provide suitable access. Removing (or not applying) a sufficient number of the at least one displaceable contouring units 102 can thereby facilitate suitable and generally understood operating room techniques, hospital techniques, etc. as can thereupon be applied to the individual 106.

Such displaceable contouring between different ones of the at least one displaceable contouring unit(s) 102 can have the effect of limiting the pressure that may be applied to particular portion(s) of the individual 106. As such, protruding portions of the anatomy of the individual 106 (e.g., the face or eyes, genitalia, wounds, women's breasts, injury locations, etc.) such as may experience considerably higher pressure, pain, or even injury as compared to other portions of the anatomy when the individual is situated on conventional operating tables, hospital beds, etc.; by comparison, the at least one displaceable contouring unit(s) 102 may be positioned and/or displaced such as to provide a shape approximately conforming to the contour of the individual 106 and/or sensitive parts of the individual.

Certain areas of the individual 106 that may become pressure points when using certain conventional operating tables and/or beds, which may, instead, with certain embodiments of the medical displaceable contouring mechanism 100, experience considerably reduced and/or distributed pressure at particular pressure locations. By reducing or distributing the pressure more uniformly across certain portions, body surfaces, and/or surface locations of the individual 106, in certain cases the blood circulation can be improved across at least portions of the individual as well as "downstream" circulatory portions of the individual. While this disclosure has described certain circulatory deficiencies in the individual 106 relating to blood, blood components, etc.; is also envisioned that certain embodiments of the medical displaceable contouring mechanism 100 can also enhance other fluid circulatory situations within the individual, such as lymph, medication, applied medications or minerals, urine, saline, etc. therefore, by equalizing the pressure across different portions of the individual 106, fewer places on the anatomy of the individual 106 may experience a reduced blood flow or other circulatory problems, and/or the associated formation of bed sores, produced circulatory problems, blisters, etc. by utilizing certain embodiments of the medical displaceable contouring mechanism 100.

There can be a variety of mechanisms that can be utilized to displace, transfer, rotate, move, or otherwise situate certain embodiments of the at least one displaceable contouring unit(s) 102, as described in this disclosure. Moving or positioning certain embodiments of the at least one displaceable contouring unit(s) 102 can thereby be utilized to move, displace, reposition, reconfigure, or otherwise resituate the individual. Certain embodiments of the at least one displaceable contouring unit(s) can form a variety of shapes, configurations, provide a variety of operating parameters, utilize a variety of extending mechanisms, etc., as described in this disclosure, which these examples are intended be illustrative in nature but not limiting in scope. Certain embodiments of the medical displaceable contouring mechanism 100 can be moved, translated, deflated, etc. as desired by the physician and/or other treating personnel.

Consider, for example, a doctor treating a bone injury patient during their rounds. With conventional casts, traction, and/or other stabilizing mechanisms, for example, it may be difficult or expensive to examine the particular site of an injury, a wound, a broken bone, an ulcer, an abrasion, etc. which may be situated underneath the cast and/or in traction, for example. It would be impractical, for example, for a physician or other medical personnel to remove a conventional cast each time the physician wanted to thoroughly examine and/or cleanse an injury location for a broken bone and/or a wound.

Certain embodiments of the medical displaceable contouring mechanism that is acting as a support or stabilizer can, for example, be temporarily removed and/or positioned to allow the doctor, emergency technician, ambulance driver, ski patrol, nurse, or other person to examine the wound or injury. The spacing of certain embodiments of the displaceable contouring unit 102 can be sufficiently reduced as to permit removal, cleaning, and/or other such operations while allowing the other displaceable contour unit(s) 102 to maintain the support and/or stabilization. Certain embodiments of the medical displaceable contouring mechanism 100 can also be configured to limit its contacting or overlying of wounds, bedsores, or injuries, etc. Limiting the contacting or overlying of the portions of the medical displaceable contouring mechanism 100 to wounds, bedsores, or injuries, etc. can thereby increase the exposure of the wounds, bedsores, or injuries, etc. to air that may improve the healing. Limiting the contacting or overlying of the portions of the medical displaceable contouring mechanism 100 to wounds, bedsores, or injuries, etc. can also limit the exposure of the wounds, bedsores, or injuries, etc. to foreign bodies (such as portions of the cast, etc.), that may hinder healing.

Certain embodiments of the medical displaceable contouring mechanism 100 may be adaptive to thereby reduce pressure differentials appropriately. It may also be possible for certain embodiments to be de-assembled and/or stored in an unassembled fashion to, e.g., save space. Consider, for example, certain embodiments of the medical displaceable contouring mechanism 100 can be stored in an emergency response location (in a city, a building, a state, a country, by the Red Cross, etc.), and prior to, during, or after the emergency. A variety of embodiments of the medical displaceable contouring mechanism 100 can be accessed, transported, airlifted or otherwise situated or located at the disaster or emergency location from a local or remote location, such that a variety of embodiments of the medical displaceable contouring mechanism 100 can be provided and/or assembled for the suitable care over a reasonable duration. In a war, catastrophe, or other emergency situation, for example, hospital units such as MASH units can be provided based on need to adopt to the injuries or wounds of certain individuals. By allowing certain ones of the medical displaceable contouring mechanisms 100 to be stored, moved, assembled, and/or de-assembled quickly, such hospital or triage units can be utilized with great adaptability.

Certain embodiments of the medical displaceable contouring mechanism 100 that are to be used to move or transfer the individual 106 (or are to be used relatively briefly), may be configured or designed to be lighter, for example, than certain embodiments of the one or more beds in which the individual 106 remains for a long time. As such, the configuration, shape, operation, and/or general design of the different embodiments of the medical displaceable contouring mechanism 100 can be selected based, at least in part, on such factors as: it's usage; its duration of usage; whether it is to be used for transportation; whether the individual 106 is using it is generally unconscious; medicated; in trauma; or in a coma during its use, configuration, condition, size, or weight of the individual 106, etc.

Certain embodiments of the medical displaceable contouring mechanism 100 thereby can utilize modular aspects as well as rapid prototyping techniques to create operating tables, beds, etc. that can be adapted to the surgeon or medical personnel, the procedure or operation, and/or the patient. Alternatively, certain embodiments of the medical displaceable contouring mechanism 100 can be configured to create customized pillows or cutouts in bed, or inflatable deflatable versions of the at least one displaceable contouring unit(s) 102.

Figure 5:
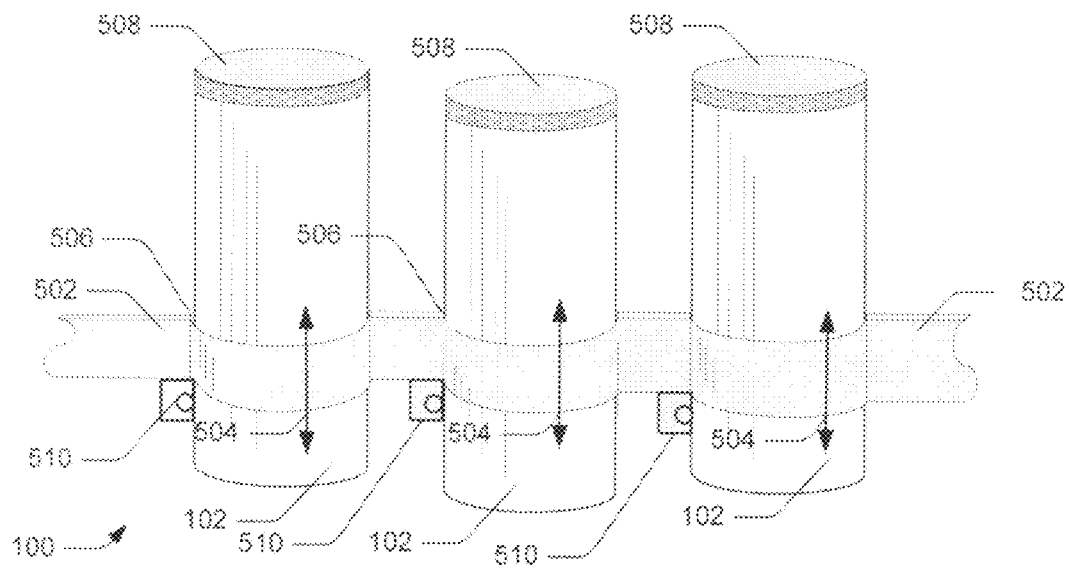
FIG. 5 is a diagram of one embodiment of a number of the displaceable contouring unit(s)

A number of embodiments of the at least one displaceable contouring unit(s) 102 are described. FIG. 5 shows one embodiment of a number of the at least one displaceable contouring unit(s) 102 that are integrated within a frame 502, where longitudinal motion (indicated by arrows referenced as 504) may be allowed through certain ones of the at least one displaceable contouring unit(s) 102 with respect to the frame 502. Each of the at least one displaceable contouring unit(s) as described with respect to FIG. 5 of a generally cylindrical or other shape, can be mounted within a respective displaceably mating recessed portion 506 that may be formed in or by the frame 502. Certain embodiments of the at least one displaceable contouring unit(s) 102 can include a conformable portion 508, which under relatively light pressure can conform to, adapt to, or generally angle to reflect the body of the individual 106 at that particular location. Certain embodiments of the conformable portion 508 are generally formed with a conformable material such as a gel, a fluid such as water, etc., a liquid, a gas, air, a solid-filler material such as a bean-bag material, etc.

While FIG. 5 shows the frame 502 configured to extend along a single direction, certain embodiments of the frame 502 can be configured, shaped, designed, displaced, or arranged to allow the at least one displaceable contouring unit(s) 102 to extend along one, two, or three substantially orthogonal directions, in a regular or dissimilar configuration along each of the one, two, or three directions. Certain embodiments of the medical displaceable contouring mechanism 100 can also be configured to be modified or reconfigured over time. For example, consider the medical displaceable contouring mechanism 100 being configured as an operating table, in which the individual 106 may have to be turned on their front, side, back, through a variety of positions, etc. during the operation. Certain embodiments of the medical displaceable contouring mechanism 100 can be configured to be modified (such as with a number of settings) which can be recalled to reposition the at least one displaceable contouring unit(s) 102 as may be desirable for the particular individual 106 when in a particular position.

Figure 9:
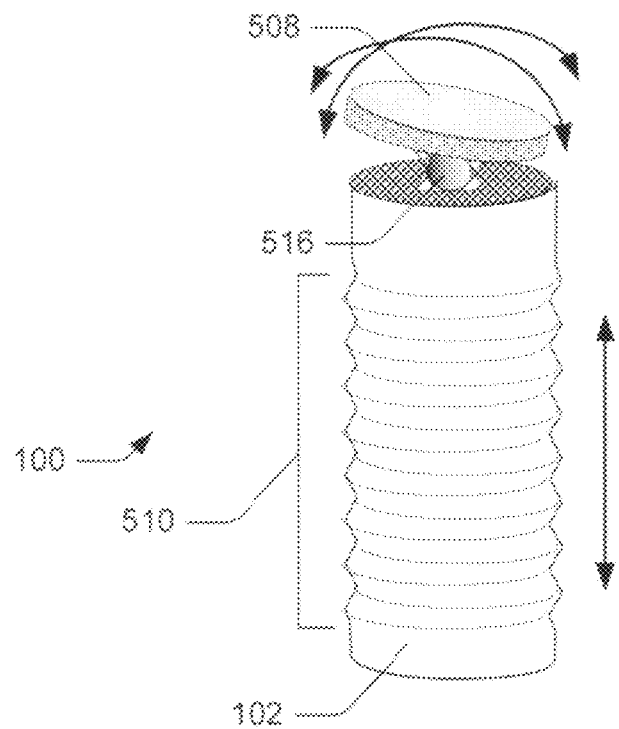
FIG. 9 is a diagram of another embodiment of the displaceable contouring unit(s)

Certain embodiments of the at least one displaceable contouring unit(s) 102 of the medical displaceable contouring mechanism 100 can include an actuator 510 such as may displace the at least one displaceable contouring unit(s) 102 in a desired direction, e.g., up or down as illustrated in FIG. 5. A variety of electromechanical, computerized, controller-based, mechanical, pneumatic, hydraulic, fluid-based, stepper motor, salvo mechanism, etc., or other known actuators may be used as the displacement actuator 510 (which may provide linear displacement) as described with respect to FIG. 5, and may be under the control of the medical displaceable contouring controller 97, as described with respect to FIG. 4. Another embodiment of the actuator 510 can be configured as illustrated in FIG. 9, in which certain embodiments of the at least one displaceable contouring unit(s) 102 can be filled with air, a fluid, a liquid, a gas, etc., which could extend an expansion portion formed therein to provide motion as indicated by the arrow. Such displacement mechanisms as described with respect to FIGS. 4 and 9 are intended to be intended to be illustrative in nature, but not limiting in scope.

As such, displacement of or by certain embodiments of the at least one displaceable contouring unit(s) 102 may be effected using a variety of techniques, mechanisms, and/or devices that are illustrated, but not limited to those, as described in this disclosure. Different such actuators, displacement devices, and the like as are generally understood by those skilled in the actuator technologies can be utilized without departing from the scope of the present disclosure, as set forth in the claims. There may thereby be a wide variety of actuators that may provide actuation of the at least one displaceable contouring unit(s) 102 to effect displacement of the portion that supports the individual, e.g., the conformable portion 508. Certain embodiments of the actuator 510 can be controlled, for example, by certain embodiments of the medical displaceable contouring controller 97 as described with respect to FIG. 4.

A single one of the at least one displaceable contouring unit(s) 102 as described with respect to FIG. 5 is illustrated, movable with respect to the frame 502 (which may result from displacement by the actuator 510). The dimensions, configuration, material, shape, design, and other aspects of each displaceable contouring unit(s) may be considered as a design choice, and should not be considered limiting in scope. It should be considered, however, that certain configurations of the at least one displaceable contouring unit(s) 102 (such as cylindrical) can allow for a considerable spacing to form between adjacent ones. As such, it may be desired to alter the dimensions of certain embodiments of the displaceable contouring unit(s) 102, such as to reduce spacing formed there between which may be uncomfortable to certain individuals 106. Sheets, cushions, inserts, etc. can be used in conjunction with certain embodiments of the medical displaceable contouring mechanism 100 to fit between or cover over joints between adjacent conformable portions 508 to thereby limit any undesirable or uncomfortable effects of spaces or voids formed between adjacent ones of the displaceable contouring unit(s) 102. Certain configurations of spacing between adjacent sets of displaceable contouring unit(s) 102 can be desirable. For example, spacing between adjacent displaceable contouring unit(s) 102 can allow ventilation, as well as associated cooling to the individual. Spacing between the displaceable contouring unit(s) 102 can allow liquids, gasses, and other fluids to escape from contact with the individual, which may thereupon be readily cleaned if necessary. As such, whether to apply spacing between displaceable contouring unit(s) 102 can be a design choice. In certain embodiments, the shape of the conformable portion 508 may reflect the general cross-sectional shape of the remainder of the at least one displaceable contouring unit(s) 102, while in other embodiments, the cross-sectional shapes of elements 102 and 508 may be dissimilar.

Figure 7:
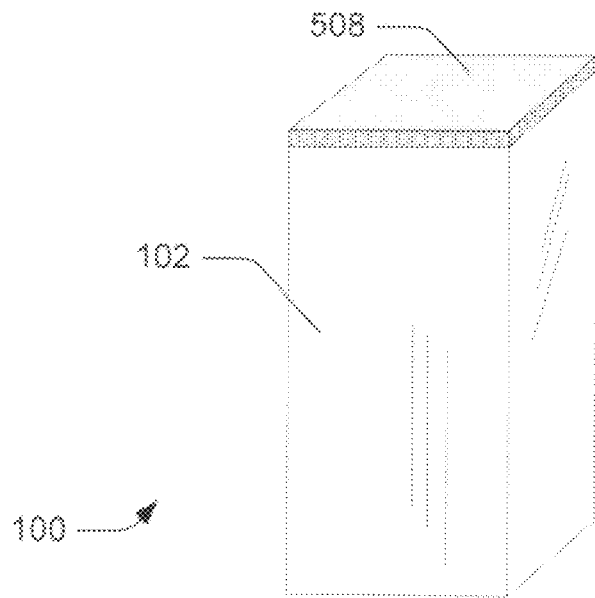
FIG. 7 is a diagram of still another embodiment of the displaceable contouring unit(s)

FIG. 7 shows an embodiment of the at least one displaceable contouring unit(s) 102 that has a generally rectangular cross-sectional configuration. These rectangular embodiments of the at least one displaceable contouring unit(s) 102 can allow relatively tight spacing of the units. Other shapes of the at least one displaceable contouring unit(s) 102 can be utilized while remaining within the intended scope of the present disclosure.

Figure 8:
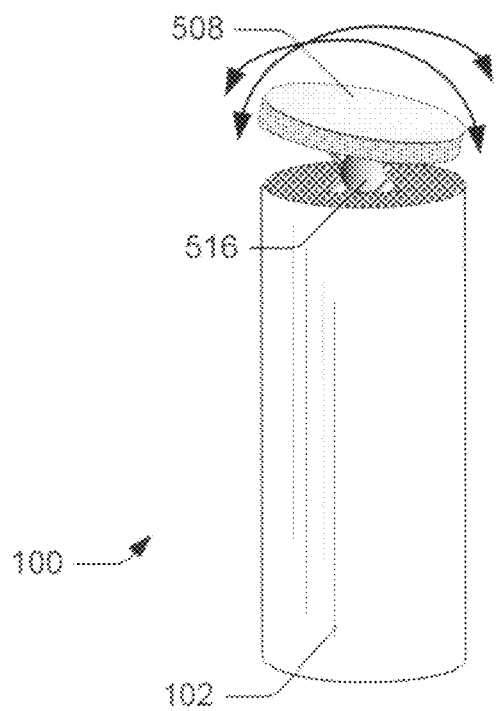
FIG. 8 is a diagram of yet another embodiment of the displaceable contouring unit(s)

FIG. 8 shows another embodiment of the displaceable contouring unit(s) 102 that is configured with a pivotable conformable portion 508, to attach to the remainder of the displaceable contouring unit(s) by a joint number 516. Certain embodiments, a joint member 516 can include a freely-displaceable number, such as being attached by a ball bearing or hinge, to thereby allow the pivotable conformable portion 508 to freely pivot with respect to the remainder of the displaceable contouring unit 102. Certain embodiments of the joint member 516 can be controllable, such as to allow for a pivotable conformable portion 508 to assume an angle with respect to, for example, other pivotable conformable portions in the vicinity, other displaceable contouring unit(s), the contour of the individual 106, etc. Different embodiments of the joint member 516 can be configured to allow the desired rotation or hinging of the pivotable conformable portion 508 in the desired or designed directions and/or axes.

Figure 10:
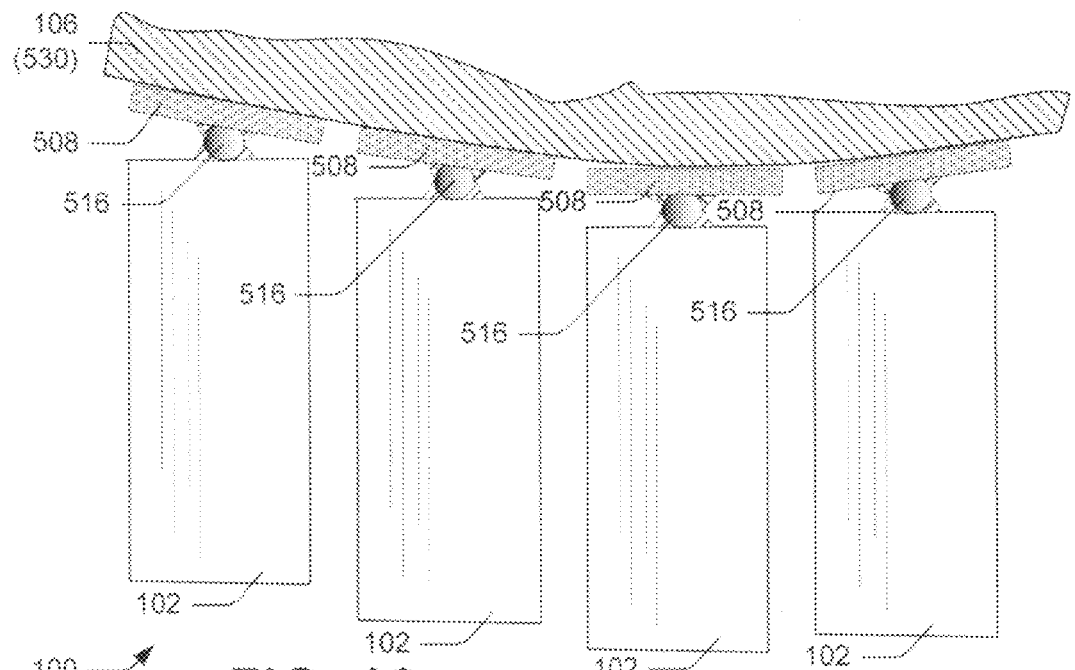
FIG. 10 is a diagram of an embodiment of a number of the displaceable contouring unit(s) being displaced to adapt to a contour (such as that of an individual)
Figure 11:
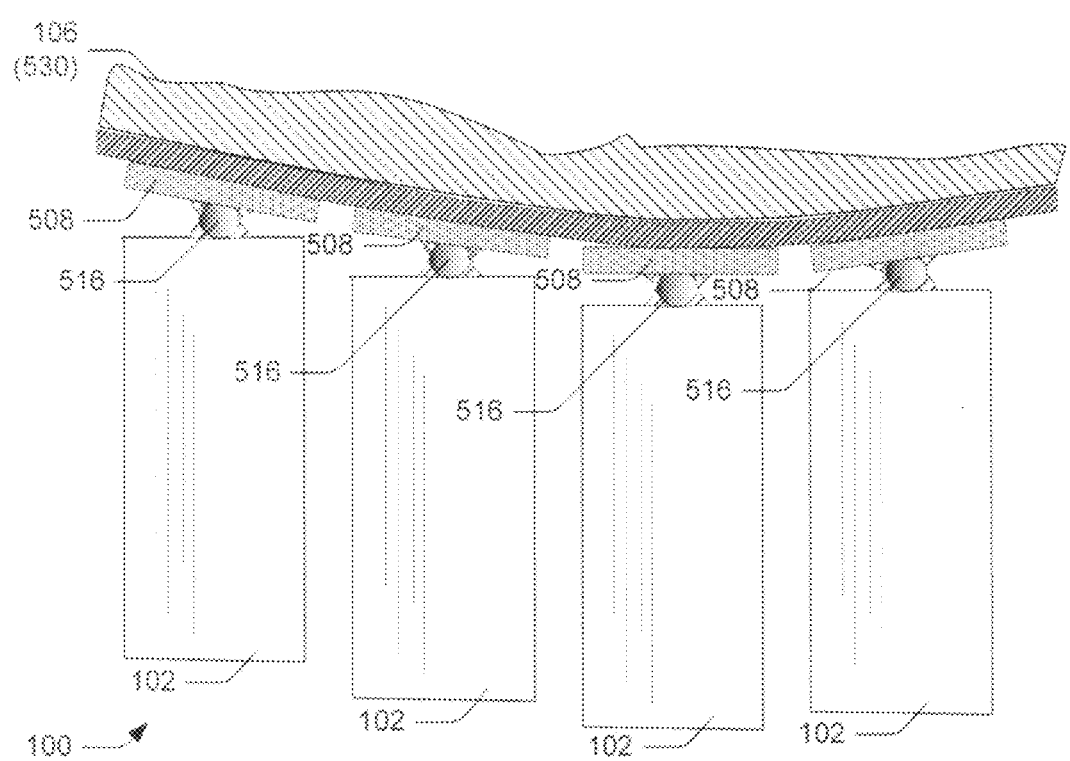
FIG. 11 is a diagram of another embodiment of a number of the displaceable contouring unit(s) being displaced to adapt to a contour (such as that of an individual)
Figure 12:
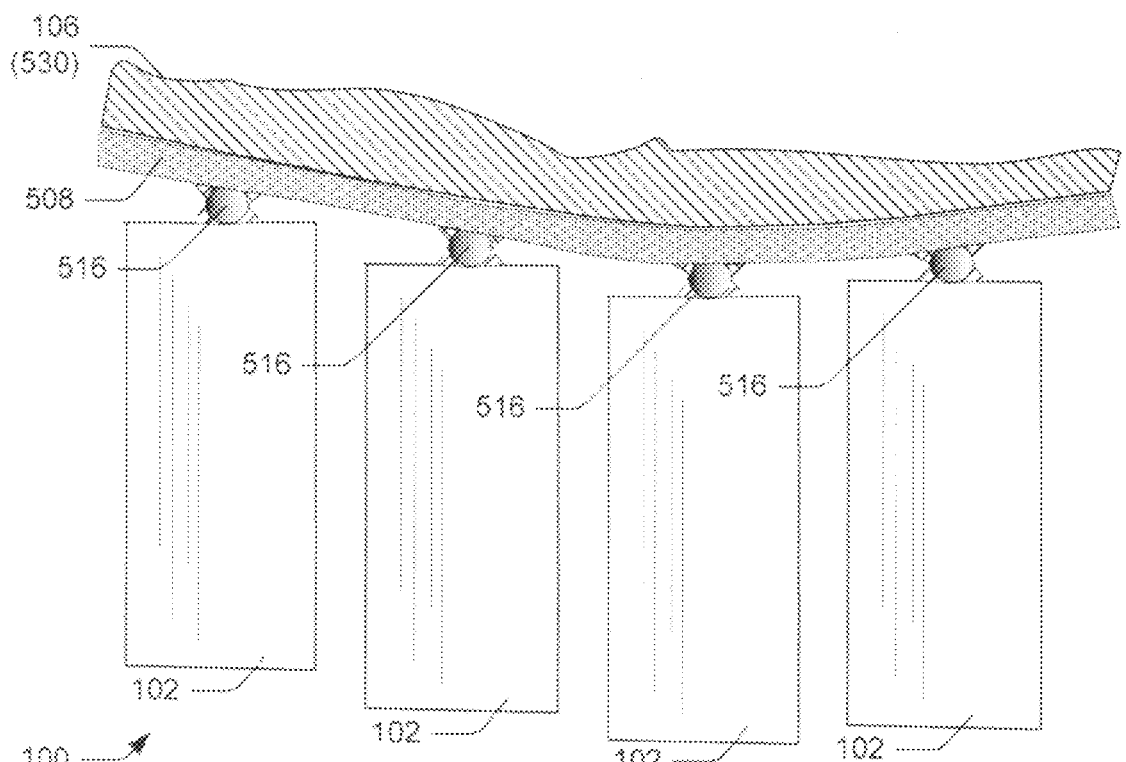
FIG. 12 is a diagram of another embodiment of a number of the displaceable contouring unit(s) being displaced to adapt to a contour (such as that of an individual)

Certain embodiments of the displaceable contouring unit(s) 102 can thereby be configured and/or displaced to provide support for the individual 106, considering the contour of the individual 106 as described with respect to FIG. 10. For example, the vertical position of each of the at least one displaceable contouring unit 102 can be displaced to a position to approximate a contour 530 of the individual 106. Thereupon, the pivotable conformable portion 508 can be configured to be controllably rotated (or allowed to rotate) to approximate the angle of the contour.

Figure 13:
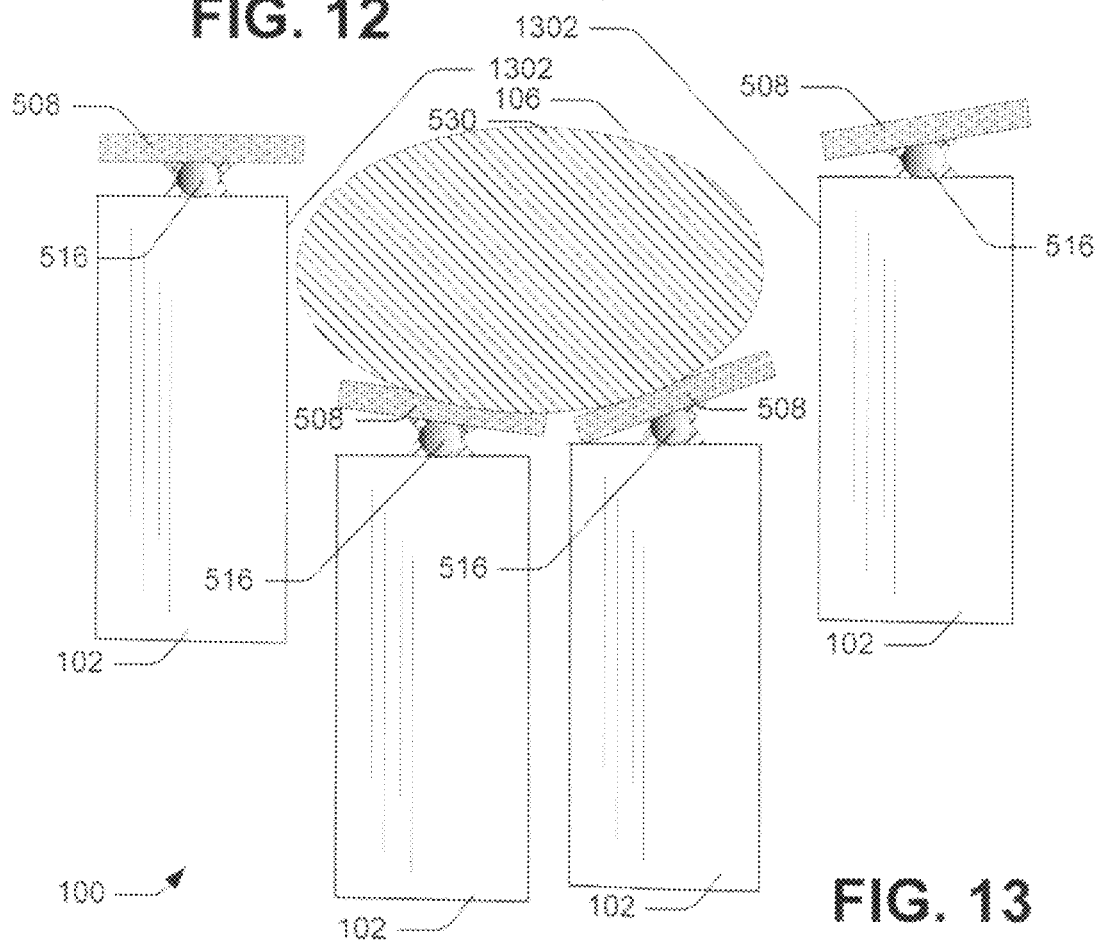
FIG. 13 is a diagram of another embodiment of a number of the displaceable contouring unit(s) being displaced to adapt to another contour.

Certain embodiments of the displaceable contouring unit(s) 102 can extend, as illustrated in FIG. 13, above the plane of the other displaceable contouring unit(s) 102 such as to limit travel of the individual 106, or other object, in a direction that is substantially orthogonal to the direction which many of the displaceable contouring unit(s) 102 are intended to support the individual 106. For example, the outer-two most (or any other) displaceable contouring unit 102 in FIG. 13 can be displaced upwardly to a level sufficient to limit travel of the at least the portion of the individual 106 (e.g., a portion of a leg as illustrated in cross-section) in a substantially left-right direction as illustrated in FIG. 13, while the inner-two most displaceable contouring units 102 of FIG. 13 are configured to support the at least the portion of the individual 106 in a substantially upward/downward direction as illustrated in FIG. 13.

Certain embodiments of the displaceable contouring unit(s) 102 as described with respect to FIG. 13 can include a stabilization surface 1302 that can limit motion of a portion of the individual in a prescribed direction, which may or may not be coincident with the direction of support by the conformable portion(s) 508 (which may or may not be pivotable). During operation of certain embodiments of the medical displaceable contouring mechanism 100, certain ones of the displaceable contouring units 102 may be extended up to the side of the individual. As such, depending on the configuration and construction of the medical contouring mechanism 100, certain embodiments of the stabilization surface 1302 can be configured and raised to a level to limit travel of the individual laterally past the displaceable contouring unit(s) 102. Certain embodiments of the displaceable contouring units 102 can be configured with one or more stabilization surface 1302, as illustrated with respect to FIGS. 22, 23, and/or 24.

With certain embodiments of one or more of the displaceable contouring units 102, the stabilization surface 1302 can correspond to certain embodiments of the conformable portion(s) 508. For instance, with those embodiments of the medical displaceable contouring mechanism 100 that are configured as casts, braces, etc., as illustrated in FIG. 27, for example, the conformable portion(s) 508 can be configured to stabilize at least that portion of the individual's body part that it comes in contact with against motion in that direction. As such, the pressure applied by certain embodiments of the one or more of the displaceable contouring units 102 can also be configured to stabilize the body part of the individual 106.

Such upward or downward displacement (as shown in FIG. 13) of certain embodiments of the at least one displaceable contouring unit(s) 102 can allow the respective supportive portions thereof to approximately follow the contour of the individual 106 at that respective location. Certain embodiments of the displaceable contouring unit(s) 102 can be configured to be relatively soft or deformable at those locations that can come in contact with the individual 106, and thereby would be useful as an operating table, bed, couch, piece of furniture, etc. in which any excessive or enhanced pressure as would be applied to the individual 106 can be limited.

Figure 14:
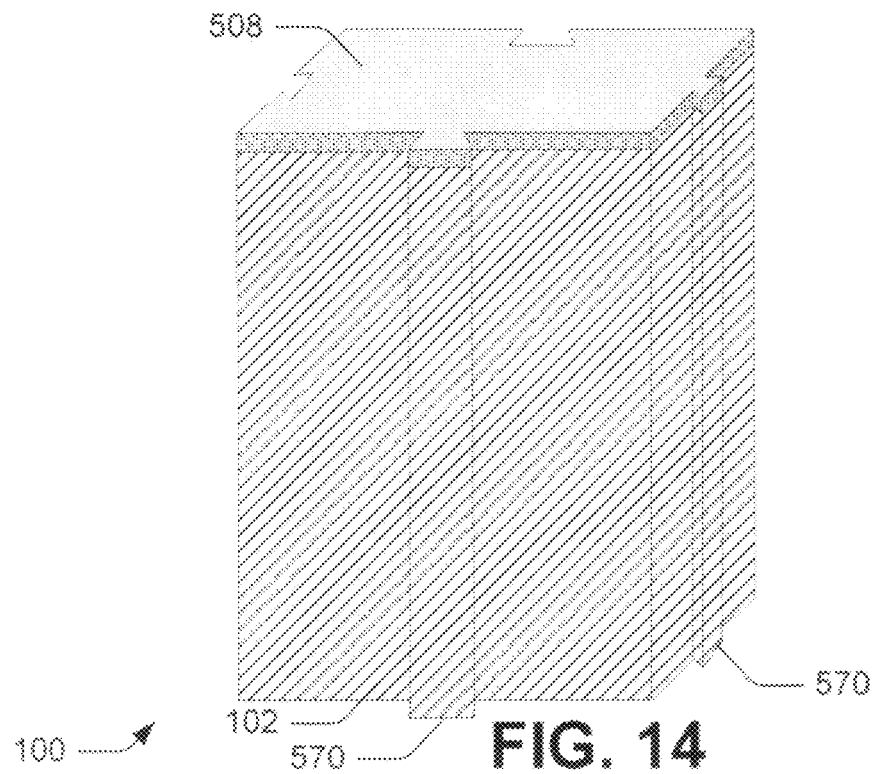
FIG. 14 is a diagram of another embodiment of the displaceable contouring unit.
Figure 15:
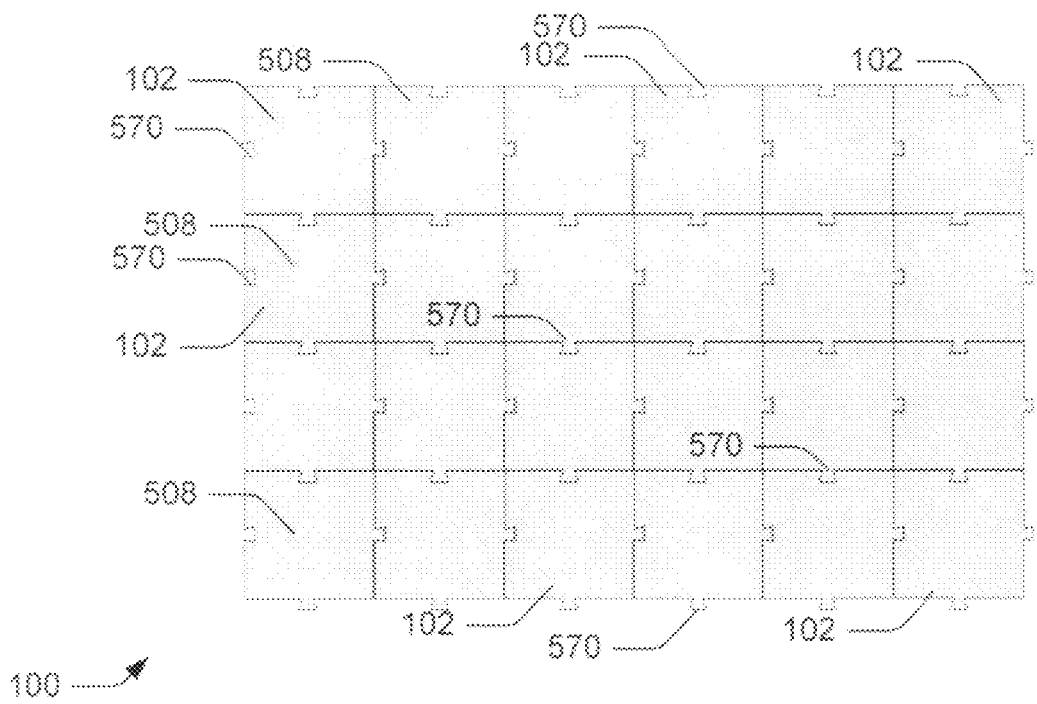
FIG. 15 is a diagram of a number of the displaceable contouring unit(s) as described with respect to FIG. 14 being configured to form another embodiment of the medical displaceable contouring mechanism.
Figure 16:
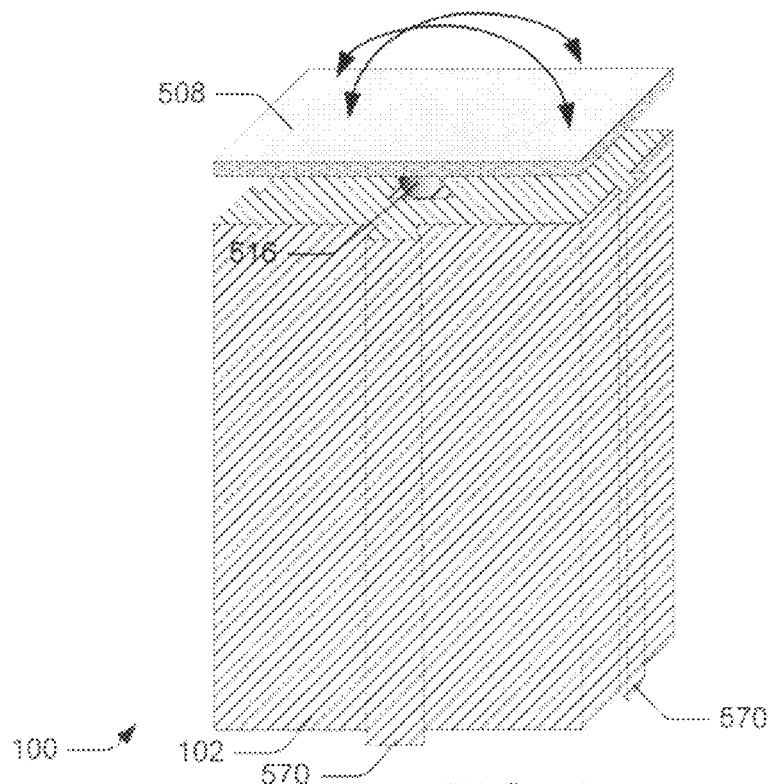
FIG. 16 is a diagram of another embodiment of the displaceable contouring unit.
Figure 17:
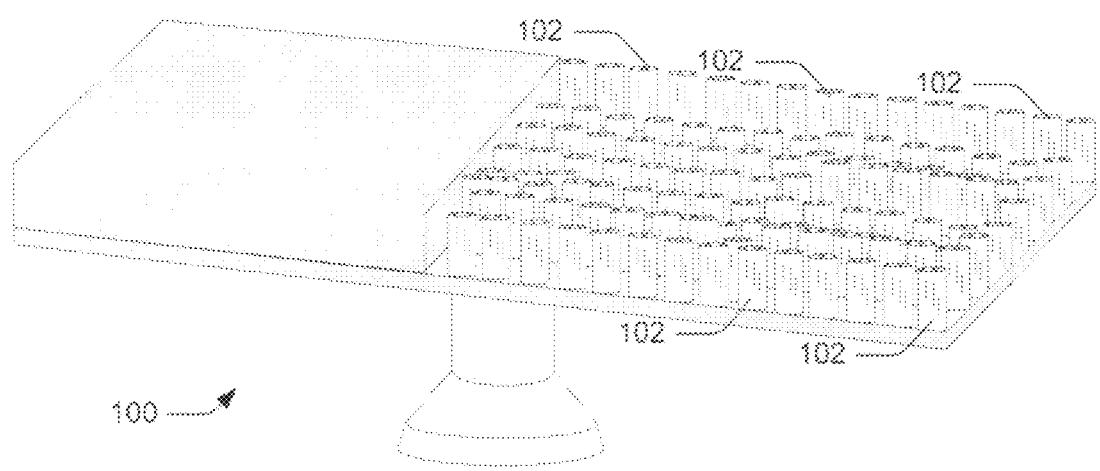
FIG. 17 is a diagram of still another embodiment of the displaceable contouring unit.

Certain embodiments of the at least one displaceable contouring unit(s) 102 can be configured to displaceably engage with other displaceable contouring unit(s) 102, as described with respect to FIGS. 14, 15, and 16. For example, certain embodiments of the at least one displaceable contouring unit(s) 102 can be configured to be displaced with respect to other ones of the at least one displaceable contouring unit(s) such as to provide a substantially contoured upper surface to mirror or conform with the contour of the individual 106 being supported. Certain embodiments of the at least one displaceable contouring unit(s) 102 can be configured with guides 570 that allow relative motion in certain direction(s) (e.g., in or out of the page as illustrated in FIG. 15) while limiting relative motion in certain direction(s) (e.g., in the plane of the page as illustrated in FIG. 15). The embodiment of the guides 570 as illustrated in FIG. 15 is intended to be illustrative in nature, and not limiting in scope. For example, the guides 570 as illustrated are of a tongue-and-groove configuration, but other configurations can be used in certain embodiments at the medical displaceable contour mechanism 100 as well that would allow relative motion between adjacent displaceable contouring units 102. In addition, each of the at least one displaceable contouring unit(s) 102 as illustrated in FIGS. 14 and 15 is configured with guides 570 that limits relative motion to adjacent displaceable contouring unit(s) 102 along two directions (e.g., up-and-down and left and right as illustrated in FIG. 15), but in certain embodiments such motion can be limited in one direction only.

FIG. 16 shows another embodiment of the displaceable contouring unit(s) 102 that is configured with a pivotable conformable portion 508 which has certain similarities with the FIG. 8 embodiment, which can attach to the remainder of the displaceable contouring unit(s) by the joint number 516. With certain embodiments of the medical displaceable contouring mechanism 100, a joint member 516 can be a freely-displaceable member, such as ball bearings which are known to allow the pivotable conformable portion 508 to freely pivot with respect to the remainder of the displaceable contouring unit 102. Certain embodiments of the joint number 516 can allow their respective positioning to be controllable, such as to allow for a pivotable conformable portion 508 to assume an angle with respect to, for example, other pivotable conformable portions in the vicinity, other displaceable contouring unit(s), the contour of the individual 106, etc.

Certain embodiments of the displaceable contouring unit(s) 102 can thereby be configured and/or displaced to provide support for the individual 106, considering at least partially the contour of the individual 106 as described with respect to FIG. 10. For example, the vertical position of each of the at least one displaceable contouring unit 102 can be displaced to a position to approximate a contour 530 of the individual 106. Thereupon, the pivotable conformable portion 508 can be configured to be controllably rotated (or allowed to rotate) with respect to the remainder of the at least one displaceable contouring unit 102 to thereby approximate the angle of the contour.

Certain embodiments of the at least one displaceable contouring unit 102 that are displaceably secured to at least one other adjacent displaceable contouring unit(s) 102 can provide relative motion using expansion portions as described with respect to FIG. 9. The embodiment of the at least one displaceable contouring unit 102 as described with respect to FIG. 9 can be configured to provide such relative motion.

The operation and/or functionality of the embodiments of the at least one displaceable contouring unit 102 as described with respect to FIGS. 1 to 21 are thereby intended to be illustrative in nature and not limiting in scope. As such, configurations, shapes, types of guides 570, etc. and other characteristics can be considered to be a design choice which can be easily modified while remaining within the intended scope of the present disclosure which are to be limited based entirely on context, particularly the language of the claims.

Certain embodiments of the medical displaceable contouring mechanism 100 as described with respect to FIGS. 1 to 21 can thereby be configured in a variety of configurations to support the individual 106 using at least one of the at least one displaceable contouring unit 102, the latter of which can be configured along a one-dimensional, a two-dimensional, or a three dimensional array, or other configuration as claimed, recited, or described in this disclosure. Certain embodiments of the medical displaceable contouring mechanism 100, as described with respect to FIG. 17, can also be configured to include a support portion 590, that can be configured as a conventional bedding portion to support a portion of the individual 106, for example, while also including at least one of the displaceable contouring unit 102. As such, certain embodiments of the medical displaceable contouring mechanism 100 can be configured with the support portion 590 to support a portion of the individual 106 who thereupon may not be as likely to form bedsores, experience poor circulation, etc. Certain embodiments of the medical displaceable contouring mechanism 100 can be configured such as to reduce its complexity of the structure or operation. Certain embodiments of the support portion 590 can be shaped or contoured, for example, to roughly conform to the shape of the individual 106 such as by using a foam, a liquid, a gas, a gel, a flexible, deformed, and/or another deformable material or combination thereof.

By comparison, certain embodiments of the medical displaceable contouring mechanism 100 can include the at least one of the displaceable contouring unit 102 (e.g., that can support the portion to the right in FIG. 17 which may be situated under a portion of the individual) can operate similar to those embodiments of the medical displaceable contouring mechanism 100 as described in other portions of the disclosure. By displacing the at least one of the displaceable contouring unit 102 in those embodiments of the medical displaceable contouring mechanism 100 that can include the partial support portion 590, the pressure applied to the support portion 590 can also be reduced or taken up by portions of the at least one of the displaceable contouring unit 102.

Certain embodiments of the medical displaceable contouring mechanism 100 can be provided with an access portion 620 as described with respect to FIGS. 18 and 19, in which at least certain ones of the at least one of the displaceable contouring unit 102 can be removed, positioned, displaced, rotated, or otherwise configured to allow a physician or other medical or treating person to gain access to a portion of the individual 106. The purpose of providing the access portion 620 to the individual 106 can vary, such as permitting a surgeon or other medical personnel to treat the individual 106; allowing a caretaker to clean the individual 106 and/or portions of the medical displaceable contouring mechanism 100; providing a bed-pan or other mechanism to the individual that can be situated at a suitable position within the medical displaceable contouring mechanism 100, such as might be able to be repositioned or removed for cleaning; etc.

In certain surgical, hospital, nursing home, ambulance, ski patrol, and other settings, for example, certain embodiments of the medical displaceable contouring mechanism 100 can thereby be configured depending upon but not limited to such factors as: the individual 106, the condition of the individual 106, the procedure or treatment being applied to the individual, the duration which the individual 106 is to be situated in the medical displaceable contouring mechanism 100, the particulars or desires of the treating physician or medical personnel, etc. Certain embodiments of the medical displaceable contouring mechanism 100 can be configured to accommodate unusual individual 106 positions, such as may be the case with individuals 106 undergoing spinal or neck surgeries in which the patient individuals 106 may even be facing downward, be bent or curved, or even have to undergo frequent repositioning.

To allow for change of operative site (e.g. anterior to posterior or vice versa) on certain individuals 106, such as may be the case when operating on or treating certain spine, neck injury, or other major injury or trauma patients; certain embodiments of the medical displaceable contouring mechanism 100 can be formed with two or more support segments. In certain instances, it may be possible to reconfigure or modify the medical displaceable contouring mechanism 100 such as to permit a physician or other medical personnel to change operative site while maintaining stability of the position of the remainder of the body. For example, one segment may support a front or anterior portion of the individual 106 while another segment may support a back or posterior portion of the individual 106. A variety of structures or frameworks may be provided such as to allow the individual 106 to be maintained between the segments. The anterior segment of the individual 106 can be configured to conform to the anterior portion of the individual, while the posterior segment of the individual 106 can be configured to conform to the posterior portion of the individual, as described with respect to FIGS. 18 and 19 for example. Consider that when the individual 106 is undergoing surgery in which the individual can be accessed from different sides, and/or at different locations or sites, etc.

The embodiment of the medical displaceable contouring mechanism 100 as described with respect to FIGS. 18 and 19 can thereby be configured to include a first medical displaceable contouring support portion 600 and a second medical displaceable contouring support portion 602. The two medical displaceable contouring mechanisms 600 and 602 as shown in FIG. 18 are shown in a separated position such that the individual 106 such as a patient can get onto, get off of, and/or lie on the first medical displaceable contouring support portion 600 without interference by the second medical displaceable contouring support portion 602. Certain embodiments of the second medical displaceable contouring mechanism 602 can thereupon be rotated on top of the individual 106 as indicated by the arrows of FIG. 18, into the relative position as illustrated in FIG. 19. The first medical displaceable contouring support portion 600 and the second medical displaceable contouring support portion 602 are each illustrated as each supporting the individual 106 entirely with the at least one of the displaceable contouring unit 102. It may be possible that certain embodiments of the first medical displaceable contouring support portion 600 and/or the second medical displaceable contouring support portion 602 could be configured with more conventional bedding or support portions, as illustrated with respect to FIG. 17, and/or a variety of access portions. For example, if the surgery was going to be performed exclusively on the anterior portion of the individual 106, then only the anterior support portion may be configured with the at least one of the displaceable contouring unit 102 in certain embodiments of the medical displaceable contouring mechanism 100.

Certain portions of the first medical displaceable contouring support portion 600 and/or the second medical displaceable contouring support portion 602, that come in contact with portions of the individual 106, may be provided with one of the variety of embodiments of the at least one of the displaceable contouring unit 102 as described in this disclosure. Other portions of the medical displaceable contouring support portions 600 and 602 may be configured or operated for other functionality, such as providing medication, an oxygen or gas mask, ventilation, instrumentation, sensors, etc., as desired.

The embodiment of the medical displaceable contouring mechanism 100 as described with respect to FIGS. 18 and 19 can, for example, include an access portion 620 that can be configured to allow the doctor, or other medical personnel, to access the individual 106 during an operation or other procedure. For example, certain embodiments of the medical displaceable contouring mechanism 100 can be configured to provide the access portion over the head or other portion of the individual 106 to limit claustrophobia by the individual 106.

Certain embodiments of the medical displaceable contouring mechanism 100 can be configured to allow the individual 106 to be rotated, or otherwise repositioned or positioned, such as may become necessary during an operation or procedure. For example, the embodiment of the medical displaceable contouring mechanism 100 as described with respect to FIG. 19 can be configured to be rotated such that the individual 106 may be facing downward, or in some other position. It is not uncommon, during certain types of surgery in particular, that the individual 106 may have to be rotated, turned, or positioned.

Consider that certain operations or procedures, such as an x-ray, a CAT scan, and/or other electromagnetic radiation, electromechanical, optical, or other procedures, may be extremely expensive and may rely largely on the individual remaining almost motionless. If the individual moves, even as a result of an itch or sneeze, the quality of and/or the information obtainable from such results may be degraded considerably. Certain embodiments of the medical displaceable contouring mechanism 100 can therefore be configured to maintain the individual in an almost still or almost motionless position, and therefore be highly applicable to such procedures or operations whose quality may depend largely on the lack of motion of the individual.

While FIGS. 18 and 19 illustrate certain aspects of an embodiment of the medical displaceable contouring mechanism 100 that include two relatively movable medical displaceable contouring mechanisms being applied from above and below the individual (as illustrated in the figures), it is also possible to provide a variety of number and/or orientation of the medical displaceable contouring mechanism(s) 100. For example, in certain instances, it may be desirable to provide a distinct medical displaceable contouring mechanism around each side (four total) of a portion of the individual (such as the torso or head) or about the entire individual. Alternately, it may be desired to allow certain ones of the medical displaceable contouring mechanism to encounter the individual such as from the side of the individual. It may be desired to move one or more of the medical displaceable contouring mechanisms through a number of angles and/or to a number of positions and/or angles such as may be desired by the physician, treating person, or the individual.

Certain embodiments of the medical displaceable contouring mechanism 100 can act to reposition at least one of the displaceable contouring unit(s) 102 of the individual when moved or repositioned within the medical displaceable contouring mechanism. For instance, if certain embodiments of the medical displaceable contouring mechanism 100 are angled to a different position, then the side of the individual that is facing down (and is exposed to the effects of the greatest pressure resulting from gravitational force) will change. As such, the pressure(s) and/or force(s) that may be applied from the body of the individual against the different displaceable contouring unit 102 will change depending on the position of the individual relative to gravity. Consider that if the individual is supported against gravity primarily on their back, their sides and front may be exposed to very little force as a result of gravity. By comparison, if the individual is moved to their side, then only that side will experience the most pressure resulting from gravity. Certain embodiments of the medical displaceable contouring mechanism 100 may be configured to reduce any pressure differential (to limit pressure points) on the side of the body that is exposed to the greatest gravitational pressures.

Similar acceleration forces may be applied to individuals being transported. For example, it may be important to transport certain trauma patients, pre-natal infants, and/or other seriously injured or sick individuals via ambulance, air transport, or other mechanism of transportation by which the individual can be exposed to considerable forces and/or acceleration as a result of the transport. Similarly, it may be important to limit the pressures applied to the individual as a result of such forces and/or accelerations. Certain embodiments of the medical displaceable contouring mechanism 100 may be configured to displace or position certain of the at least one of the displaceable contouring unit(s) 102 such as to protect particularly injured or sensitive portions against the forces and/or accelerations inherent in the transport.

Certain embodiments of the medical displaceable contouring mechanism 100 can utilize such illustrative but not-limiting mechanisms as gyroscopes, global positioning system (GPS), inertial units, pendulum indicators, as well as a general indication by a technician as to which direction is "down" relative to gravity and the individual. The more complex gyroscopic systems, global positioning systems (GPS), and/or inertial unit systems may be used, for example, with vehicular travel or mobile embodiments of the medical displaceable contouring mechanism 100. The more straight forward (technician indicated) systems may be used by stationary embodiments of the medical displaceable contouring mechanism 100.

Certain embodiments of the medical displaceable contouring mechanism 100 that include an individual 106 supported and/or stabilized between two medical displaceable contouring mechanisms 100 (e.g., 600, 602) could act by having the pressure differential fluctuating certain one(s) of the displaceable contouring unit(s) 102 slightly to allow for improved ease of breathing by the individual by allowing their chest to expand and contract more easily. Certain embodiments of the medical displaceable contouring mechanism 100 can also be configured to allow other movements and/or functions by the individual, as appropriate. Certain embodiments of the medical displaceable contouring mechanism 100 can be configured such that the individual can actuate a release mechanism, such as to limit certain claustrophobic aspects of certain embodiments of the medical displaceable contouring mechanism 100.

Upon consideration of the arrows as included in FIG. 19, certain embodiments of the medical displaceable contouring mechanism 100 can be rotated, turned, repositioned, etc. as may be desired by the treating physician or other person, or the individual 106, while maintaining support (i.e., under reduced pressure) of the individual 106 throughout the operation or procedure. Robotics, control mechanisms, computer-based mechanisms, and the like can be utilized to perform suitable motion to support portions 600, 602, etc. as described in this disclosure as is generally understood by those skilled in the robotics and/or control technologies. With certain embodiments of conventional operating tables, for example, patients may have to be strapped down, or otherwise secured to the conventional operating table such as by utilizing straps, belts, inserts, add-on portions etc. Positioning the individual 106 in a number of positions relative to a conventional operating table, or hospital bed, etc. utilizing a variety of belts, straps, etc. can result in excessive and/or non-uniform loads being applied to various portions of the individual 106, such as may be undesirable or even harmful to the individual 106. With certain embodiments of operating tables, hospital beds, ambulance stretchers, etc., the individuals 106 may even have to be rotated and repositioned on top of the operating table, etc.

Certain embodiments of the medical displaceable contouring mechanism 100 can be utilized to assist in repositioning of the individual, rolling the individual 106, etc, by physicians or medical personnel on top of conventional hospital beds, operating tables, etc. can result in damage to, hurting, pain, or injury to the individual 106 as well as the physician or other medical personnel. As such, certain embodiments of the medical displaceable contouring mechanism 100, as described in this disclosure, can be configured to allow the individual 106 to be moved, repositioned, re-situated, or otherwise displaced while limiting excessive load being applied to the individual 106. As such, certain embodiments of the medical displaceable contouring mechanism 100 can have at least some of their displaceable contouring units 102 repositioned or displaced during an operation or procedure when the individual is being repositioned such as to compensate for the varying contour of the individual. For example, certain embodiments of the medical displaceable contouring mechanism can be configured to conform to the individual 106 lying on their back, for example. As the individual is displaced, allowed to move, or rolled onto their stomachs, for example, certain ones of the displaceable contouring unit 102 can be displaced to conform to the different contour of at least a portion of the individual.

With certain embodiments of the medical displaceable contouring mechanism 100 as described in this disclosure, certain ones of the displaceable contouring unit(s) 102 can even be displaced in a manner as to assist in rolling the individual 106 or moving a portion of the individual. For example, certain of the displaceable contouring unit(s) 102 can be displaced alone or in combination such as by creating a wave, message, or the like by the displacement of one or more of the displaceable contouring unit(s) 102. By comparison, certain embodiments of the displaceable contouring unit(s) 102 that can apply a rolling, turning, or other displacing force to the individual, less force may have to be applied by the physician, nurse, the individual, or other treating person who may be attempting to move or roll the individual. The force, which certain embodiments of the medical displaceable contouring mechanism 100 can apply to the individual 106 may not be sufficient in itself to reposition the individual, but such force may help. Additionally, certain embodiments of the medical displaceable contouring mechanism 100 can be configured to allow for convenience and easy access to various portions of the individual 106. In addition such rotating or displacing of the individual can be performed.

A considerable amount of this disclosure relates to individuals 106 being supported by certain embodiments of the medical displaceable contouring mechanism 100, in which the individuals 106 are patients in hospitals, operating rooms, being transferred by ambulance, being treated by a physician, medical personnel, lifeguard, and/or ski patrol, etc. It is to be understood that certain embodiments of the individual 106 who can also utilize certain embodiments of the medical displaceable contouring mechanism 100 can also be relatively healthy individuals 106. For instance, it may be desired to configure the medical displaceable contouring mechanism 100 that can be configured with a displaceable contouring unit 102 in such devices as a bed, in which the individual 106 can rest on with reduced number of or intensity of pressure points and/or improved blood circulation.

Certain embodiments of the medical displaceable contouring mechanism 100 can be configured, for example, to improve sleep and/or improve blood circulation for individuals 106 in their home, etc. Consider, for example, that a variety of embodiments of the medical displaceable contouring mechanism 100 can be configured as furniture, beds, couches, sofas, seats, chairs, etc. such as people can use in their home, work, and/or vehicles. Certain embodiments of the displaceable contouring units 102 can be configured to limit sideways, backwards, lateral, or other motion of the individual as situated in an ambulance stretcher, a rescue or ski-patrol stretcher, etc. may be limited or retarded by certain embodiments of the displaceable contouring units 102, such as may limit so-called secondary impacts of the individual following the primary impact of an accident, etc. Such extension or displacement of the displaceable contouring unit(s) 102 can be upon the accident, or can be during the normal vehicle or device operation such as to provide a contoured seat, stretcher, bed, etc. portion of the individual, as well as the supported portion of the individual. It may be desirable to provide at least certain embodiments of the displaceable contouring unit 102 that can be adapted for medical transport in a variety of vehicles in which at least some of its operators or occupants would be made more comfortable, and/or have improved blood circulation over a long trip. Certain embodiments of the medical displaceable contouring mechanism 100, by improving the comfort of the individual 106, may even allow the individual to remain more alert during treatment or certain medical procedures (e.g., x-rays, CAT scans, or other electromagnetic radiation application procedures, medicine application, etc.) considering certain ergonomic aspects of the medical displaceable contouring mechanism 100.

Figure 20:
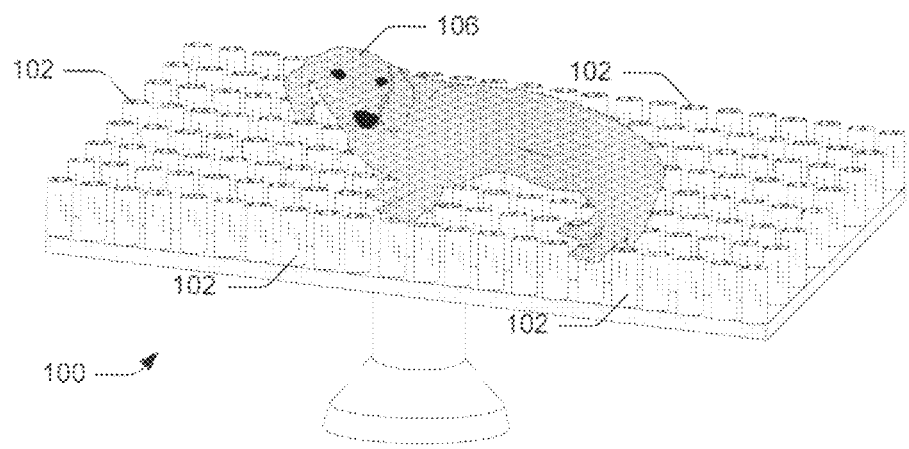
FIG. 20 is a diagram of yet another embodiment of the displaceable contouring unit.

Certain embodiments of the medical displaceable contouring mechanism 100 can be configured for such individuals 106 as an animal as described with respect to FIG. 20. Consider that certain animals may find it more comfortable or restful. Certain embodiments of the displaceable contour unit(s) 102 can be configured to maintain or secure the animal in position. As blood circulation is improved in the animal, for example, then certain embodiments of the medical displaceable contouring mechanism 100 can enhance the comfort of the animal, for example. A considerable amount of the difficulty can be associated with treating animals may result from discomfort and/or reduced blood flow to certain portions of the animal. The variety of animals that can utilize certain embodiments of the medical displaceable contouring mechanism 100 can include, but are not limited to, domesticated animals, wild animals, livestock, etc.

Certain embodiments of the medical displaceable contouring mechanism 100 that are configured to operate on and/or stabilize a body portion (such as casts, braces, traction, etc.) can be applied to or designed to be applied to animals. Consider that certain medical displaceable contouring mechanism 100 that may be configured as body portion casts, for example, that could be applied to horses, dogs, cats, lions, bears, cows, etc., to provide considerable support for a broken or injured portion. Certain embodiments of the medical displaceable contouring mechanism 100 can be formed at least partially from fiberglass, metal, plastic, honeycomb, composites, or other weather-resistant material to be suited for the particular environment that animal is likely to experience. Certain embodiments of the medical displaceable contouring mechanism 100 can be configured with a regularly-shaped (e.g. cylindrical) outer portion, with a number of displaceable contouring units 102 extending inwardly that can separately be displaced to a position to conform to, and stabilize, the part of the animal.

Certain embodiments of the medical displaceable contouring mechanism 100 can be configured such that only certain portions of the individual 106 may be supported by the at least one displaceable contouring unit 102, while other portions of the individual 106 may be supported by accessories, etc. Certain individuals who are in the hospital, for example, may include an accessory portion that can provide support or access to certain portions of the individual 106. Certain embodiments of the accessories may also include one or more of the displaceable contouring unit 102. For example, one embodiment of the medical displaceable contouring mechanism 100 can be configured with such accessories as a traction mechanism as described with respect to FIG. 21, which further includes, for example, a traction mechanism 630 which can include a pin 632 that can extend through a portion of the individual 106 (e.g., a bone such as of the leg), a connector portion 634, a weight 636, and a weight directing mechanism (e.g., pulley) 638. The connector portion 634 can be configured, for example, to include a linkage, a cable, a rope, a wire, etc. that can apply a force from the weight 636, etc. to the pin 632.

Figure 21:
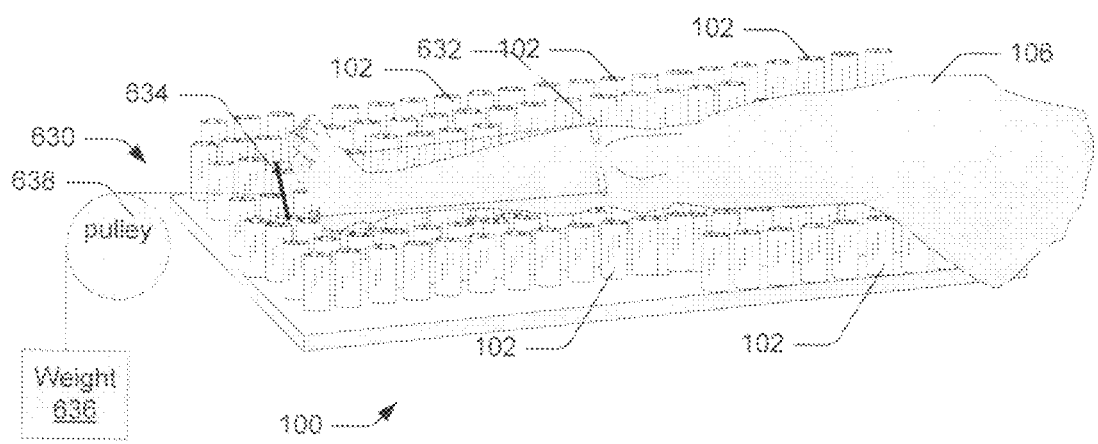
FIG. 21 is a diagram of still another embodiment of the displaceable contouring unit.

The embodiment of the medical displaceable contouring mechanism 100 as described with respect to FIG. 21 can be configured to be a broken away portion of one embodiment of the entire medical displaceable contouring mechanism 100 (such as the leg may be considered a broken away portion of the individual 106), or alternately as an additional embodiment of the medical displaceable contouring mechanism 100 that can operate as a distinct and/or ancillary unit from an embodiment of the medical displaceable contouring mechanism 100 that could support the remainder of the individual 106. The particular traction mechanism as illustrated is intended to be illustrative in nature and not limiting in scope, but it should be noted that certain embodiments of the medical displaceable contouring mechanism 100 can be configured with a variety of accessories that are intended and configured to interact with the one or more displaceable contouring unit(s) 102 relative to the individual 106. As such, certain casts, traction devices, supports, pillows, access ports, etc. can be configured in certain embodiments of the medical displaceable contouring mechanism 100 distinctly as appropriate for that particular individual, and injury or illness.

A number of the embodiments of the medical displaceable contouring mechanism 100 as described with respect to FIGS. 1 to 21 may be configured to allow the one or more displaceable contouring unit(s) 102 to displace with respect to each other, as well as other portions of the medical displaceable contouring mechanism 100, to thereby improve the support of the individual 106. Based at least in part on the positioning of the displaceable contouring unit(s) 102, the variations in pressure, as applied between different ones of the displaceable contouring unit(s) 102, can thereby be reduced thereby potential a generally enhancing blood circulation or flow within the individual 106.

Figure 22:
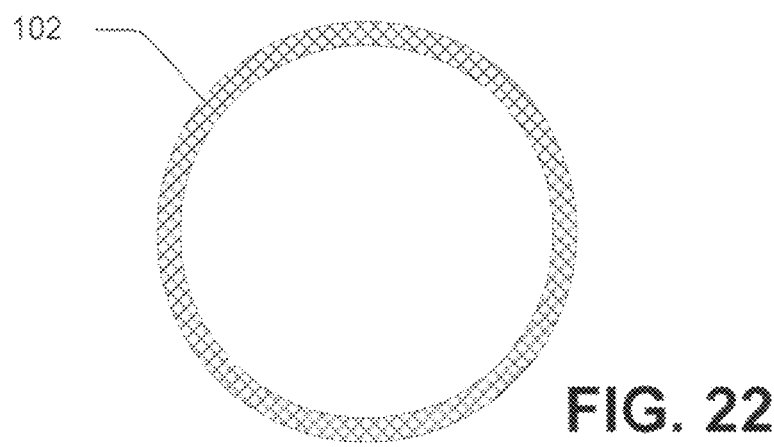
FIG. 22 is a cross-sectional diagram of another embodiment of one of the displaceable contouring unit(s)
Figure 23:
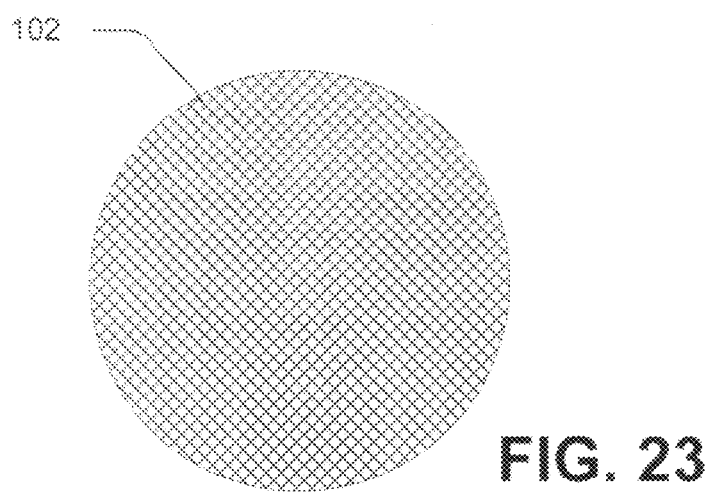
FIG. 23 is a cross-sectional diagram of yet another embodiment of one of the displaceable contouring unit(s)
Figure 24:
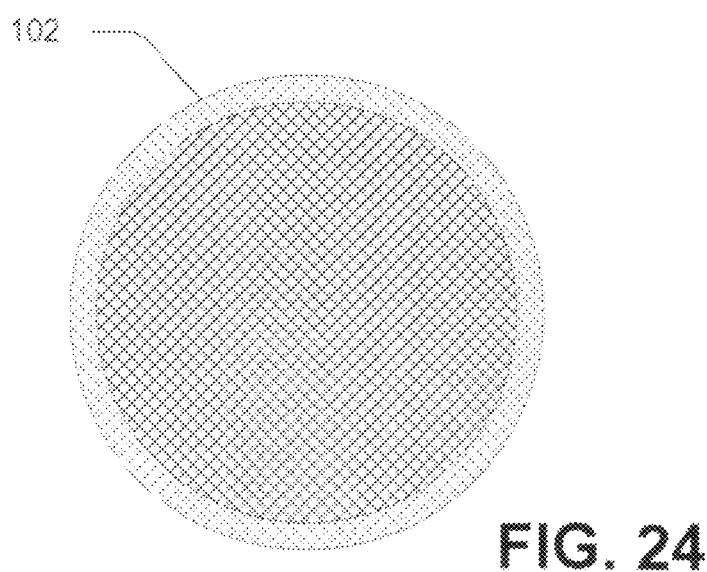
FIG. 24 is a cross-sectional diagram of yet another embodiment of one of the displaceable contouring unit(s)

There can be a variety of configurations of the one or more displaceable contouring unit(s) 102, as described in this disclosure. For example, FIGS. 22, 23, and 24 illustrate different embodiments of the one or more displaceable contouring unit(s) 102. Within certain embodiments of the medical displaceable contouring mechanism 100, at least certain ones of the one or more displaceable contouring unit(s) 102 can vary in configuration. For example, certain ones of the one or more displaceable contouring unit(s) 102 that might be used for such embodiments of the medical displaceable contouring mechanism 100 such as a stretcher, a ski patrol toboggan, or other transitory or stationary embodiments, can be configured to support at least certain portions of the individual such as to reduce pressure differential across the portion. By comparison, other ones of the one or more displaceable contouring unit(s) 102 that might be used for such embodiments of the medical displaceable contouring mechanism 100 can be configured to stabilize at least certain portions of the individual, such as to limit lateral motion therein.

In addition, certain embodiments of the one or more displaceable contouring unit(s) 102, as described in this disclosure, can be configured differently along its length. For example, a first portion of one or more displaceable contouring unit(s) 102 may be used to secure itself to a frame, for example. By comparison, another portion of one or more displaceable contouring unit(s) 102 may be used to rigidify the one or more displaceable contouring unit(s) 102 against tipping or deformation against axial loads, and as such may be relatively stiff. Still another portion of one or more displaceable contouring unit(s) 102 may be used to limit lateral travel of the individual past that one or more displaceable contouring unit(s), and as such may be configured softly as to limit painful contact with the individual. Still another portion of one or more displaceable contouring unit(s) 102 may be used to support the individual on the one or more displaceable contouring unit(s), and as such may be deformable as to act as a cushion. As such, certain embodiments of the medical displaceable contouring mechanism 100 can provide substantial stiffness, such as may be desirable with operating tables, casts, braces, etc.; while limiting excessive pressure against any particular location on the individual, particularly the pressure points.

Certain embodiments of the medical displaceable contouring mechanism 100 can be configured and/or designed for a particular use. For instance, certain hospital bed configurations (where the individual rests) may be more flexible and/or cushioned than certain operating table configurations (where the individual is positioned to be operated on, often in a medicated condition). Similarly, certain cast embodiments of the medical displaceable contouring mechanism 100, which are intended to heal a broken, fractured, or injured bone or joint, may be configured to be more rigid than certain brace embodiments, which are intended to limit excessive motion of a bruised, sore, or lightly injured joint. As such, the configuration of the certain embodiments of the medical displaceable contouring mechanism 100 may be designed or implemented considering the intended operation or functionality of the mechanism.

FIG. 22 shows a cross sectional view of the at least a portion of one or more displaceable contouring unit(s) 102, that is generally hollow in configuration. Depending on design choice or usage, certain embodiments of the one or more displaceable contouring unit(s) 102 can be stiff such as to maintain its cross section, or could alternately be deformable such as to provide cushion along one or more axes. By comparison, the at least a portion of one or more displaceable contouring unit(s) 102 as described with respect to FIG. 23 may be solid in cross section, such as to provide greater structural strength, resistance against bending, and/or integrity.

The at least a portion of one or more displaceable contouring unit(s) 102 as described with respect to FIG. 24 may be solid in cross section, such as to provide greater structural strength, resistance against bending, and/or integrity; but also be coated or cushioned such as to provide improved cushioning. A variety of modifications in designs, material, configuration, use, etc. of certain embodiments of the one or more displaceable contouring unit(s) 102 is considered to be a design choice, but is not intended to be limiting in scope.

The may be a variety of other reasons why it may be desirable to displace at least certain ones of the one more displaceable contouring unit(s) 102, as described in this disclosure. For example, it may be desirable to provide access to certain portions of the individual 106, and thereby may be desirable to remove certain ones of the one or more displaceable contouring unit(s) 102. Additionally, certain ones of the one or more displaceable contouring unit(s) 102 may be directly lined with the wounded area and/or injured portion of the individual 106, and thereby it may be desirable to remove or displace those displaceable contouring unit(s) such as to apply a decreased force to the wounded or injured portion of the individual 106.

Figure 25:
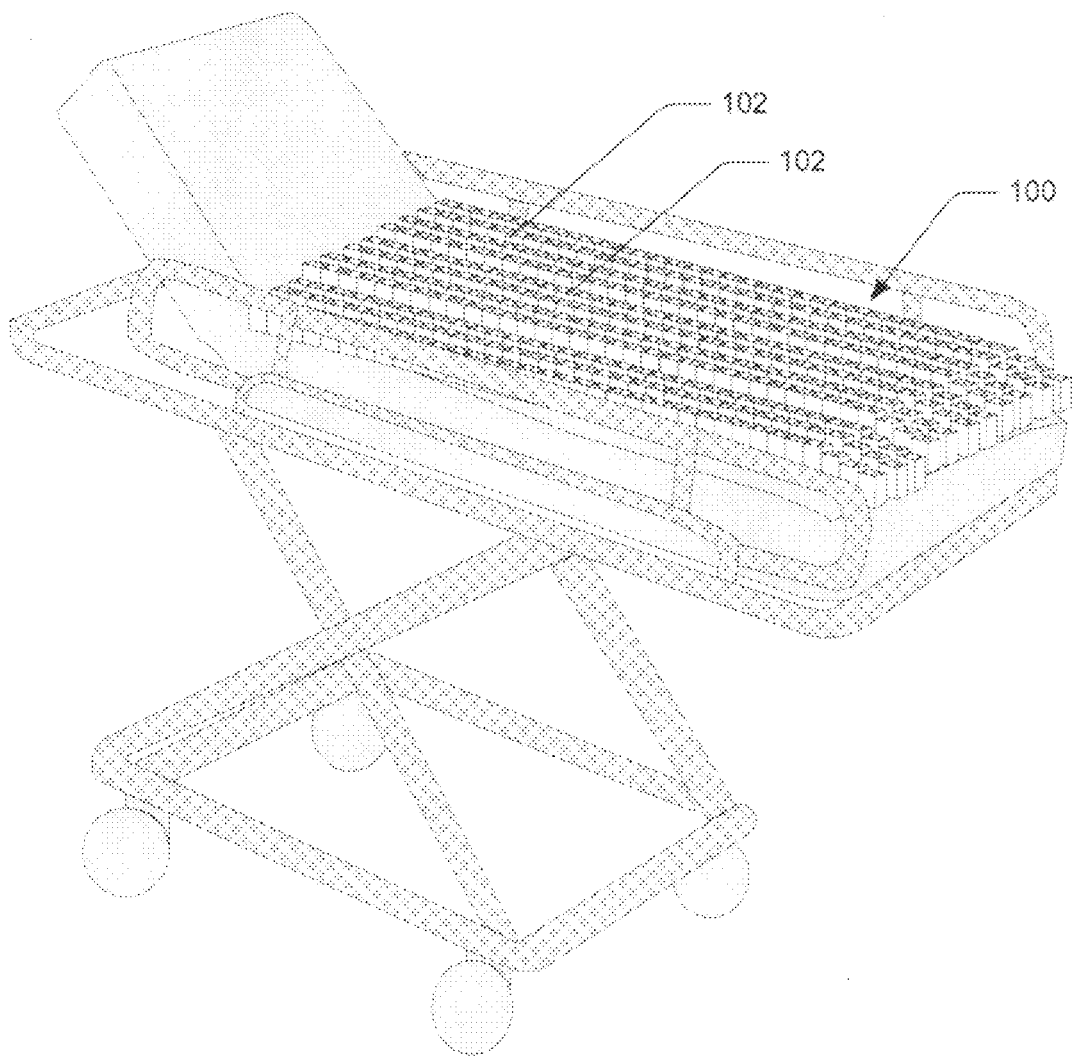
FIG. 25 shows another embodiment of the medical displaceable contouring mechanism.

FIG. 25 shows another embodiment of the medical displaceable contouring mechanism 100 that can be configured with one or more displaceable contouring unit(s) 102. With the embodiment of the medical displaceable contouring mechanism 100 as described with respect to FIG. 25, the one or more displaceable contouring unit(s) 102 can be disposed on a support such as a bed, operating table, cot, frame, table, etc., while still providing a cushioning effect as described in this disclosure. Consider, for example, that certain embodiments of the one or more displaceable contouring unit(s) 102 can be laid upon conventional devices. By comparison, certain embodiments of the one or more displaceable contouring unit(s) 102 can be designed into, or integrated as a part of, certain medical displaceable contouring mechanism 100.

Consider that certain embodiments of the medical displaceable contouring mechanism 100 may be particularly applicable as a rescue mechanism such as for ski patrols, mountaineering, and the like. When the injured individual is positioned in the medical displaceable contouring mechanism 100, at least certain ones of the one or more displaceable contouring unit(s) 102 can be extended upwardly, thereby acting as a stabilizing portion to limit lateral motion of the individual 106 within the stretcher, toboggan, etc. The configuration of the one or more displaceable contouring unit(s) 102 can thereby be displaced such that a considerable number of them extend around, and provide support and/or stabilization, to at least a considerable portion of the individual. Additionally, certain embodiments of the one or more displaceable contouring unit(s) 102 can be configured to provide an insulative aspect, such as may be particularly suitable for winter rescue operations, etc.

Certain embodiments of the one or more displaceable contouring unit(s) 102, as mentioned in this disclosure, can be configured to be situated such as to stabilize at least a portion of the individual 106 (e.g., against motion), as well as be displaced to limit excessive pressure differences as applied to certain portions of the individual 106. Those portions of the embodiments of the one or more displaceable contouring unit(s) 102 that are configured to stabilize the individual 106 can be configured in a variety of different ways. For example, certain embodiments of the one or more displaceable contouring unit(s) 102 can be relatively secure, such that might be suited to limit the individual 106 from performing may displaceable contouring unit(s) permitting, for example, limiting the individual from falling out of the medical displaceable contouring mechanism 100. Other embodiments of the one more displaceable contouring unit(s) can be flexible, inflatable, deformable, etc. such as to enhance the comfort of the individual 106 within the medical displaceable contouring mechanism 100, and/or limited a tendency to reduce blood circulation or flow in the contacting portion of the individual 106, and thereby limited bedsores, aggravation to wounds or injuries, etc.

FIGS. 26 to 29 show a number of embodiments of the medical displaceable contouring mechanism 100 that can be configured with the one or more displaceable contouring unit(s) 102 to set a broken bone, ligament or tendon injury, knee injury, or other condition or injury of the individual 106 in which a portion of the individual should be stabilized, for example. While each embodiment of the medical displaceable contouring mechanism 100 as described with respect to FIGS. 26 to 29 is illustrated as being applied to a leg, it is intended that other embodiments can be applied to arms, knees, spines, elbows, or other joints or bones. Certain embodiments of the medical displaceable contouring mechanism 100 can be configured to act as, augment, or add capability to such conventional stabilizing devices as a cast, a wrap, a brace, etc.

Consider that those individuals, such as humans or animals, who experience a broken bone or certain other significant injury typically: a) may wish to have particular portion(s) of their body stabilized, b) should have those particular portion(s) of their body stabilized, c) may not wish to have any physician, medical personnel, or other person too close or prodding around their injured portion, and d) will likely find the entire experience very painful.

With conventional casts, conventional orthopedic or body braces, and/or other conventional orthopedic or body supports, the physician may attempt to position the broken or injured body part into desired position, such as, for example, to line up bone fragments in a suitable position where they can heal properly. Thereupon, in certain instances, the physician can apply certain of the embodiments of the conventional cast, conventional orthopedic or body brace, and/or other conventional orthopedic or body support while attempting to maintain the body part and/or bone, etc. in the desired position. After the cast is set, or the support is positioned, etc., the individual 106 such as the patient is to wait for the suitable time period for the broken bone or other injury to heal, (while wearing the conventional cast or brace, etc.). During the period of healing, while it may be possible to x-ray the bone, for example, the traditional manner to reposition or reset a broken bone which is not healing properly within a conventional cast is to remove the cast, reset the bone, and replace the cast, which can be expensive, painful, and time consuming for the healing process. After the body portion has been removed from the cast, etc., then the body part can be x-rayed to ensure it has healed, and if not then the bone may have to be re-broken to allow proper healing.

By comparison, certain embodiments of the medical displaceable contouring mechanism 100 can be configured to be applied to the body part (such as a broken arm or leg, for instance) in which the injury has been repositioned, or has been repositioned by the physician. Certain embodiments of the medical displaceable contouring mechanism 100 can be configured to, and be made of materials that allow the body part (such as a broken arm of leg) to be x-rayed. It is likely that such embodiments of the medical displaceable contouring mechanism 100, which are being used in such applications as broken or fractured bones would be made of a material and/or configuration that would allow proper x-ray. Similarly, it is likely that such embodiments of the medical displaceable contouring mechanism 100, which are being used in such applications as can be diagnosed or treated utilizing other electromagnetic radiation sources (e.g., CAT scan, optical scanners or detectors, radiation therapy, etc.) would be made of a material and/or configuration that would allow the proper application of the particular electromagnetic radiation, medication, or other treatment and/or diagnostic tool.

Certain embodiments of the medical displaceable contouring mechanism 100 can be set and/or repositioned after being positioned on the body part, such as by suitable actuation of the one or more displaceable contouring unit(s) 102. In certain embodiments, the displacement of the one or more displaceable contouring unit(s) 102 can act to displace bone ends, fragments, joints, or other such body parts into a desired position (such as is determined following an x-ray, or other diagnostic or treatment mechanism) to enhance and/or improve healing. Even during healing or treatment of the medical displaceable contouring mechanism 100, the one or more displaceable contouring unit(s) 102 can be displaced or otherwise positioned as may be determined by the physician. Certain conventional casts may be solid such as to unmodifiably maintain a portion of the individual (e.g., arm or leg of the individual) after they have been set. By comparison, certain embodiments of the medical displaceable contouring mechanism 100 can be reconfigured such as to displace, reposition, support, stabilize, or apply desired pressure to at least one particular part of the individual, as desired, to suitably treat the individual and/or patient as appropriate. Such treatment of the individual's body part using certain embodiments of the medical displaceable contouring mechanism 100 can thereby apply precise, responsive, and/or accurate displacements and/or pressures, and thereupon provide a suitable responsive treatment, support, stabilization, displacement, etc. in an on-going manner such as to be able to compensate for deviations from the desired recovery.

While the embodiments of the medical displaceable contouring mechanism 100 as described with respect to FIGS. 26-29 may appear relatively skeletal as compared to certain conventional casts or braces, it may also be desired to apply other bracing members, etc. For example, cast material (e.g., plaster of paris) could be applied around to encase certain embodiments of the medical displaceable contouring mechanism 100 of FIGS. 26-29, to provide a more substantial cast appearance and/or limit contact of the injured extremity with other people or surfaces. Certain other metal, plastic, fabric, fiberglass, or other material could be attached to enclose certain portions of certain embodiments of the medical displaceable contouring mechanism 100. As such, the appearance, operating characteristics, and/or structure of certain embodiments of the medical displaceable contouring mechanism 100 can be modified as desired.

Certain embodiments of the medical displaceable contouring mechanism 100 can be configured to stabilize at least a portion of an individual 106, as described with respect to FIGS. 26-29, in which the one or more displaceable contouring unit(s) 102 can be configured to limit the pressure differential applied across at least a portion of the individual as compared with, for example, certain conventional casts. By configuring certain embodiments of the one or more displaceable contouring unit(s) 102, for example, the pressure applied therefrom against the individual can also be reconfigured such as to potentially reduce pressure points and potentially enhance circulation of blood, and other bodily fluids, within the portion of the body to which the medical displaceable contouring mechanism 100 has been applied.

FIG. 27 illustrates a number of the one or more displaceable contouring unit(s) 102 being arranged substantially inwardly towards the body portion (e.g., leg) in a manner that conforms substantially to the contour of the body portion. Though one layer of the one or more displaceable contouring unit(s) 102 is illustrated in FIG. 27, it is envisioned that a number of rows or patterns of the one or more displaceable contouring unit(s) 102 can be established to provide the desired support.

Certain embodiments of the medical displaceable contouring mechanism 100 can be configured with variety of stabilizing devices 2860, such as may conform to the general pattern or contour of the individual 106. Consider, for example, that certain embodiments of the stabilizing device 2860 may include a contour conforming portion 2862 which as combined with the one or more displaceable contouring unit(s) 102 can effectively stabilize the leg relative to the configuration of the contour conforming portion 2862. Additionally, certain embodiments of the stabilizing device 2860 can include a connecting element 2864, which are configured to extend between adjacent ones of the contour conforming portion 2862 and maintain the relative positions of the contour conforming portion 2862. By maintaining the relative positions of the contour conforming portion 2862, as well as by stabilizing the leg relative to the contour of the contour conforming portion 2862, the relative motion of the different portions of the body portion can be limited, thereby allowing the bone and/or joint to heal.

Certain embodiments of the contour conforming portion 2862 can have a variety of configurations and can be formed from a variety of materials depending on such aspects as strength and size of the individual, type of injury or wound, whether the medical displaceable contouring mechanism 100 should be removable, etc. Certain embodiments of the one or more displaceable contouring unit(s) 102 could be extendable inwardly with respect to the contour conforming portion 2862 such as to create a shape that can conform with the contour of the body portion. Certain embodiments of the contour conforming portion 2862 can be configured to be removable or displaceable, such as by displacing the one or more displaceable contouring unit(s) 102 outwardly to provide a clearance between the contour conforming portion 2862 and the body part. As such, certain embodiments of the contour conforming portion could be cleaned, removed, etc. Strength can be maintained in certain embodiments of the medical displaceable contouring mechanism 100 by providing certain embodiments of the contour conforming portion of metal, plastic, fiberglass, composite, honeycomb, or other suitable material. If desired, certain embodiments of the contour conforming portion 2862 could also be constructed at least partially from a similar material as conventional casts, etc., and could also be constructed to be waterproof, breathable, or have other characteristics based at least in part on the design.

Certain embodiments of the one or more displaceable contouring unit(s) 102 of the contour conforming portion 2862 can be configured to be washed, disinfected, or otherwise cleaned. The inside of conventional casts typically can become quite dirty, or can even represent a health problem. By providing an embodiment of the medical displaceable contouring mechanism 100 including one or more displaceable contouring unit(s) 102 that can be cleaned represents a considerable hygienic or sanitary improvement.

Certain embodiments of the one or more displaceable contouring unit(s) 102 within the contour conforming portion 2862 can even be actuated by the individual and/or an assistant. Consider that certain embodiments of the medical displaceable contouring mechanism 100 can thereby be controlled as to ensure comfort to the individual, even if remote from the doctor, hospital, etc. Certain embodiments of the medical displaceable contouring mechanism 100 can be configured such that if the individual may want to loosen it during rest, cleaning, or other activity, then it can be performed and perhaps returned to the original or even another configuration later.

Certain embodiments of the medical displaceable contouring mechanism 100 can even act to alter its position to adequately treat the individual. Certain broken bones, fractures, etc., may be set in an originally improper position. After the physician or other medical personnel determines, for example, that the medical displaceable contouring mechanism 100 is configured improperly, then at least certain ones of the one or more displaceable contouring unit(s) 102 can be positioned or displaced, in effect forcing the bone or joint into the desired position. Certain embodiments of the one or more displaceable contouring unit(s) 102 can be configured to act with the desired precision such as to ensure proper positioning or healing of the bones and/or joints of the individual, etc.

Figure 28:
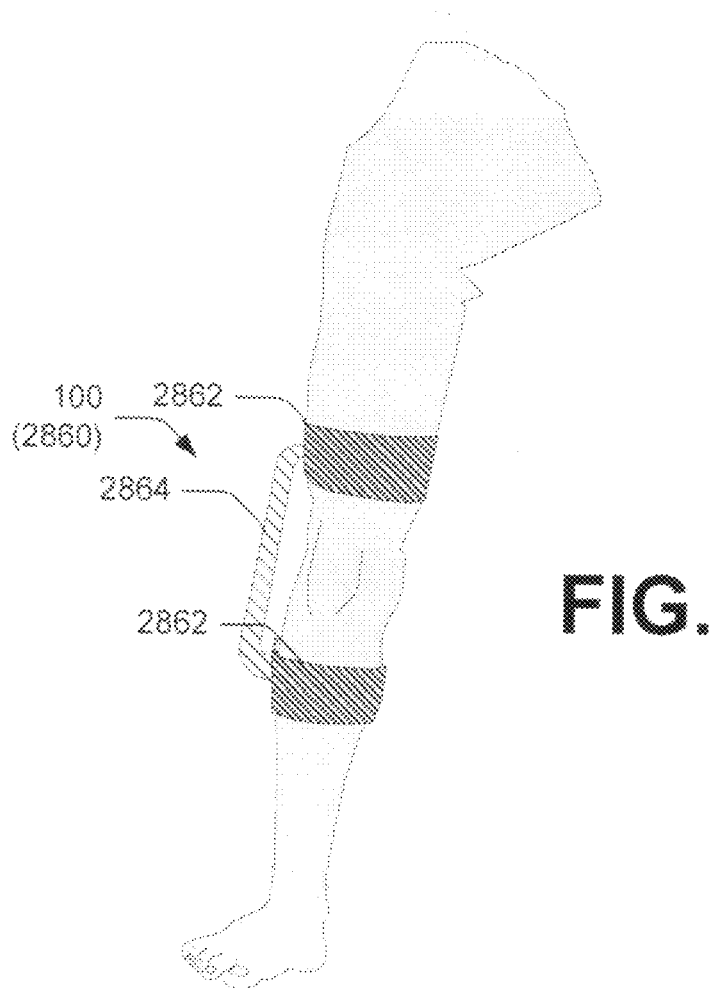
FIG. 28 shows a diagram of another embodiment of the medical displaceable contouring mechanism that can be configured to at least partially stabilize at least a portion of the individual.

Certain embodiments of the connecting element 2864, as described with respect to FIGS. 26 to 28, can be made of sufficiently strong material such as a metal, plastic, fiberglass, composite, etc., such as to relatively secure and/or position the at least one contour conforming portion 2862. As such, certain embodiments of the stabilizing device 2860, including the contour conforming portion 2862 and/or the connecting element 2864, can be quite rigid and can effectively stabilize different portions of the body portion such as an arm, spine, or leg, for example. Certain embodiments of the stabilizing device 2860, including the contour conforming portion 2862 and/or the connecting element 2864 can also be constructed and/or designed to be relatively light, and thereby limit excessive force having to be applied by the individual (human or animal) in having to carry the stabilizing device about. As such, certain embodiments of the stabilizing device 2860 can be configured to act as and/or stabilize the individual in a similar manner as a conventional cast, but living can be made considerably easier for those who have to wear the stabilizing device 2860.

The amount of stabilization of the bone and/or joint being stabilized can effect the design of certain embodiments of the stabilizing device 2860. Consider, for example, that FIG. 28 shows a briefer stabilizing device 2860 than that of FIG. 26, and as such might be appropriately applied to a less severe wound or injury, or one in an area that is easier to support.

Figure 29:
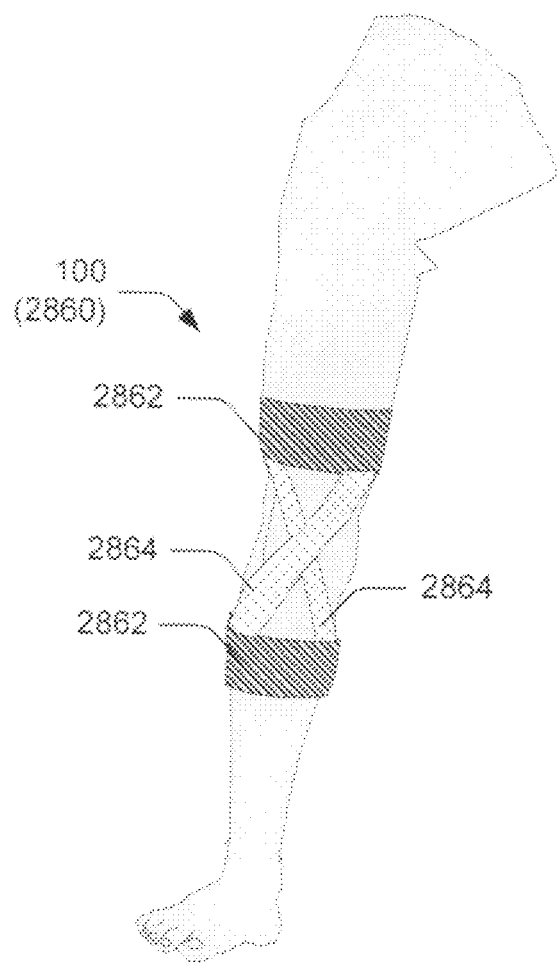
FIG. 29 shows a diagram of an embodiment of the medical displaceable contouring mechanism that can be configured to at least partially stabilize at least a portion of the individual.

Additionally, certain embodiments of the stabilizing device 2860 can be configured or act as a brace as described with respect to FIG. 29, instead of a rigid cast, for example. Certain embodiments of the stabilizing device 2860 can be designed or improved to deal with a particular stabilization of the individual. As such, certain embodiments of the connecting element 2864 can be configured as strap members, etc., instead of as solid frame members, etc. Those skilled in the orthopedic and/or surgical arts will understand the variety of embodiments of the stabilizing device 2860 that can be applied to a variety of individuals for particular purposes.

The embodiments of the stabilizing device 2860, as described with respect to FIGS. 26 to 29, can be configured to be applied to individuals in a hospital, nursing home, clinic, etc.; or alternately can be configured to be applied to individuals at home, capable of traveling outside, etc. As such, certain embodiments of the stabilizing device 2860 (which itself can be considered an embodiment of the medical displaceable contouring mechanism 100), can be configured to be integrated into or act as an accessory to other embodiments of the medical displaceable contouring mechanism 100 as described with respect to FIGS. 1 to 25, for example. As such, certain embodiments of the medical displaceable contouring mechanism 100 that are configured as casts, braces, traction, etc., can be integrated as a portion of another embodiment of the medical displaceable contouring mechanism 100 that is configured as a hospital bed, stretcher, operating table, etc., as described in this disclosure.

Certain embodiments of the medical displaceable contouring mechanism 100 can be configured to provide a time dynamic quality to how pressure is applied to various points in the body from the one or more displaceable contouring unit(s) 102. For example, consider a patient being situated on a bed, such that certain of the displaceable contouring unit(s) 102 can be configured to support more pressure and/or weight of the individual than others, (pelvis and right shoulder). After a period of time the primary sites of support may, for example, be shifted to other regions (such as the left shoulder and thighs). Thus, there may be situations when certain sites in the body may be exposed to reduced or varying amounts of pressure for therapeutic, healing, or other reasons.

Certain embodiments of the medical displaceable contouring mechanism 100 can be configured to assist in such illustrative conditions as the reduction of the formation of blood clots in the veins of the legs (known as Deep Venous Thrombus, or DVT). For example, certain embodiments of the displaceable contouring unit(s) 102 of the medical displaceable contouring mechanism 100 can be displaceable to provide a "rhythm wave" or other similar motions under the legs, which has been shown to induce movement of venous blood back towards the heart. This motion of certain of the displaceable contouring unit(s) 102 would reduce the risk of venous stasis (blood pooling in the legs) and the potential subsequent formation of blood clots. Such formation of blood clots can be life threatening or debilitating due to the fact that they can migrate to the lungs after their formation and can cause serious pulmonary complications and/or death.

Figure 30:
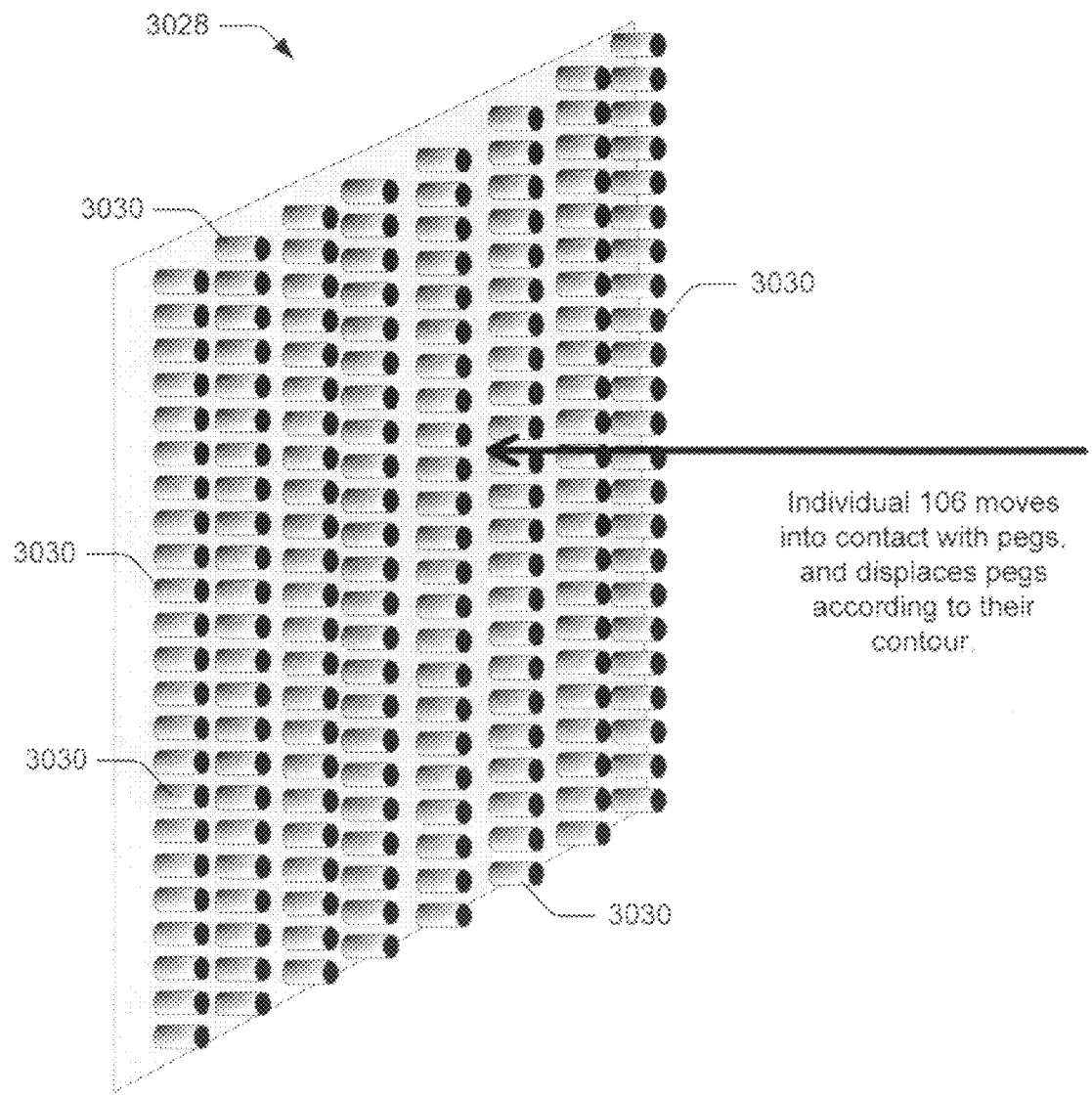
FIG. 30 is a diagram of one embodiment of a contour detector.

There are a variety of mechanisms that can be used to determine how to position the displaceable contour unit(s) 102. FIG. 30 shows an embodiment of a contour detector 3028, which can be used to determine a contour of the individual. During operation, the individual can move into physical contact with and/or displace at least certain ones of an array of pegs 3030, or vice versa. Based, at least in part on the contour of the individual, at least certain ones of the array of pegs 3030 can be displaced to reflect the contour. Each peg 3030 can be spring biased, and can include displacement sensor (not shown) to detect the displacement of the pegs. Certain embodiments of the detection sensor can include a mechanical displacement sensor such as a viewable scale, an electromechanical displacement sensor, a computerized displacement sensor, a controllable displacement sensor, an optical displacement sensor, and/or other suitable displacement sensors such as to determine the displacements of the pegs 3030 across the array.

FIG. 30, for example, illustrates one embodiment of the contour detector 3028 formed from a number of pegs 3030 that can be applied to the individual 106. Certain embodiments of the pegs 3030 can be spring biased, while other embodiments may not be. As the peg-based embodiment of the contour detector 3028 is generally biased against the individual 106, those pegs 3030 that come in contact with the individual 106 will be displaced by a distance substantially corresponding to the configuration of the individual 106 at the location of the peg. Certain embodiments of the contour detector 3028 are configured with displacement qualifiers 706, which may detect the displacement of the peg as it comes in contact with the individual 106. Based at least partially upon the displacement of the pegs 3030 upon contact with the individual 106, certain embodiments of the displaceable contouring unit(s) 102 can be displaced at a corresponding distance within certain embodiments of the medical displaceable contouring mechanism 100. Such displacement can utilize a variety of mechanical, electromechanical, electronic, wireless, processor-based, computer-based, mote-based, or other suitable mechanism. As such, the placement of certain embodiments of the one more displaceable contouring unit(s) as described with respect to FIGS. 1 to 29 can be derived at least in part based on a determination of the contour and certain embodiments of the contour detector 3028 as described with respect to FIG. 30.

Another embodiment of the contour detector 3028 can include an electromagnetic radiation distance detector 3050, by which a scan of the individual can be utilized to determine the shape and/or contour of the individual. Certain embodiments of the electromagnetic radiation distance detector 3050 can operate at least partially by reflecting, deflecting, or otherwise returning an original set of beams off the individual at the location of the contour, and by determining the time for each one of the set of beams to return. The distance to that portion of the contour (and thereby the contour itself) of the at least a portion of the individual can be determined at least in part by the determining the time for each one of the set of beams to return.

Figure 31:
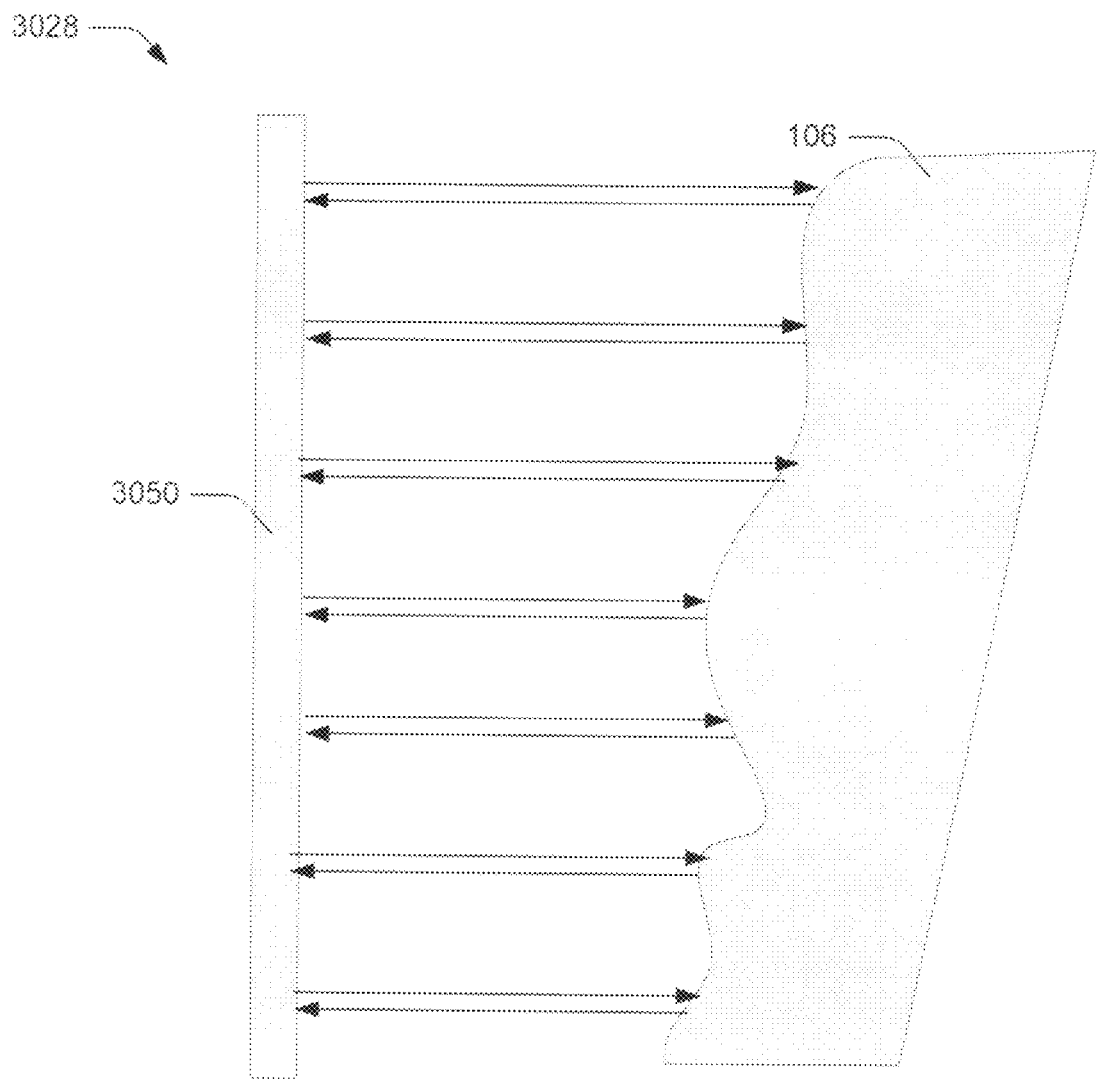
FIG. 31 is a diagram of another embodiment of the contour detector.

By using the different embodiments of the contour detector 3028, as described with respect to FIGS. 30 and 31, to determine the contour of the individual; the position of the one or more displaceable contouring unit(s) 102 of the medical displaceable contouring mechanism 100 can thereupon be adjusted at least based in part on the contour. Consider, for example, that each hospital or nursing home can include at least one contour detector, at least certain ones of the medical displaceable contouring mechanism 100 can be adjusted to at least partially conform to the contour of the individual. As such, at least some medical displaceable contouring mechanism 100 such as hospital beds, operating tables, casts, braces, etc. can be contoured according to the contour of at least a portion of each respective individual.

It may, therefore, be desirable to approximate the relative positioning of certain embodiments of the one or more displaceable contouring unit(s) 102 to substantially conform to, or mirror, a content of the individual 106 in that region. For example, a portion of the one more displaceable contouring unit(s) 102 that are intended to be configured to support the torso of the individual 106 might be expected to be displaced to substantially conform to the content of the torso of the individual 106. A variety of embodiments of a contour detector 3028 are now described with respect to FIGS. 30 to 31.

FIG. 30 therefore can show an embodiment of the contour detector 3028 that can include an array of spring-biased pegs 3030, that can be biased against the portion of the individual 106, and can indicate the biasing force of spring biased pegs as well as the deflection of the spring biased pegs. By determining the deflection of, in combination with the force as applied to, the spring biased pegs 3030, it came be determined how much each spring biased pegs should be deflected to limit the relative force applied to corresponding ones of the displaceable contouring unit(s) 102.

There are a variety of other embodiments of the contour detector 3028 that can be utilized to determine the contour of at least a portion of the individual 106, and thereby determine suitable displacement of the displaceable contouring unit(s) 102. For example, FIG. 31 shows another embodiment of the contour detector 3028 that emits electromagnetic radiation of certain suitable types, and based on reflectance or other distortion of the electromagnetic radiation from the individual 106, can determine the a contour image of the at least a portion of the individual. Examples of the electromagnetic radiation that can be utilized to include, but not limited to, sound, light, infrared, ultraviolet, visible light, etc. Certain embodiments of the contour detector 3028 can be array-based, and as such can transmit and receive the electromagnetic radiation at a limited area of the individual 106. The configuration and/or dimensions of the array configuration represents a design choice, which should not be limiting.

Certain embodiments of the medical displaceable contouring mechanism can also be configured to be operated manually, such that a person can adjust the relative position of the one or more displaceable contour unit(s) 102 to contour to the individual. Such adjustments can also be automated, such as by those displaceable contour unit(s) that are experiencing a considerably greater pressure than others (as the individual rests thereupon) perhaps being moved away from the individual compared to the others, such as to reduce pressure differentials across multiple displacement contour unit(s) 102, for example. Such pressure-sensitive positional-adjustments of the displaceable contour unit(s) can be performed as frequently or infrequently as desired, and can, for example, allow adaptation to the contour of the individual as the individual rolls or moves. Certain embodiments of the medical displacement contouring controller can be used to adjust the positions of displaceable contour unit(s) 102.

Figure 32:
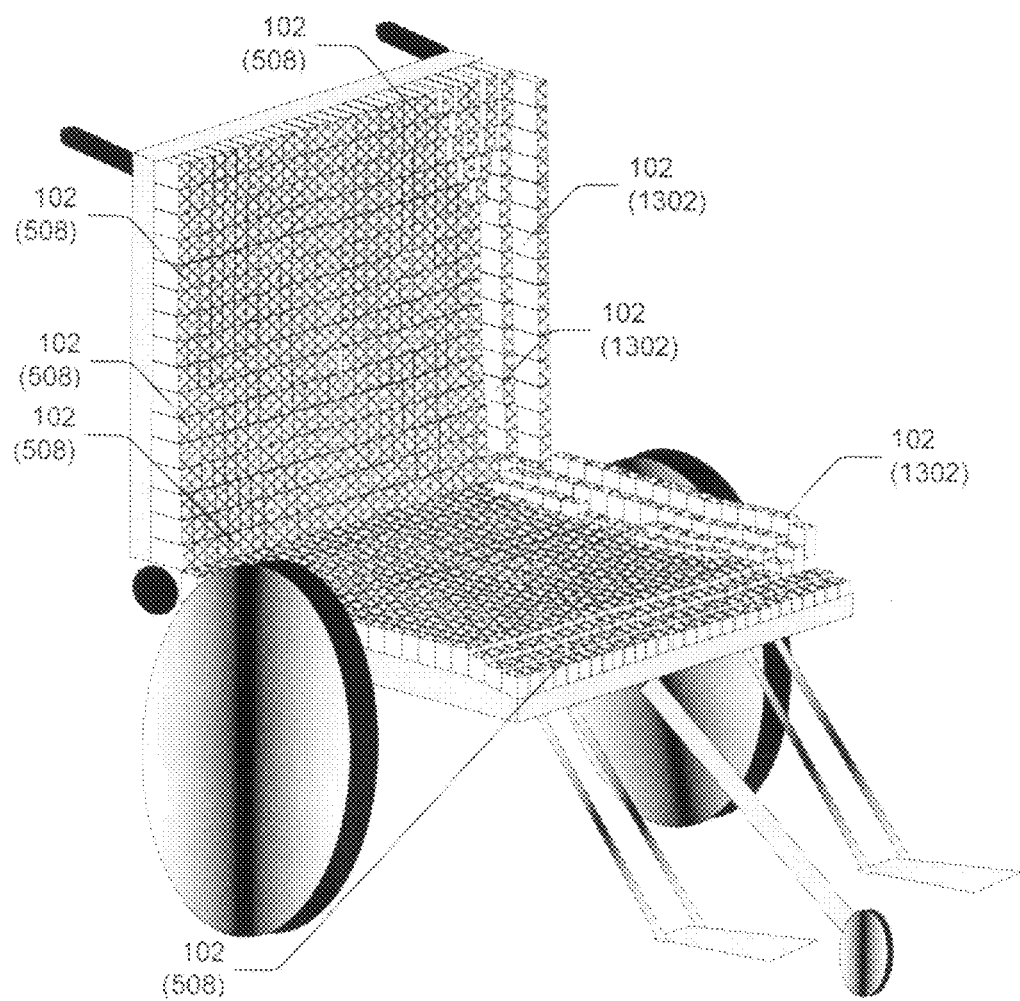
FIG. 32 is a diagram of another embodiment of the medical displaceable contouring mechanism.

FIG. 32 shows another embodiment of the medical displaceable contouring mechanism 100 including the one or more displaceable contouring unit(s) 102 that can be configured as a wheelchair. As illustrated in FIG. 32, certain ones of the one or more displaceable contouring unit(s) 102 may be displaced, either such that certain ones of the conformable portion 508 provide a contoured support for the appropriate body portion of the individual, or alternately such that certain ones of the stabilization surfaces can limit motion of the individual in that direction. For example, as described with respect to FIG. 32, those portions of the one or more displaceable contouring unit(s) 102 that are under the individual will likely be relatively displaced to adjust to the contour of the individual, and thereby limit excessive pressure, pressure points, formation of blisters or bed sores, etc., that may result therefrom.

Certain of those one or more displaceable contouring unit(s) 102 that are to the right of the wheelchair medical displaceable contouring mechanism 100, as described with respect to FIG. 32, are illustrated in their raised position, and as such will provide the stabilization surface 1302 to limit excessive or undesired lateral motion in that direction by the individual. In addition, certain embodiments of the stabilization surface can be configured to cushion against impact by the individual in that direction. For ease of illustration, those embodiments of the displaceable contouring unit(s) 102 to the left in FIG. 32 that could be raised to provide the stabilization surface 1302 are not illustrated in their raised position, for ease of illustration.

While this disclosure describes a number of embodiments of displaceable contouring unit(s) 102 that can be displaced to conform to a contour of a part of the individual, it is also possible that certain embodiments of the displaceable contouring unit(s) 102 can be constructed of appropriate dimensions such as to conform thereto. As such, with certain embodiments of the medical displaceable contouring mechanism 100 that may be designed for use by a particular person, it may be desirable, and indeed more economical, to fabricate the medical displaceable contouring mechanism 100 with multiple displaceable contouring unit(s) 102 having different dimensions, configurations, spring factors, characteristics, etc.

Certain embodiments of the medical displaceable contouring mechanism 100, such as the wheelchair embodiment as described with respect to FIG. 32, can be configured to such each one of the conformable portion 508 that comes in contact with the individual can apply a force in a direction substantially corresponding to the axis of the displaceable contouring unit(s) 102. As such, the individual will not feel "wedged" between certain parts of the material of the displaceable contouring unit(s) 102, and instead will likely feel strongly supported. By maintaining this uniform support of the individual within certain embodiments of the medical displaceable contouring mechanism 100, certain stresses and/or forces that may be applied to bones, joints, skin, organs, etc. by such embodiments of the medical displaceable contouring mechanism 100 as a wheelchair may be limited.

There can be a variety of configurations of the one or more displaceable contouring unit(s) 102, as described in this disclosure. For example, certain embodiments of the displaceable contouring unit(s) 102 can include a unit displacement portion 3502, as described with respect to FIG. 33. Consider, for example, that certain embodiments of the unit displacement portion 3502 can provide structural support for the displaceable contouring unit(s) 102, and can even be displaced upwardly or downwardly using such illustrative mechanisms as a rack and pinion, telescoping member, fluid actuated element, hydraulic element, pneumatic element, etc. As such, certain embodiments of the stabilization surface 1302 may not extend uniformly for the entire length of the displaceable contouring unit(s) 102 (as described with respect to FIG. 13 and other locations, for example). Instead, only those portions of the displaceable contouring unit(s) 102 which comes in contact with the individual may be configured as the stabilization surface 1302, as described in this disclosure. By comparison, other portions of the displaceable contouring unit(s) 102 may be provided with a suitably functional embodiment of the unit displacement portion 3502.

Certain embodiments of the displaceable contouring unit(s) 102 that do not include the stabilization surface 1302 may still be provided with certain embodiments of the unit displacement portion 3502. For instance, as described with respect to FIG. 34, certain embodiments of the conformable portion 508 (which may be pivotable or not) may attach to the unit displacement portion 3502 either directly or via the joint member 516. As such, the complexity and/or associated expense of certain embodiments of the displaceable contouring unit(s) 102 can be varied among certain embodiments of the medical displaceable contouring mechanism 100.

Certain embodiments of the displaceable contouring unit(s) 102 can include the conformable portion 508 which can be configured either as only the conformable portion, or a combination of the conformable portion and the stabilization surface 1302. The embodiment of the displaceable contouring unit(s) 102 as described with respect to FIGS. 35 and 36 can include the unit displacement portion 3502 which is configured in the shape of a "J", as well as drive rollers 3504, and a stop 3506. The embodiment of the displaceable contouring unit(s) 102 when in its lowered position, as described with respect to FIG. 35, can be displaced slightly upwardly or downwardly by the drive rollers 3504 such as to conform somewhat to the contours of the individual, as described with respect to FIGS. 1 to 3, and other locations. During this initial displacement, the conformable portion 508 to remain substantially parallel to its original orientation.

As the drive rollers 3504 continue to drive the unit displacement portion 3502 upwardly, the drive rollers encounter the curved portion of the unit displacement portion 3502. As such, the unit displacement portion 3502, as well as the connected conformable portion 508, is rotated through a desired angle (e.g., 90°), such as to be able to contact the individual from another angle, for example. Consider that this surface that is configured as the conformable portion 508 can be alternately configured as the stabilizing portion 1302, since it can stabilize against lateral motion of the individual in the direction opposed by the conformable portion 508.

Figure 33:
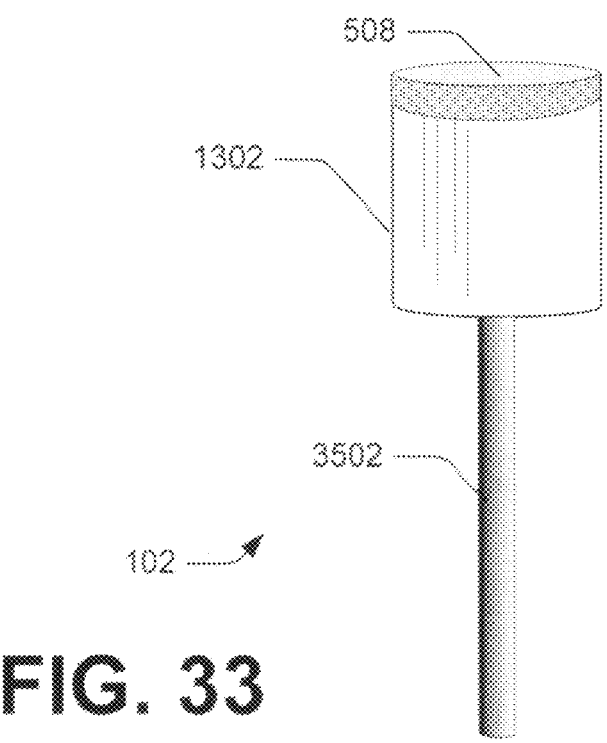
FIG. 33 is a diagram of another embodiment of the displaceable contouring unit.
Figure 34:
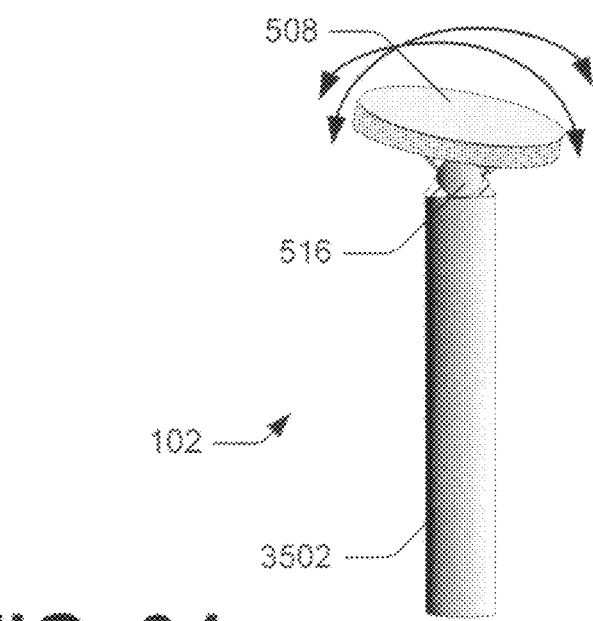
FIG. 34 is a diagram of yet another embodiment of the displaceable contouring unit.
Figure 35:
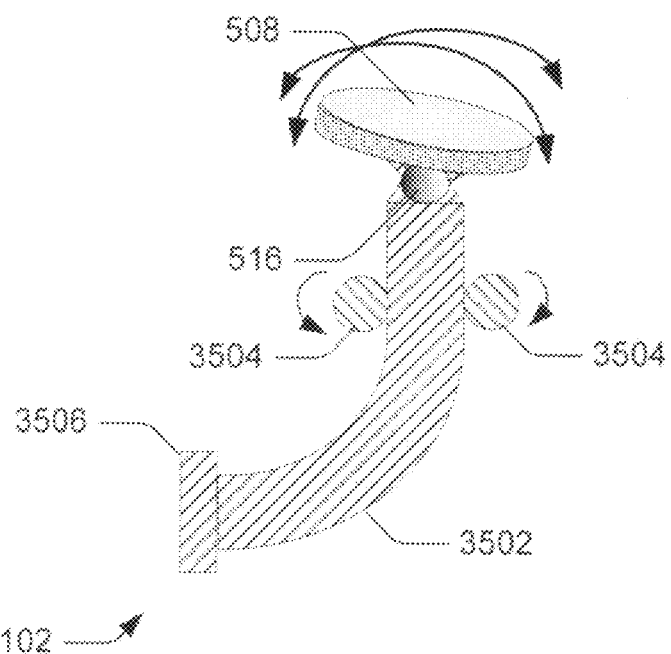
FIG. 35 is a diagram of still another embodiment of the displaceable contouring unit in an un-extended position.
Figure 36:
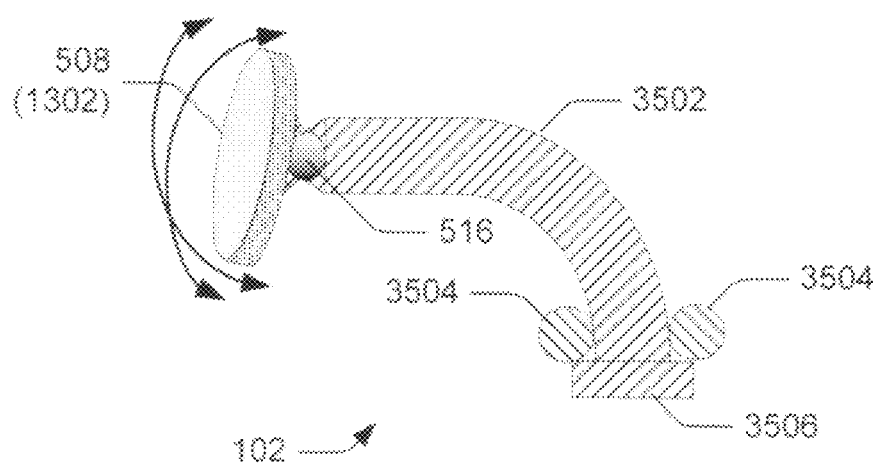
FIG. 36 is a diagram of the embodiment of the displaceable contouring unit of FIG. 35 in an extended position.

There may be a variety of configurations for certain embodiments of the unit displacement portion 3502, and the associated elements, as described in this disclosure. For example, the embodiment of the unit displacement portion 3502 as described with respect to FIGS. 33 and 34 are rod-like; while the embodiment of the unit displacement portion 3502 as described with respect to FIGS. 35 and 36 are bar-like. The particular configuration of the unit displacement portion 3502 represents a design choice, and may be factored by such considerations as applied stresses, appearance, function, applied force, operative characteristics, etc.

Figure 37:
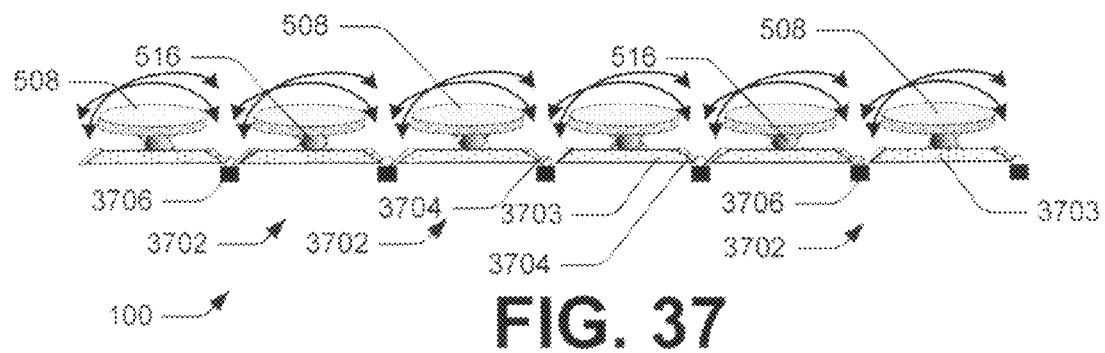
FIG. 37 is a diagram of another embodiment of the medical displaceable contouring mechanism.

Certain embodiments of the medical displaceable contouring mechanism 100, as described with respect to FIG. 37, can include a number of link portions 3702 that allows positioning of certain displaceable contouring unit(s) 102 such as to conform to the contour of the individual. Certain embodiments of the link portions 3702 can include, but not limited to, a link 3703, a hinge 3704, a link angle control 3706, and one or more of the displaceable contouring unit(s) 102. Certain embodiments of the link 3703 can be configured to provide a mounting surface for the respective displaceable contouring unit(s) 102 associated with that link. Certain embodiments of the displaceable contouring unit(s) 102 can be connected to the link 3703 using, for example, the connector portion 516 can thereby allow relative pivoting motion of the conformable portion 508, as also described in this disclosure with respect to FIG. 8, and other locations in this disclosure.

Certain embodiments of the hinge 3704, for example, can be configured to allow relative rotation of adjacent link portions 3702. As such, certain embodiments of the links 3703 (as well as the respective link portions 3702) can be configured to approximately follow the contour of the individual 106, as described with respect to FIG. 38, based at least in part on the displacement in the hinge(s) 3704. In certain embodiments, each hinge 3704 can have one of its respective hinge portions be attached to its respective links 3703, thereby allowing relative to pivoting about the hinge 3704 of the respective links 3703, as well as the respective link portions 3702.

Certain embodiments of the link angle control 3706 can be associated with the respective hinge 3704; and can be configured to control the position and/or motion of its respective hinge 3704. Certain embodiments of the link angle control 3706 can be mechanical-based, electrical-based, electromechanical-based, computer-based, controller-based, and/or a variety of configurations. Certain embodiments of the medical displaceable contouring controller 97, as described in this disclosure with respect to FIG. 4, can include and/or provide the operations of the link angle control 3706. Certain embodiments of the link angle control 3706 can be mechanically ratchet-based, such as to allow rotation in one angular direction of each respective link portion 3702, while limiting rotation in the reverse direction. As such, certain embodiments of the link angle control 3706 can allow at least a portion of the medical displaceable contouring mechanism 100 to be rotated about the individual, and remain in position relative to the individual. While in this position, certain ones of the conformable portion 508 can be biased at a desired angle against the individual 106, in such manner as to provide support to, and/or stabilize, at least a portion of the individual considering the contour of that individual.

Certain embodiments of the link angle control can be automated, such as to be able to secure the individual 106 in such a manner that each of the displaceable contouring unit(s) 102 is positioned correctly and/or configured to apply a suitable distributed pressure. In certain embodiments, the position of each displaceable contouring unit(s) 102 can be modified somewhat (e.g., if the individual is being rolled over).

Certain embodiments of the medical displaceable contouring mechanism 100 can be configured, positioned, and/or operated by medical assistant and/or technician who are assisting the position, for example. Consider an operating room scenario, in which the individual 106 such as a patient is brought into the operating room, and moved onto the medical displaceable contouring mechanism 100. In certain instances, the individual 106 can be anesthetized, and then the medical assistant and/or technician can position the medical displaceable contouring mechanism 100 suitably based upon the desired operation. During certain times, the individual may be repositioned, such as may be the case if the physician wants to access the back or side of the individual. During these periods, certain embodiments of the medical displaceable contouring mechanism 100 can be rotated, or positioned, suitably to allow the desired access to the individual.

Certain embodiments of the medical displaceable contouring mechanism 100 can be configured such that their displaceable contouring unit(s) 102 are suitably directed or positioned such as to provide suitable support and stabilization to at least portions of the individual during their potential repositioning and/or rotation that may occur during an operation.

Figure 38:
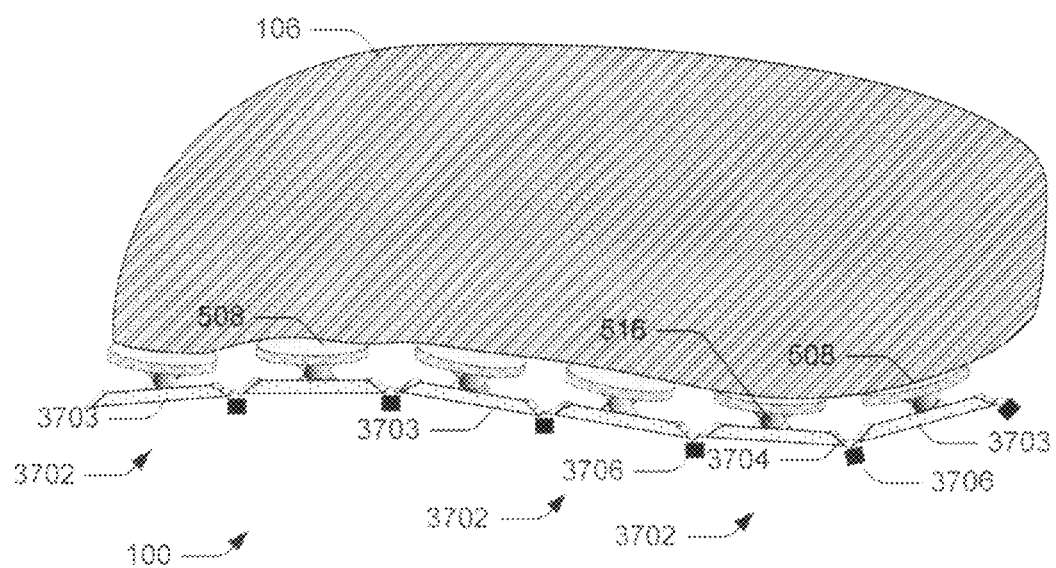
FIG. 38 is a diagram of the embodiment of the medical displaceable contouring mechanism of FIG. 37 being positioned relative to a contour of the individual.
Figure 39:
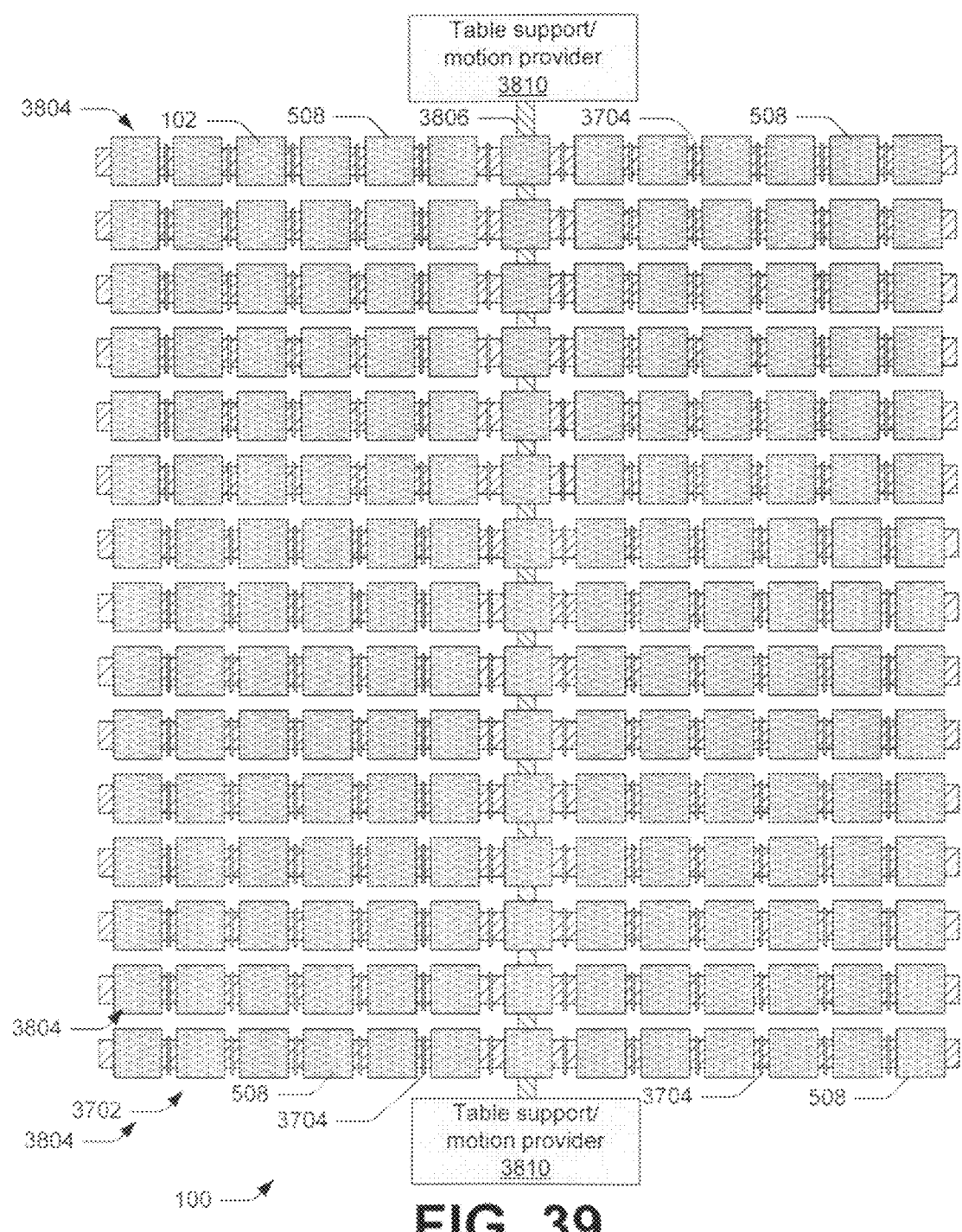
FIG. 39 is a diagram of another embodiment of the medical displaceable contouring mechanism.
Figure 40:
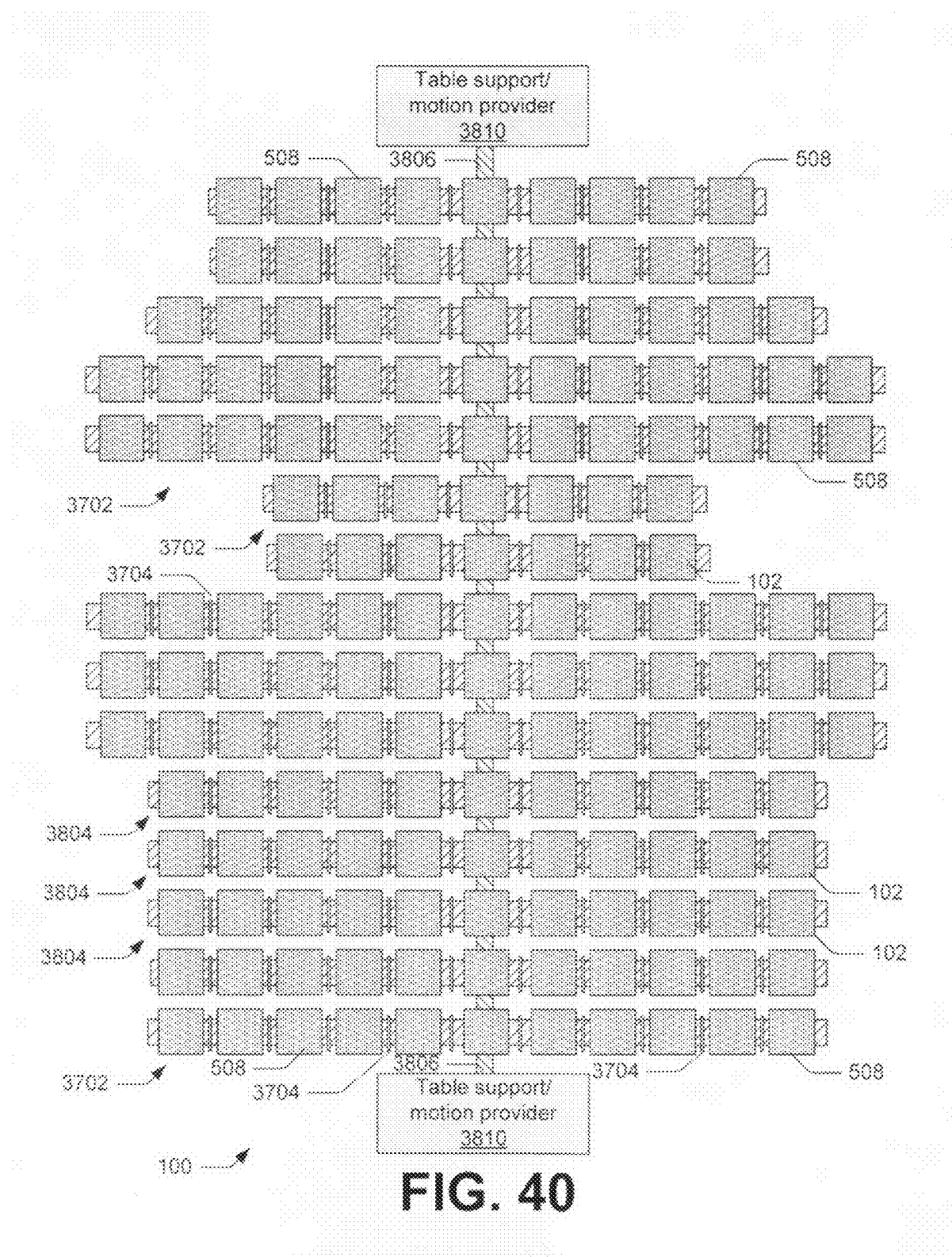
FIG. 40 is a diagram of still another embodiment of the medical displaceable contouring mechanism.
Figure 41:
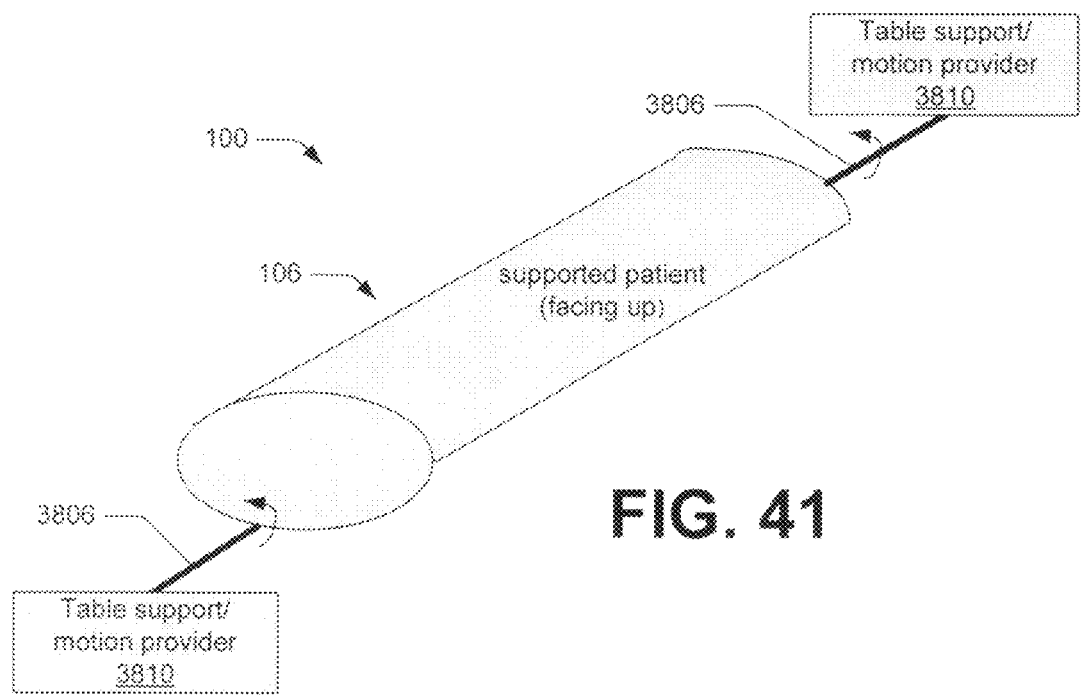
FIG. 41 is a diagram of yet another embodiment of the medical displaceable contouring mechanism.
Figure 42:
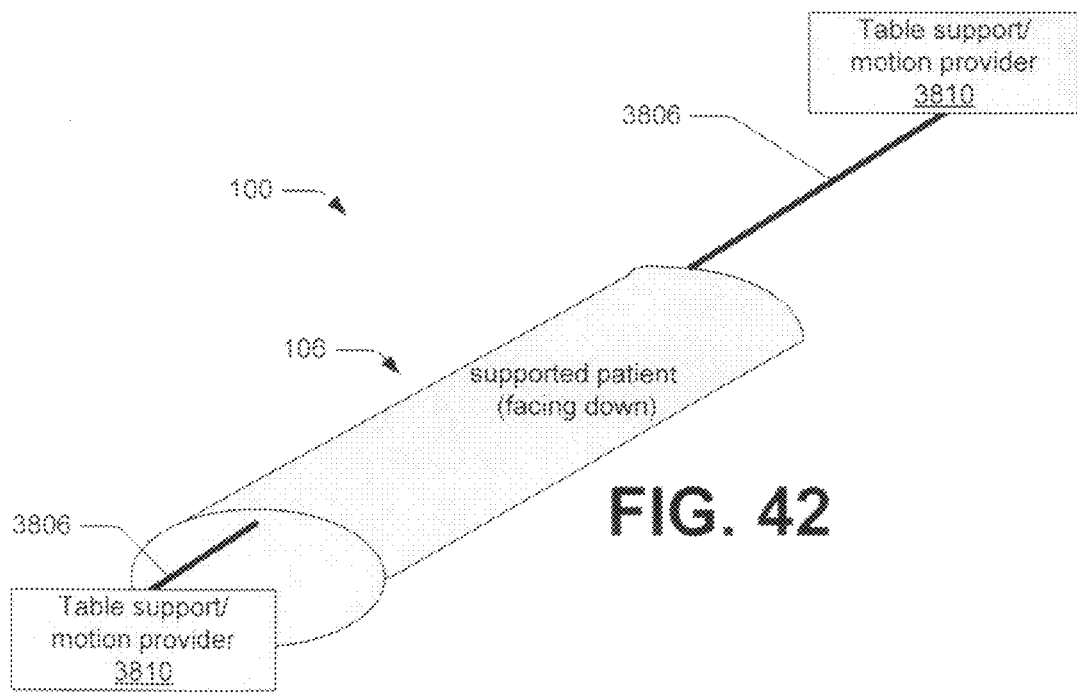
FIG. 42 is a diagram of the embodiment of the medical displaceable contouring mechanism of FIG. 41 in a varied position.

FIGS. 39 and 40 show an embodiment of the medical displaceable contouring mechanism 100 configured, for example, as an operating table, hospital bed, stretcher, ambulance stretcher, ski-toboggan, search and rescue, etc., which includes a number of the displaceable contouring unit(s) 102 as attached to respective link portions 3702, as described with respect to FIGS. 37 and 38. A number of link portions can be included in a link frame portion 3804, and a number of link frame portions 3804 may be secured to at least one connecting table frame 3806. Certain embodiments of the connecting table frame may act to relatively secure as well as position the link frame portions 3804 (and the associated displaceable contouring unit(s) 102) such that they can together act to provide support and/or stabilization to at least portions of the individual, and thereby act as the displaceable contouring unit(s) 102 as set forth in this disclosure.

Certain embodiments of the link frame portion 3804 can be configured to act manually, such that the operating room attendant, or other person, can act to displace the link frame portion 3804, as connected by the hinges 3704, and controlled by the link angle control 3706. In certain instances, for example, after the patient is anesthetized, then perhaps successive ones of the link frame portion 3804 can be displaced into position (e.g., at least partially around the individual 106). In instances where it is important to secure the individual well, or alternately position the individual in a number of positions such as during an operation or procedure, then perhaps more link frame portions 3804 can be secured. In certain instances, a fastener (not shown) can be attached to opposed ends of each link frame portion 3804, such as to allow the ends to be secured, and thereby limit the stresses that may be applied to the link frame portion 3804 if the ends are not attached.

The configuration of the medical displaceable contouring mechanism 100 including a number of the link frame portion 3804, as described with respect to FIGS. 39 and 40, can be utilized for a variety of illustrative but not limiting applications such as ambulances, stretchers, ski patrols, search and rescue, hospital beds, operating tables, etc. Certain ones of these embodiments can support, stabilize, and/or secure the individual relatively well to provide transfer of the individual to some appropriate location and/or provide a suitable treatment.

If it is desired to expose certain portions of the individual 106 such as during an operation, then certain embodiments of the link frame portion 3804 can be shortened, modified, and/or at least partially removed. As such, by not extending the full distance around the individual 106, an access port as described in this disclosure can be created as described in this disclosure. Therefore, certain embodiments of the link frame portion 3804 of the medical displaceable contouring mechanism 100 can be readily modified prior to or during use, such as to provide the desired configuration of the displaceable contouring unit(s) 102 with respect to the individual.

Certain embodiments of the medical displaceable contouring mechanism 100, as described with respect to FIGS. 39 and 40, can include a table support/motion provider 3810 that can displace the at least one connecting table frame 3806, or other desired member, to suitably reposition the individual 106 (shown schematically) within the medical displaceable contouring mechanism 100, as desired. For example, during operations or procedures, it may be desired to access different portions of the individual 106. By allowing the table support/motion provider 3810 that can reposition the individual, such processes as rolling the individual over, positioning the individual in different positions, or transferring the individual (each of which can hurt the individual as well as the person moving or rolling the individual) can be limited.

2. CERTAIN EMBODIMENTS OF THE MEDICAL DISPLACEABLE CONTOURING CONTROLLER

This disclosure describes a number of embodiments of the medical displaceable contouring controller 97 as described with respect to FIG. 4, which is intended to control at least some of the operations of certain embodiments of the medical displaceable contouring mechanism 100. Certain embodiments of the medical displaceable contouring mechanism 100 can include the medical displaceable contouring controller 97; while other embodiments of the medical displaceable contouring mechanism may not include utilizing certain embodiments of the medical displaceable contouring support controller. For instance, certain embodiments of the medical displaceable contouring mechanism 100 including the medical displaceable contouring controller 97, which can be largely microprocessor-based, and can provide for largely automated operation or assembly of the medical displaceable contouring mechanism 100. By comparison, certain embodiments of the medical displaceable contouring mechanism 100 can be operated utilizing largely manual techniques, and may not utilize the medical displaceable contouring controller 97. FIG. 4 thereby shows a block diagram of certain embodiments of the medical displaceable contouring mechanism 100 that can include the medical displaceable contouring controller 97.

Certain embodiments of the medical displaceable contouring mechanism 100 thereby can include, but is not limited to, any particular configuration of the medical displaceable contouring controller 97. Certain embodiments of the medical displaceable contouring controller 97 can be computer based, controller based, mote based, cellular telephone-based, electrical, electro-mechanical, mechanical, and/or electronics based. Certain embodiments of the medical displaceable contouring controller can be segmented into modules or network nodes, and can utilize a variety of wireless communications and/or networking technologies to allow information, data, etc. to be transferred to the various distinct portions or embodiments to perform, a variety of operations associated with of the medical displaceable contouring mechanism 100. Certain embodiments of the medical displaceable contouring controller 97 can be configured as a unitary, combined, or stand-alone device.

Certain embodiments of the medical displaceable contouring controller 97 can vary as to their automation, complexity, and/or sophistication; and can be utilized to control, setup, establish, and/or maintain communications between a number of displaceable contouring unit(s) 102. As described within this disclosure, multiple ones of the different embodiments of the displaceable contouring unit(s) 102 within the medical displaceable contouring mechanism 100 can transfer information or data relating to the communication link to or from a remote location and/or some intermediate device as might be associated with communication, monitoring and/or other activities.

Certain embodiments of the medical displaceable contouring controller 97 can be configured to contain information about the individual as well as their contour. Certain embodiments of the medical displaceable contouring controller 97 can allow for the displaceable contouring unit(s) 102 to be displaced as appropriate to compensate for the acceleration and/or forces applied to the individual such as during travel, as described in this disclosure. Certain embodiments of the medical displaceable contouring controller 97 can allow for the displaceable contouring unit(s) 102 to be displaced as appropriate to compensate for the portion of the individual that is exposed to gravitational forces based at least in part on some sensed or determined position of the individual relative to the gravitational pull. Such illustrative but not-limiting mechanisms as gyroscopes, global positioning system (GPS), inertial units, pendulum indicators, as well as a general indication by a technician as to which direction is "down" relative to gravity can be used by different embodiments of the medical displaceable contouring mechanism 100 as to determine which direction the individual is directed. The more complex gyroscopic systems, global positioning systems (GPS), and/or inertial unit systems may be used, for example, with vehicular travel or mobile embodiments of the medical displaceable contouring mechanism 100. The more straight forward (technician indicated) systems may be used by stationary embodiments of the medical displaceable contouring mechanism 100.

Certain embodiments of the contour detector 3028, as described relative to FIGS. 30 and 31 and elsewhere through the disclosure, may utilize certain embodiments of the medical displaceable contouring controller 97 as described with respect to FIG. 4 for controlling at least some of its operations. For example, in FIG. 30 the deflection of the pegs 3030 within the contour detector 3029 can be detected.

By comparison, certain embodiments of the medical displaceable contouring controller 97 can sense pressures being applied across certain of the displaceable contour unit(s) 102 using pressure sensors (not shown), and thereupon displace the higher-pressure displaceable contour unit(s) away from at least certain parts of individuals relative to lower-pressure displaceable contour unit(s), such as to reduce pressure differential between multiple displaceable contour unit(s). Such relative displacement of the displaceable contour unit(s) 102 can be performed on a real-time basis as to conform to changing contours and/or positions of the individual, or alternately on a one-time basis as to improve the contouring of the displaceable contour unit(s) 102 to the individual.

Certain embodiments of the medical displaceable contouring controller 97, as well as certain embodiments of the medical displaceable contouring mechanism 100 (in general), can utilize distinct firmware, hardware, and/or software technology. For example, mote-based technology, microprocessor-based technology, microcomputer-based technology, general-purpose computer technology, specific-purpose computer technology, Application-Specific Integrated Circuits, and/or a variety of other computer technologies can be utilized for certain embodiments of at least a portion of the medical displaceable contouring controller 97, as well as be included in certain embodiments of the medical displaceable contouring mechanism 100.

Certain embodiments of the medical displaceable contouring controller 97 can as described with respect to FIG. 4 can include a processor 803 such as a central processing unit (CPU), a memory 807, a circuit or circuit portion 809, and an input output interface (I/O) 811 that may include a bus (not shown). Certain embodiments of the medical displaceable contouring controller 97 of the medical displaceable contouring mechanism 100 can include and/or be a portion of a general-purpose computer, a specific-purpose computer, a microprocessor, a microcontroller, a personal display assistant (PDA), a cellular phone, a digital phone, a wireless communicating device, a hard-wired phone, and/or any other known suitable type of communications device, computer, and/or controller that can be implemented in hardware, software, electromechanical devices, and/or firmware. Certain embodiments of the processor 803, as described with respect to FIG. 4, can perform the processing and arithmetic operations for certain embodiments of the medical displaceable contouring controller 97 of the medical displaceable contouring mechanism 100. Certain embodiments of the medical displaceable contouring controller 97 of the medical displaceable contouring mechanism 100 can control the signal processing, database querying and response, computational, timing, data transfer, and other processes associated with certain embodiments of the medical displaceable contouring controller 97 of the medical displaceable contouring mechanism 100.

Certain embodiments of the memory 807 of the medical displaceable contouring controller 97 can include a random access memory (RAM) and/or read only memory (ROM) that together can store the computer programs, operands, and other parameters that control the operation of certain embodiments of the medical displaceable contouring controller 97 of the medical displaceable contouring mechanism 100. The memory 807 can be configurable to contain information obtained, retained, or captured by that particular medical displaceable contouring controller 97 of the medical displaceable contouring mechanism 100.

Certain embodiments of the bus can be configurable to provide for digital information transmissions between the processor 803, circuits 809, memory 807, I/O 811, and/or the image memory or storage device (which may be integrated or removable). In this disclosure, the memory 807 can be configurable as RAM, flash memory, semiconductor-based memory, of any other type of memory that can be configurable to store data pertaining to images. The bus also connects I/O 811 to the portions of certain embodiments of the medical displaceable contouring controller 97 of either the medical displaceable contouring mechanism 100 that can either receive digital information from, or transmit digital information to other portions of the medical displaceable contouring mechanism 100, or other systems and/or networking components associated therewith.

Certain embodiments of the medical displaceable contouring controller 97 of the medical displaceable contouring mechanism 100, as described with respect to FIG. 4, can include a transmitter portion (not shown) that can be either included as a portion of certain embodiments of the medical displaceable contouring controller 97 of the medical displaceable contouring mechanism 100. Certain embodiments of the medical displaceable contouring controller 97 can alternately be provided as a separate unit (e.g., microprocessor-based). In certain embodiments, the transmitter portion can transmit image information between certain embodiments of the medical displaceable contouring controller 97 of the medical displaceable contouring mechanism 100.

Certain embodiments of the medical displaceable contouring controller 97 of the medical displaceable contouring mechanism 100 as described with respect to FIG. 4 can include an operation altering portion (not shown) that can be either included as a portion of certain embodiments of the medical displaceable contouring controller 97 of the medical displaceable contouring mechanism 100, or alternately can be provided as a separate unit (e.g., microprocessor-based).

Certain embodiments of the memory 807 can provide one example of a memory storage portion. In certain embodiments, the monitored value includes but is not limited to: a percentage of the memory 807, an indication of data that is or can be stored in the memory 807, or for data storage or recording interval. To provide for overflow ability for the memory 807 of certain embodiments of the medical displaceable contouring controller 97 of the medical displaceable contouring mechanism 100, a secondary storage device can be operably coupled to the memory 807 to allow a controllable transmitting of memory data from certain embodiments of the medical displaceable contouring controller 97 of the medical displaceable contouring mechanism 100 when the monitored value of data or other information within the memory 807 exceeds a prescribed value. The prescribed value can include, e.g., some percentage amount or some actual amount of the value.

In certain embodiments, a secondary communication link can be established between the certain embodiments of the medical displaceable contouring controller 97 of the medical displaceable contouring mechanism 100. The secondary communication link can be structured in a similar manner as, or indeed act as, a communication link; or alternatively can utilize network-based computer connections, Internet connections, etc. to provide information and/or data transfer between certain embodiments of the medical displaceable contouring controller 97 of the medical displaceable contouring mechanism 100.

In certain embodiments of the medical displaceable contouring controller 97 of the medical displaceable contouring mechanism 100, the particular elements of certain embodiments of the medical displaceable contouring controller 97 of the medical displaceable contouring mechanism 100 (e.g., the processor 803, the memory 807, the circuits 809, and/or the I/O 811) can provide a monitoring function to convert raw data as displayed by an indicator. A monitoring function as provided by certain embodiments of the medical displaceable contouring controller 97 of the medical displaceable contouring mechanism 100 can be compared to a prescribed limit, such as whether the amount of information or data about positioning and/or contour contained in the memory 807, or some other measure relating to the memory is approaching some value. The limits to the value can, in different embodiments, be controlled by the user or the manufacturer of certain embodiments of the medical displaceable contouring controller 97 of the medical displaceable contouring mechanism 100. In certain embodiments, the memory 807 can store but should not be limited to such information as: data, information, displayable information, readable text, motion images, video images, and/or audio images, etc.

In certain embodiments, the I/O 811 provides an interface to control the transmissions of digital information between each of the components in certain embodiments of the medical displaceable contouring controller 97 of the medical displaceable contouring mechanism 100. The I/O 811 also provides an interface between the components of certain embodiments of the medical displaceable contouring controller 97 of the medical displaceable contouring mechanism 100. The circuits 809 can include such other user interface devices as a display and/or a keyboard. In other embodiments, the medical displaceable contouring controller 97 of the medical displaceable contouring mechanism 100 can be constructed as a specific-purpose computer such as an application-specific integrated circuit (ASIC), a microprocessor, a microcomputer, or other similar devices.

Certain embodiments of the one or more displaceable contouring unit(s) 102 can be configured to be displaced or positioned using a variety of techniques. In certain embodiments, for example, the one or more displaceable contouring unit(s) 102 can be displaced to a distance corresponding to a contour of the individual 106. Such contour can be detected physically, such as by applying a number of mechanical or electromechanical contacts against the individual (which may be spring biased against the contact), and determining how much they have deflected. In another embodiment, certain non-contact sensors such as electromagnetic contour sensors or arrayed distance sensors can be utilized to detect the contour of at least a portion of the individual, such as their skin.

Certain embodiments of the one or more displaceable contouring unit(s) 102 can be displaced against the individual 106 until a sensed pressure is sensed as being applied to the individual. As such, a number of the one or more displaceable contouring unit(s) 102 can be sequentially applied to a desired pressure, the position noted, then retracted. Each of the one or more displaceable contouring unit(s) 102 can thereupon be returned to the original position, which should thereby approximate the contour of the individual. This technique assumes that the individual is not moving between subsequent extensions and/or retractions.

As such, various embodiments of the medical displaceable contouring mechanism 100 and/or the medical displaceable contouring controller 97 can be configured utilizing relatively complex or simple computer and/or controller technology. As computer and/or controller technology evolves, it is intended that certain embodiments of the medical displaceable contouring mechanism 100 and/or the medical displaceable contouring controller 97 can be modified or adapted to utilize the modifying technology.

Certain embodiments of the contour detector 3028, as described with respect to FIGS. 30 and/or 31 can be fully computerized (e.g. be automated) or at least partially utilize a computer to derive position-related information. Certain embodiments of the medical displaceable contouring mechanism 100 as described with respect to FIGS. 1 to 29 can utilize the position-related information to position, or determine positioning, of the one or more displaceable contouring unit(s) 102. In certain embodiments, the one or more displaceable contouring unit(s) 102 can be automated to be displaced to a position at least partially based on the received position-related information. In certain embodiments, the one or more displaceable contouring unit(s) 102 can be manually positioned such as by displayed or derived position-related information. For example, each of the displaceable contouring unit(s) 102 outside a specific region will not be contacted by the individual 106, and thereby can be extended or otherwise displaced into a suitable position such as to stabilize the individual.

The embodiments of medical displaceable contouring controller 97 that is associated with the one or more displaceable contouring unit(s) 102 can be the same as, or different, from that which is associated with the contour detector 3028. Networking and/or separated controller techniques can be utilized to control the one or more displaceable contouring unit(s) 102 based at least in part on position information derived from the contour detector 3028, as described in this disclosure.

3. CERTAIN EMBODIMENTS OF THE MEDICAL DISPLACEABLE CONTOURING MECHANISM AS WELL AS THE MEDICAL DISPLACEABLE CONTOURING SUPPORT CONTROLLER WITH RELEVANT FLOWCHARTS

Within the disclosure, flow charts of the type described in this disclosure apply to method steps as performed by a computer or controller. The flow charts can also apply to apparatus devices, such as an antenna or a node associated therewith that can include, e.g., a general-purpose computer or specialized-purpose computer whose structure along with the software, firmware, electro-mechanical devices, and/or hardware, can perform the process or technique described in the flow chart.

FIG. 43 shows one embodiment of one or more of the displaceable contouring unit(s) 102 which may be configured similarly as described in the embodiments of this disclosure.

One embodiment of a high-level flowchart of a medical pressure reduction technique 2000 is described with respect to FIG. 44 and can include, but is not limited to, operation 2002 and optional operation 2004. The high-level flow chart of FIG. 44 should be considered in combination with the embodiments of the medical displaceable contouring mechanism 100, as described with respect to FIG. 43. One embodiment of operation 2002 can include, but is not limited to, reducing a pressure differential across one or more supporting surfaces of a body surface of an individual at least partially by displacing at least one displaceable contouring unit to at least partially conform to one or more contours of the body surface of the individual. For example, certain embodiments of the one or more of the displaceable contouring unit(s) 102, as described with respect to FIGS. 1 to 29 of this disclosure, can become configured to be displaced to reduce a pressure differential across one or more of the supporting surfaces of the body surface. In certain embodiments, the body surface can include a human, and animal, or an organism. One embodiment of optional operation 2004 can include, but is not limited to, stabilizing at least the one or more supporting surfaces of the body surface of the individual at least partially with at least one of the at least one displaceable contouring unit. For example, certain embodiments of the at least one displaceable contouring unit as described in this disclosure can be configured to stabilize at least a portion of the individual 106 such as with a cast, a traction mechanism, a portion that can limit lateral motion of the individual in a medical bed or on an operating table, etc. The order of the operations, methods, mechanisms, etc. as described with respect to FIG. 44 is intended to be illustrative in nature, and not limited in scope.

FIG. 45 shows one embodiment of the one or more of the displaceable contouring unit(s) 102 which may be configured similarly as described in the embodiments of this disclosure.

One embodiment of a high-level flowchart of a medical pressure reduction technique 2100 is described with respect to FIG. 46 and can include, but is not limited to, operation 2102 and optional operations 2104, 2106, and/or 2108. The high-level flow chart of FIG. 46 should be considered in combination with the embodiments of the medical displaceable contouring mechanism 100, as described with respect to FIG. 45. One embodiment of operation 2102 can include, but is not limited to, relatively displacing at least one displaceable contouring unit with respect to a medical device portion based at least in part on a contour of an individual to support at least a portion of the individual while limiting pressure applied to the individual. For example, certain embodiments of the one or more of the displaceable contouring unit(s) 102 can be relatively displaced respect to a medical device portion based at least in part on a contour of the individual to support at least a portion of the individual 106 while limiting pressure applied to the individual. For example, certain embodiments of the one or more of the displaceable contouring unit(s) 102 can be positioned relative to an individual within a medical bed, a cast, a splint, a brace, etc. One embodiment of optional operation 2104 can include, but is not limited to, stabilizing the at least the portion of the individual by displacing at least one of the at least one displaceable contouring unit. For example, displacing the one or more of the displaceable contouring unit(s) 102 into a position that can be used to stabilize the individual. One embodiment of optional operation 2106 can include, but is not limited to, limiting pressure differences as applied from multiple ones of the at least one displaceable contouring unit across the at least the portion of the individual. For example, limiting pressure differences (that can create pressure points) as applied by the one or more of the displaceable contouring unit(s) 102 across the at least the portion of the individual. One embodiment of operation 2108 can include, but is not limited to, providing an access to the individual characterized by an absence of the at least one displaceable contouring unit. For example, establishing an access port by configuring or positioning the one or more of the displaceable contouring unit(s) 102, such as to allow access to the individual. The order of the operations, methods, mechanisms, etc. as described with respect to FIG. 46 is intended to be illustrative in nature, and not limited in scope.

FIG. 47 shows one embodiment of the one or more of the displaceable contouring unit(s) 102 which may be configured similarly as described in the embodiments of this disclosure.

One embodiment of a high-level flowchart of a medical pressure reduction technique 2200 is described with respect to FIG. 48 (including FIGS. 48a and 48b) and can include, but is not limited to, operation 2202 and optional operations 2204, 2206, 2208, 2210, 2212, 2214, 2216, 2218, and/or 2220. The high-level flow chart of FIG. 48 (including FIGS. 48a and 48b) should be considered in combination with the embodiments of the medical displaceable contouring mechanism 100, as described with respect to FIG. 47. One embodiment of operation 2202 can include, but is not limited to, displacing at least one displaceable contouring unit to limit pressure differences as applied to at least a portion of an individual, wherein blood circulation in the individual can be improved at least partially in response to the displacing the at least one displaceable contouring unit. For example, certain embodiments of the one or more of the displaceable contouring unit(s) 102 as described with respect to FIGS. 1-29 can be configured to be displaced to limit pressure differences as applied to at least a portion of the individual, such as to limit pressure points, etc. One embodiment of optional operation 2204 can include, but is not limited to, positioning an at least a first one of the at least one displaceable contouring unit which can limit a pressure being applied to the at least the portion of the individual by the at least the first one of the at least one displaceable contouring unit relative to at least one other unit. For example, positioning different ones of the one or more of the displaceable contouring unit(s) 102 as to apply different pressures to the individual, based at least in part on where the different ones of the one or more of the displaceable contouring unit(s) are being applied to the individual. One embodiment of optional operation 2206 can include, but is not limited to, positioning the at least one displaceable contouring unit to stabilize the at least the portion of the individual. For example, positioning different ones of the one or more of the displaceable contouring unit(s) 102 in a first direction which does not correspond to a second direction at which the medical displaceable contouring mechanism supports the individual, or in the cast configuration in which the first direction may correspond to the second direction. One embodiment of optional operation 2208 can include, but is not limited to, positioning the at least one displaceable contouring unit to maintain a patient in a statically immobile position, thereby limiting pressure applied to pressure points or sensitive areas. For example, configuring the one or more of the displaceable contouring unit(s) 102 as to limit pressure applied to pressure points or sensitive areas (e.g., face, eyes, genitals, woman's breasts, that may even be injured or hurt during operations). One embodiment of optional operation 2210 can include, but is not limited to, physically separating the at least one of the at least one displaceable contouring unit from the individual to allow access to at least a surface region of the individual. For example, positioning the one or more of the displaceable contouring unit(s) 102 such as to create an access port, by which a physician or other person can gain access to at least a portion of the individual. One embodiment of optional operation 2212 can include, but is not limited to, applying a first pressure to the individual in a first direction at least partially with a first one of the at least one displaceable contouring unit, and applying a second pressure to the individual in a second direction at least partially using a second one of the at least one displaceable contouring unit, wherein the first direction is substantially parallel to the second direction. For example, applying different ones of the one or more of the displaceable contouring unit(s) 102 to be substantially parallel to each other. One embodiment of optional operation 2214 can include, but is not limited to, applying a first pressure to the individual in a first direction at least partially with a first one of the at least one displaceable contouring unit, and applying a second pressure to the individual in a second direction at least partially using a second one of the at least one displaceable contouring unit, wherein the first direction is at an angle to the second direction. For example, applying different ones of the one or more of the displaceable contouring unit(s) 102 to be at an angle to each other. One embodiment of optional operation 2216 can include, but is not limited to, positioning the at least one displaceable contouring unit relative to a medical displaceable contouring mechanism, wherein the at least one displaceable contouring unit can limit uneven pressure applied between the at least one displaceable contouring unit relative to the at least the portion of the individual. For example, positioning the one or more of the displaceable contouring unit(s) 102 relative to the medical displaceable contouring mechanism 100, as described in this disclosure. One embodiment of optional operation 2218 can include, but is not limited to, inflating or deflating at least one of the at least one displaceable contouring unit to extend or retract the at least one of the at least one displaceable contouring unit. For example, inflating or deflating the one or more of the displaceable contouring unit(s) 102, as described with respect to FIG. 9. One embodiment of optional operation 2220 can include, but is not limited to, wherein at least one of the at least one displaceable contouring unit can be deformed to apply a pressure against the individual. For example, deforming the one or more of the displaceable contouring unit(s) 102. The order of the operations, methods, mechanisms, etc. as described with respect to FIG. 48 (including FIGS. 48a and 48b) is intended to be illustrative in nature, and not limited in scope.

FIG. 49 shows one embodiment of the one or more of the displaceable contouring unit(s) 102 which may be configured similarly as described in the embodiments of this disclosure.

One embodiment of a high-level flowchart of a medical pressure reduction technique 2300 is described with respect to FIG. 50 and can include, but is not limited to, operation 2302. The high-level flow chart of FIG. 50 should be considered in combination with the embodiments of the medical displaceable contouring mechanism 100, as described with respect to FIG. 49. One embodiment of operation 2302 can include, but is not limited to, stabilizing at least part of an individual in a statically immobile position at least partially using displacement of at least one displaceable contouring unit. For example, maintaining the individual in the statically immobile position at least partially by limiting application of uneven forces (beyond a prescribed limit) to different ones of the one or more of the displaceable contouring unit(s) 102.

Certain embodiments of the medical displaceable contouring mechanism 100 as described with respect to FIGS. 1 to 29 can be configured to immobilize at least a portion of the individual, such as to reduce pressure on pressure points and sensitive areas. Examples of sensitive areas can include, but are not limited to, the face, the eyes, genitals, woman's breasts. etc. and other areas that could be hurt or injured by improper stabilization and/or support. The order of the operations, methods, mechanisms, etc. as described with respect to FIG. 50 is intended to be illustrative in nature, and not limited in scope.

FIG. 51 shows one embodiment of the one or more of the displaceable contouring unit(s) 102 which may be configured similarly as described in the embodiments of this disclosure.

One embodiment of a high-level flowchart of a medical pressure reduction technique 2400 is described with respect to FIG. 52 and can include, but is not limited to, operation 2402 and optional operation 2404. The high-level flow chart of FIG. 52 should be considered in combination with the embodiments of the medical displaceable contouring mechanism 100, as described with respect to FIG. 51. One embodiment of operation 2402 can include, but is not limited to, determining a contour of at least a portion of an individual. For example, using the contour determiner 3028, certain embodiments of which are described for illustrative but not limiting purposes with respect to FIGS. 30 and 31, to determine a contour of at least a portion of an individual such as a person, an animal, or an organism. One embodiment of operation 2404 can include, but is not limited to, relatively displacing at least one displaceable contouring unit to conform at least in part to the contour of the individual, wherein, when the at least one displaceable contouring unit supports the at least the portion of the individual, pressure being applied against the at least the portion of the individual can be limited. For example, displacing the one or more of the displaceable contouring unit(s) 102 as described with respect to FIGS. 1 to 29, for example, to conform to the at least the portion of the individual, which contour has been determined by the contour determiner 3028. The order of the operations, methods, mechanisms, etc. as described with respect to FIG. 52 is intended to be illustrative in nature, and not limited in scope.

In one or more various aspects, related systems include but are not limited to circuitry and/or programming for effecting the herein-referenced method aspects; the circuitry and/or programming can be virtually any combination of hardware, software, electro-mechanical system, and/or firmware configurable to effect the herein-referenced method aspects depending upon the design choices of the system designer.

4. CONCLUSION

This disclosure provides a number of embodiments of the medical displaceable contouring mechanism 100. The embodiments of the medical displaceable contouring mechanism 100, as well as certain embodiments of the displaceable contouring unit(s) 102 as described with respect to this disclosure are intended to be illustrative in nature, and are not limiting its scope.

Those having skill in the art will recognize that the state of the art in computer, controller, communications, networking, and other similar technologies has progressed to the point where there is little potential operational distinction left between hardware, firmware, and/or software implementations of aspects of systems, such as may be utilized in the medical displaceable contouring mechanism. The use of hardware, firmware, and/or software can therefore generally represent (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle can vary with the context in which the processes and/or systems and/or other technologies are deployed. For example, if an implementer determines that speed and accuracy are paramount, the implementer and/or designer of the medical displaceable contouring mechanism may opt for mainly a hardware and/or firmware vehicle. In alternate embodiments, if flexibility is paramount, the implementer and/or designer may opt for mainly a software implementation. In yet other embodiments, the implementer and/or designer may opt for some combination of hardware, software, and/or firmware. Hence, there are several possible techniques by which the processes and/or devices and/or other technologies described herein may be effected, none of which is inherently superior to the other in that any vehicle to be utilized is a choice dependent upon the context in which the vehicle can be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following recordable type media such as floppy disks, hard disk drives, CD ROMs, digital tape, and computer memory; and transmission type media such as digital and analog communication links using TDM or IP based communication links (e.g., packet links).

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

It is to be understood by those skilled in the art that, in general, that the terms used in the disclosure, including the drawings and the appended claims (and especially as used in the bodies of the appended claims), are generally intended as "open" terms. For example, the term "including" should be interpreted as "including but not limited to"; the term "having" should be interpreted as "having at least"; and the term "includes" should be interpreted as "includes, but is not limited to"; etc. In this disclosure and the appended claims, the terms "a", "the", and "at least one" positioned prior to one or more goods, items, and/or services are intended to apply inclusively to either one or a plurality of those goods, items, and/or services.

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that could have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that could have A alone, B alone, C alone, A and B together, A and C together, B and C together, and/or A, B, and C together, etc.).

Those skilled in the art will appreciate that the herein-described specific exemplary processes and/or devices and/or technologies are representative of more general processes and/or devices and/or technologies taught elsewhere herein, such as in the claims filed herewith and/or elsewhere in the present application.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method, comprising:
    alternating an applied force by
        intermittently displacing multiple contouring units along a longitudinal axis; and
        intermittently pivotably displacing a conformable portion of at least one of the multiple contorting units about an axis at an angle relative to the longitudinal axis;
        wherein alternating the applied force includes intermittently displacing in real time the multiple contouring units in response to a detected pressure differential between two or more of the multiple contouring units.

2. A method, comprising:
    alternating an applied force by
        intermittently displacing multiple contouring units along a longitudinal axis; and
        intermittently pivotably displacing a conformable portion of at least one of the multiple contorting units about an axis at an angle relative to the longitudinal axis;
        wherein alternating the applied force includes intermittently pivotably displacing the conformable portion of at least one of the multiple contorting units in response to a detected pressure differential between two or more of the multiple contouring units.

3. A method, comprising:
alternating an applied force by
intermittently displacing multiple contouring units along a longitudinal axis; and
intermittently pivotably displacing a conformable portion of at least one of the multiple contorting units about an axis at an angle relative to the longitudinal axis;
wherein alternating the applied force includes intermittently pivotably displacing in real time the conformable portion of at least one of the multiple contorting units in response to a detected pressure differential between two or more of the multiple contouring units.

4. A method, comprising:
alternating an applied force by
intermittently displacing multiple contouring units along a longitudinal axis; and
intermittently pivotably displacing a conformable portion of at least one of the multiple contorting units about an axis at an angle relative to the longitudinal axis;
wherein alternating the applied force includes intermittently pivotably displacing the conformable portion of at least one of the multiple contorting units portion about a joint member coupled to a respective one of the multiple contouring units.

5. A method, comprising:
alternating an applied force by
intermittently displacing multiple contouring units along a longitudinal axis; and
intermittently pivotably displacing a conformable portion of at least one of the multiple contorting units about an axis at an angle relative to the longitudinal axis;
wherein alternating the applied force includes varying the applied force by oscillating a displacement of one or more of the multiple contouring units.

6. An apparatus, comprising:
multiple independently displaceable contouring units, each of the multiple independently displaceable contouring units being displaceable along a longitudinal axis;
multiple conformable portions, each of the conformable portions pivotably coupled to a different one of the multiple displaceable contouring units, each of the conformable portions configured to pivot about multiple axes relative to the longitudinal axis;
a controller operably coupled to one or more of the multiple independently displaceable contouring units, the controller configured to activate a longitudinal displacement of at least one of the multiple independently displaceable contouring units; and
a controller operably coupled to one or more of the multiple conformable portions, the controller configured to activate an angular displacement of at least one of the multiple conformable portions.

7. The apparatus of claim 6, wherein at least one of the multiple independently displaceable contouring units is configured to apply a force by longitudinally displacing along a longitudinal axis and wherein at least one of the multiple conformable portions is configured to apply a force by pivotably displacing about an axes at an angle relative to the longitudinal axis.

8. The apparatus of claim 6, wherein one or more of the multiple conformable portions are pivotably coupled via a joint member to an independently displaceable contouring unit.

9. The apparatus of claim 6, wherein each of the multiple conformable portions are configured to apply a force to an individual and configured to freely pivot about multiple axes relative to the longitudinal axis in response to the applied force.

10. The apparatus of claim 6, wherein the controller operably coupled to the one or more of the multiple independently displaceable contouring units is operably coupled to an actuator configured to displace at least one of the multiple independently displaceable contouring units.

11. The apparatus of claim 6, wherein the controller operably coupled to the one or more of the multiple independently displaceable contouring units and the controller operably coupled to the one or more of the multiple conformable portions comprises a single controller.

12. An apparatus, comprising:
multiple independently displaceable contouring units, at least one of the multiple independently displaceable contouring units slidable along a longitudinal axis relative to an adjacent one of the multiple independently displaceable contouring units, each of the multiple independently displaceable contouring units being displaceable along the longitudinal axis; and
multiple conformable portions, each of the multiple conformable portions pivotably coupled to a different one of the multiple displaceable contouring units, and each of the conformable portions configured to pivot about multiple axes relative to the longitudinal axis in response to an applied force;
wherein the at least one of the multiple independently displaceable contouring units is slidable along a longitudinal axis relative-to the adjacent one of the multiple independently displaceable contouring units via a tongue-and-grove configuration.

13. An apparatus, comprising:
multiple independently displaceable contouring units, at least one of the multiple independently displaceable contouring units slidable along a longitudinal axis relative to an adjacent one of the multiple independently displaceable contouring units, each of the multiple independently displaceable contouring units being displaceable along the longitudinal axis; and
multiple conformable portions, each of the multiple conformable portions pivotably coupled to a different one of the multiple displaceable contouring units, and each of the conformable portions configured to pivot about multiple axes relative to the longitudinal axis in response to an applied force;
wherein one or more of the multiple conformable portions are pivotably coupled via a joint member to an independently displaceable contouring unit.

14. An apparatus, comprising:
multiple independently displaceable contouring units, at least one of the multiple independently displaceable contouring units slidable along a longitudinal axis relative to an adjacent one of the multiple independently displaceable contouring units, each of the multiple independently displaceable contouring units being displaceable along a longitudinal axis; and
multiple conformable portions, each of the multiple conformable portions pivotably coupled to a different one of the multiple displaceable contouring units, and each of the conformable portions configured to pivot about multiple axes relative to the longitudinal axis in response to an applied force;

wherein one or more of the multiple conformable portions are pivotably coupled via a freely pivoting joint member to an independently displaceable contouring unit.

15. An apparatus, comprising:

multiple independently displaceable contouring units, at least one of the multiple independently displaceable contouring units slidable along a longitudinal axis relative to an adjacent one of the multiple independently displaceable contouring units, each of the multiple independently displaceable contouring units being displaceable along the longitudinal axis; and multiple conformable portions, each of the multiple conformable portions pivotably coupled to a different one of the multiple displaceable contouring units, and each of the conformable portions configured to pivot about multiple axes relative to the longitudinal axis in response to an applied force;

wherein the apparatus forms part of a medical bed, an operating table, or a medical body part stabilizer.

16. An apparatus, comprising:

modulating an applied force by actuating a longitudinal displacement of multiple contouring units and an angular displacement of one or more conformable portions pivotably coupled to respective ones of the contouring units in response to a detected pressure differential between two or more contouring units in contact with an individual;

wherein modulating the applied force includes varying an applied force at a location on the individual by actuating the longitudinal displacement of at least one of the multiple contouring units proximate the location.

17. An apparatus, comprising:

modulating an applied force by actuating a longitudinal displacement of multiple contouring units and an angular displacement of one or more conformable portions pivotably coupled to respective ones of the contouring units in response to a detected pressure differential between two or more contouring units in contact with an individual:

wherein modulating the applied force includes sequentially displacing the multiple contouring units in response to a detected pressure differential between two or more contouring units in contact with the individual.

18. An apparatus, comprising:

modulating an applied force by actuating a longitudinal displacement of multiple contouring units and an angular displacement of one or more conformable portions pivotably coupled to respective ones of the contouring units in response to a detected pressure differential between two or more contouring units in contact with an individual;

wherein modulating the applied force includes oscillatively displacing the multiple contouring units in response to a detected pressure differential between two or more contouring units in contact with the individual.

19. An apparatus, comprising:

modulating an applied force by actuating a longitudinal displacement of multiple contouring units and an angular displacement of one or more conformable portions pivotably coupled to respective ones of the contouring units in response to a detected pressure differential between two or more contouring units in contact with an individual;

wherein alternating an applied force includes alternatively displacing two or more of the multiple contouring units in response to a detected pressure differential between two or more contouring units in contact with the individual.

\* \* \* \* \*